United States Patent
Satchi-Fainaro et al.

(10) Patent No.: US 11,666,656 B2
(45) Date of Patent: Jun. 6, 2023

(54) POLYMERIC CONJUGATES AND USES THEREOF

(71) Applicant: Ramot at Tel-Aviv University Ltd., Tel-Aviv (IL)

(72) Inventors: Ronit Satchi-Fainaro, Tel-Aviv (IL); Evgeni Pisarevsky, Tel-Aviv (IL); Anat Eldar-Boock, Tel-Aviv (IL); Dikla Ben-Shushan, Tel-Aviv (IL); Yana Epshtein, Tel-Aviv (IL); Anna Scomparin, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 283 days.

(21) Appl. No.: 16/079,123

(22) PCT Filed: Feb. 24, 2017

(86) PCT No.: PCT/IL2017/050236
§ 371 (c)(1),
(2) Date: Aug. 23, 2018

(87) PCT Pub. No.: WO2017/145164
PCT Pub. Date: Aug. 31, 2017

(65) Prior Publication Data
US 2019/0060477 A1   Feb. 28, 2019

Related U.S. Application Data

(60) Provisional application No. 62/299,423, filed on Feb. 24, 2016.

(51) Int. Cl.
| | | |
|---|---|---|
| *A61K 47/65* | (2017.01) | |
| *A61K 9/51* | (2006.01) | |
| *A61P 35/00* | (2006.01) | |
| *A61K 47/64* | (2017.01) | |
| *A61K 47/59* | (2017.01) | |
| *A61P 35/04* | (2006.01) | |
| *A61K 31/4184* | (2006.01) | |
| *A61K 31/506* | (2006.01) | |
| *A61K 31/4745* | (2006.01) | |

(52) U.S. Cl.
CPC ............ *A61K 47/65* (2017.08); *A61K 9/5153* (2013.01); *A61K 31/4184* (2013.01); *A61K 31/506* (2013.01); *A61K 47/59* (2017.08); *A61K 47/645* (2017.08); *A61P 35/00* (2018.01); *A61P 35/04* (2018.01); *A61K 31/4745* (2013.01); *A61K 2300/00* (2013.01)

(58) Field of Classification Search
CPC ........ A61K 47/65; A61K 9/5153; A61P 35/00
See application file for complete search history.

(56) References Cited

U.S. PATENT DOCUMENTS

| | | | | |
|---|---|---|---|---|
| 8,586,019 | B2 * | 11/2013 | Satchi-Fainaro | A61P 9/10 424/78.17 |
| 8,658,149 | B2 * | 2/2014 | Satchi-Fainaro | A61K 47/58 424/78.17 |
| 8,703,114 | B2 * | 4/2014 | Satchi-Fainaro | A61K 49/0054 424/78.17 |
| 9,095,618 | B2 * | 8/2015 | Satchi-Fainaro | C07F 9/3873 |
| 9,259,482 | B2 * | 2/2016 | Satchi-Fainaro | A61P 9/10 |
| 9,427,474 | B2 * | 8/2016 | Satchi-Fainaro | A61K 31/337 |
| 2003/0216289 | A1 * | 11/2003 | Bhatt | C07K 1/1077 514/19.3 |
| 2011/0286923 | A1 * | 11/2011 | Satchi-Fainaro | A61K 47/62 424/9.1 |
| 2015/0231069 | A1 * | 8/2015 | Modi | C08L 5/16 424/455 |

FOREIGN PATENT DOCUMENTS

| | | |
|---|---|---|
| WO | WO 2009/141823 | 11/2009 |
| WO | WO 2009/141826 | 11/2009 |
| WO | WO 2009/141827 | 11/2009 |
| WO | WO 2013/132485 | 9/2013 |
| WO | WO 2017/145164 A9 | 8/2017 |

OTHER PUBLICATIONS

Trinh et al., 2014, Treatment of BRAF-mutated advanced cutaneous melanoma, Chin Clin Oncol, 3(3): 28-39.*
Li, 2002, Poly(L-glutamic acid)-anticancer drug conjugates, Advanced Drug Delivery Reviews, 54: 695-713.*
Melancon et al., 2011, Multifunctional Synthetic Poly(L-Glutamic Acid)-Based Cancer Therapeutic and Imaging Agents, Mol Imaging, 10(1): 28-42.*
Manocha et al., 2008, Production and Characterizaton of gamma-Polyglutamic Acid Nanoparticles for Controlled Anticncer Drug Release, Critical Reviews in Biotechnology, 28(2): 83-99.*
Long et al., 2014, Combined BRAF and MEK Inhibition verses BRAF Inhibition Alone in Melanoma, The New England Journal of Medicine, 371: 1877-1888.*
Ouellet et al., 2013, Effects of Particle Size, Food, and Capsule Shell Composition on the Oral Bioavaliability of Dabrafenib, a BRAF inhibitor, in Patients with BRAF Mutation-Positive Tumors, Journal of Pharmaceutical Sciences, 102(9): 3100-3109.*
Huang et al., 2019, Isobologram Analysis: A Comprehensive Review of Methodology and Current Research, Frontiers in Pharmacology, 10: 12 pages.*
International Search Report and the Written Opinion dated May 23, 2017 From the International Searching Authority Re. Application No. PCT/IL2017/050236. (13 Pages).

(Continued)

*Primary Examiner* — Amber D Steele

(57) ABSTRACT

Polymeric conjugates comprising a polymeric matrix having associated therewith an agent that down-regulates an activity or expression of a polypeptide associated with onset or progression of melanoma, and optionally and preferably, an additional agent that acts in synergy with said agent, are provided. Synthetic methodologies for preparing these conjugates and uses thereof in treating melanoma and other cancerous diseases are also provided.

Figure 1A:
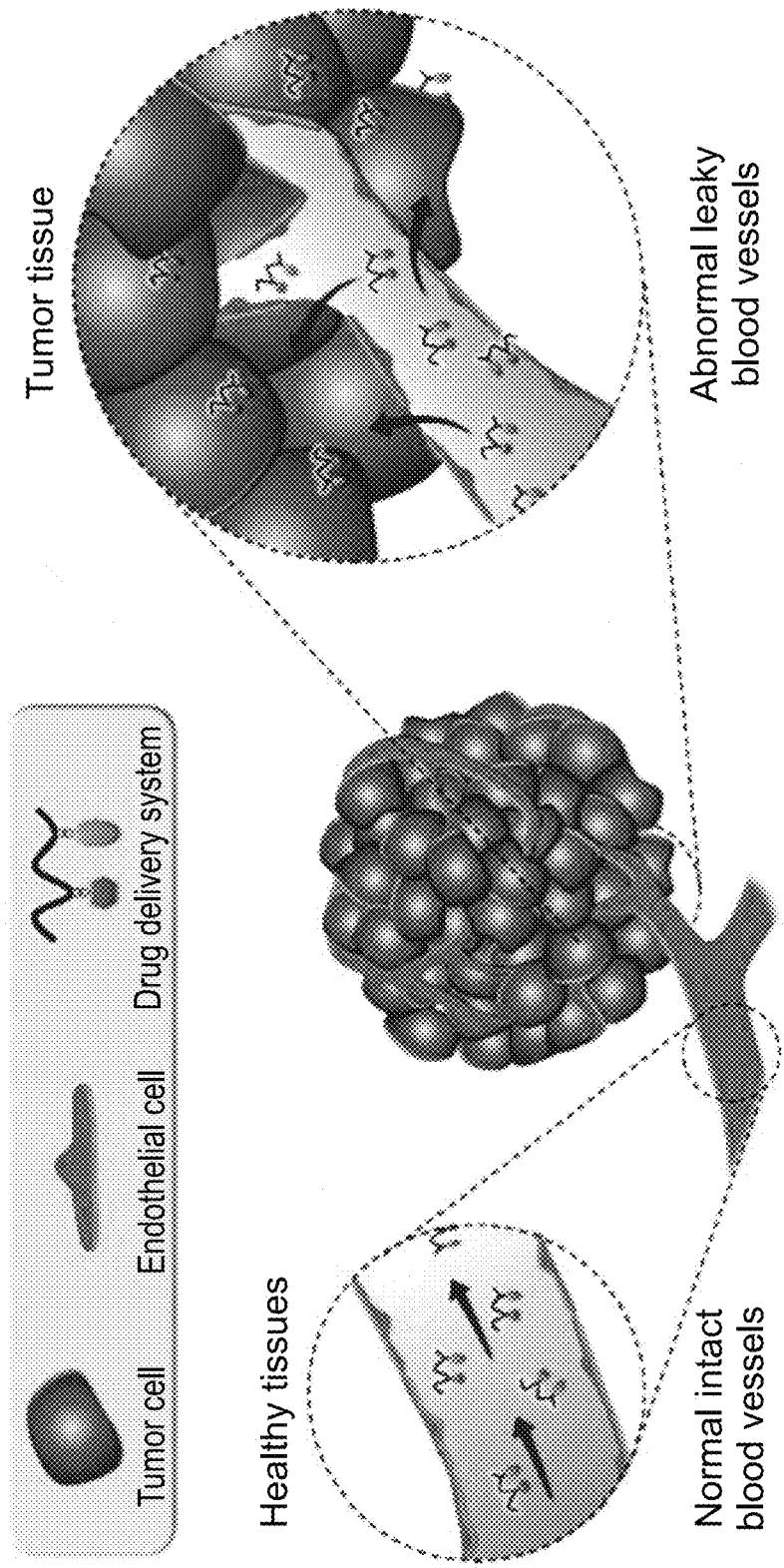

26 Claims, 24 Drawing Sheets
(23 of 24 Drawing Sheet(s) Filed in Color)
Specification includes a Sequence Listing.

(56) References Cited

OTHER PUBLICATIONS

Barras "BRAF Mutation in Colorectal Cancer: An Update", Biomarkers in Cancer, 7(Suppl.1): 9-12, Published Online Sep. 6, 2015.
Buder et al. "Systemic Treatment of Metastatic Uveal Melanoma: Review of Literature and Future Perspectives", Cancer Medicine, 2(5): 674-686, Oct. 2013.
Chapman et al. "Improved Survival With Vemurafenib in Melanoma With BRAF V600E Mutation", The New England Journal of Medicine, 364(26): 2507-2516, Published Online Jun. 5, 2011.
Davar et al. "New Therapies in the Treatment of Melanoma", Expert Opinion on Investigational Drugs, 21(11): 1643-1659, Published Online Aug. 9, 2012.
Davies et al. "Mutation of the BRAF Gene in Human Cancer", Nature, 417(6892): 949.954, Jun. 27, 2002.
Falchook et al. "Dabrafenib in Patients With Melanoma, Untreated Brain Metastases, and Other Solid Tumours: A Phase 1 Dose-Escalation Trial", The Lancet, 379(9829): 1893-1901, May 19, 2012.
Flaherty "Is It Good or Bad to Find a BRAF Mutation?", Journal of Clinical Oncology, 29(10): 1229-1230, Published Online Feb. 22, 2011.
Flaherty et al. "Combined BRAF and MEK Inhibition in Melanoma With BRAF V600 Mutations", The New England Journal of Medicine, 367(18):1694-1703, Published Online Sep. 29, 2012.
Fonkem et al. "Melanoma Brain Metastasis: Overview of Current Management and Emerging Targeted Therapies", Expert Review of Neurotherapeutics, 12(10): 1207-1215, Oct. 2012.
Guo et al. "Improving Anti-Tumor Activity of Sorafenib Tosylate by Lipid- and Polymer-Coated Nanomatrix", Drug Delivery, 24(1): 270-277, Published Online Feb. 6, 2017.
Hanley et al. "Variant Isoforms of CD44 Are P- and L-Selectin Ligands on Colon Carcinoma Cells", The FASEB Journal, 20(2): 337-339, Published Online Dec. 13, 2005.
Janne et al. "Selumetinib Plus Docetaxel for KRAS-Mutant Advanced Non-Small-Cell Lung Cancer: A Randomised, Multicentre, Placebo-Controlled, Phase 2 Study", The Lancet Oncology, 14(1): 38-47, Published Online Nov. 28, 2012.
Karal-Yilmaz et al. "Controlled Release of Imatinib Mesylate From PLGA Microspheres Inhibit Craniopharyngioma Mediated Angiogenesis", Journal of Materials Science: Materials in Medicine, 24(1): 147-153, Published Online Oct. 10, 2012.
Kim et al. "Antitumor Activity of Sorafenib-Incorporated Nanoparticles of Dextran/Poly(D1-Lactide-Co-Glycolide) Block Copolymer", Nanoscale Research Letters, 7(1): 91-96, Jan. 31, 2012.
Lee et al. "Conjugated Chitosan as a Novel Platform for Oral Delivery of Paclitaxel", Journal of Medicinal Chemistry, 51(20): 6442-6449, Published on Web Jan. 1, 2008.
Long et al. "Increased MAPK Reactivation in Early Resistance to Dabrafenib/Trametinib Combination Therapy of BRAF-Mutant Metastatic Melanoma", Nature Communications, 5(5694): 1-9, Published Online Dec. 2, 2014.
Luk et al. "BRAF Mutations in Non-Small Cell Lung Cancer", Translational Lung Cancer Research, 4(2): 142-148, Published Online Dec. 9, 2014.
Markovsky et al. "Anticancer Polymeric Nanomedicine Bearing Synergistic Drug Combination is Superior to a Mixture of Individually-Conjugated Drugs", Journal of Controlled Release, 187: 145-157, Available Online May 24, 2014.
Palama et al. "Coupled Delivery of Imatinib Mesylate and Doxorubicin With Nanoscaled Polymeric Vectors for A Sustained Downregulation of BCR-ABL in Chronic Myeloid Leukemia", Biomaterials Science, 3(2): 361-372, Sep. 26, 2014.
Patel et al. "Studies in Development of Dasatinib Nanoformulations", European Journal of Pharmaceutical and Medicinal Research, 3(7): 423-432, Jul. 2016.
Prado et al. "Skeletal Muscle Anabolism is a Sie Effect of Therapy With the MEK Inhibitor: Selumetinib in Patients With Cholangiocarcinoma", British Journal of Cancer, 106(10): 1583-1586, Published Online Apr. 17, 2012.
Qi et al. "P-Selectin-Mediated Platelet Adhesion Promotes the Metastasis of Murine Melanoma Cells", PLOS ONE, 9(3): e91320-1-e91320-7, Mar. 14, 2014.
Rafiei et al. "Docetaxel-Loaded PLGA and PLGA-PEG Nanoparticles for Intravenous Application: Pharmacokinetics and Biodistribution Profile", International Journal of Nanomedicine, 12: 935-947, Jan. 27, 2017.
Ramazani et al. "Formulation and Characterization of Microspheres Loaded With Imatinib for Sustained Delivery", International Journal of Pharmaceutics, 482(1): 123-130, Jan. 31, 2015.
Shamay et al. "P-Selectin is a Nanotherapeutic Delivery Target in the Tumor Microenvironment", Science Translational Medicine, 8(345): 345ra87-1-345ra87-28, Jun. 29, 2016.
Singh et al. "Updates in Therapy for Advanced Melanoma", Cancers, 8(1): 17-1-17-15, Jan. 15, 2016.
Takahashi et al. "Adult Classical Glioblastoma With a BRAF V600E Mutation", World Journal of Surgical Oncology, 13(100) 1-5, Mar. 11, 2015.
Tivnan et al. "Anti-GD2-Ch14.18/CHO Coated Nanoparticles Mediate Glioblastoma (GBM)-Specific Delivery of the Aromatase Inhibitor, Letrozole, Reducing Proliferation, Migration and Chemoresistance in Patient-Derived GBM Tumor Cells", Oncotarget, 8(10): 16605-16620, Feb. 3, 2017.
Wang et al. "Disulfiram-Loaded Porous PLGA Microparticle for Inhibiting the Proliferation and Migration of Non-Small-Cell Lung Cancer", International Journal of Nanomedicine, 12: 827-837, Published Online Jan. 24, 2017.
Yoo et al. "In Vitro and In Vivo Anti-Tumor Activities of Nanoparticles Based on Doxorubicin-PLGA Conjugates", Journal of Controlled Release, 68(3): 419-431, Sep. 3, 2000.
Communication Pursuant to Article 94(3) EPC Dated Apr. 20, 2020 From the European Patent Office Re. Application No. 17755949.9. (5 Pages).
Gao et al. "CXCR4-Targeted Lipid-Coated PLGA Nanoparticles Deliver Sorafenib and Overcome Acquired Drug Resistance in Liver Cancer", Biomaterials, XP055685420, 67: 194-203, Available Online Jul. 21, 2015.
O'Boyle et al. "Inhibition of CXCR4-CXCL12 Chemotaxis in Melanoma by AMD11070", British Journal of Cancer, XP055445697, 108(8): 1634-1640, Published Online Mar. 28, 2013.
Supplementary European Search Report and the European Search Opinion dated Sep. 6, 2019 From the European Patent Office Re. Application No. 17755949.9. (10 Pages).
Amaravadi et al. "Preliminary Results of a Randomized Phase II Study Comparing Two Schedules of Temozolomide in Combination With Sorafenib in Patients With Advanced Melanoma", Journal of Clinical Oncology, XP002793867, 24(18 Suppl.): 8009, Jun. 20, 2006.
Li et al. "Recent Advances in Targeted Nanoparticles Drug Delivery to Melanoma", Nanomedicine: Nanotechnology, Biology and Medicine, XP002793869, 11(3): 769-794, Published Online Dec. 30, 2014.
Mundra et al. "Nanoparticle-Mediated Drug Delivery for Treating Melanoma", Nanomedicine, XP002793868, 10(16): 2613-2633, Aug. 2015.
Ugurel et al. "Pegylated Liposomal Doxorubicin Plus Paclitaxel as an Individualized Chemosensitivity-Directed Treatment in Advanced Metastatic Melanoma", Journal of clinical Oncology, XP002793866, 25(18 Suppl.): 8551, Jun. 20, 2007.
Wang et al. "Enhanced Anti-Tumor Efficacy by Co-Delivery of Doxorubicin and Paclitaxel With Amphiphilic Methoxy PEG-PLGA Copolymer Nanoparticles", Biomaterials, XP002793865, 32(32): 8281-8290, Available Online Jul. 31, 2011.

\* cited by examiner

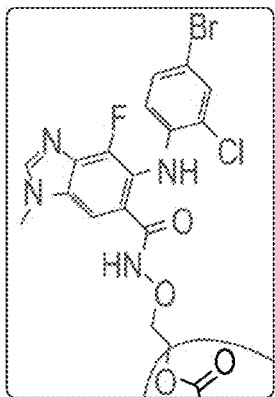
MEK inhibitor
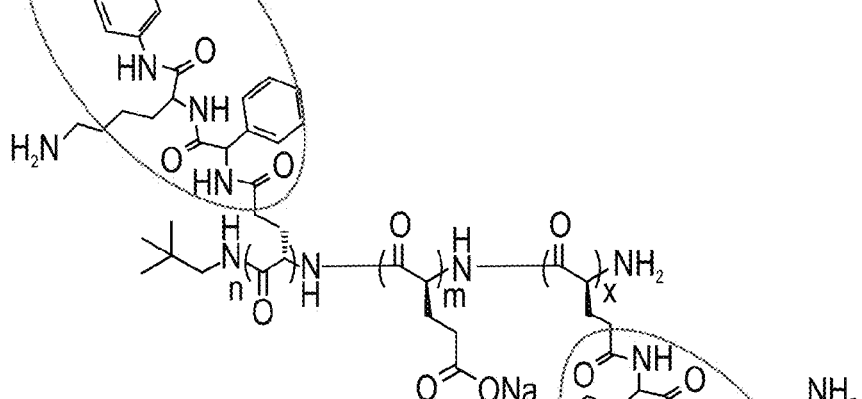
Phe-Lys-PABC linker
Phe-Lys-PABC linker
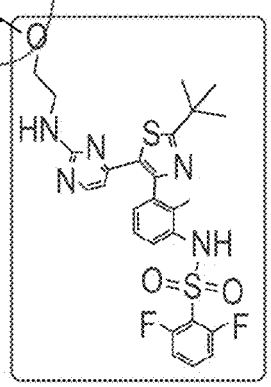
BRAF inhibitor
FIG. 21

BRAF inhibitors:
-Dabrafenib and dabrafenib modifications
-N-(3(5-(2-((2-aminoethyl)amino)pyrimidin-
4-yl)-2(tert-butyl)thiazol-4-yl)-
2-fluorophenyl)-2,6-
difluorobenzenesulfonamide
-GDC0879(905281-76-7)
-Vemurafenib(918504-65-1)

MEK 1/2 inhibitors:
-Selumetinib(606143-52-6)
-Pimasertib(1236699-92-5)
-PD318088(391210-00-7)
-TAK-733(1035555-63-5)
-Trametinib(871700-17-3)

PLGA

PLGA(BRAF-MEK1/2 inhibitor) nano particles

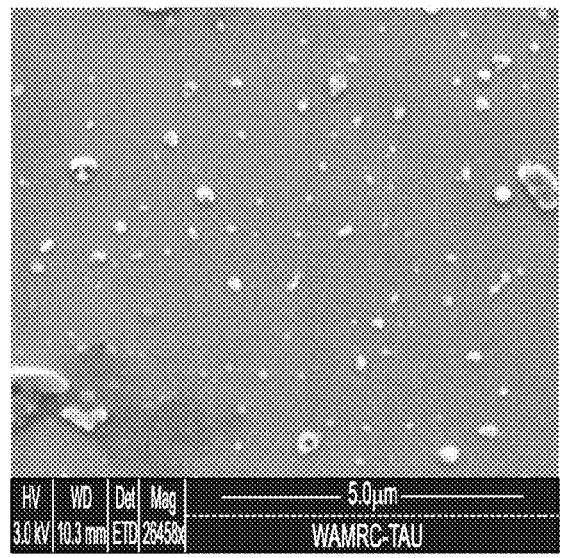 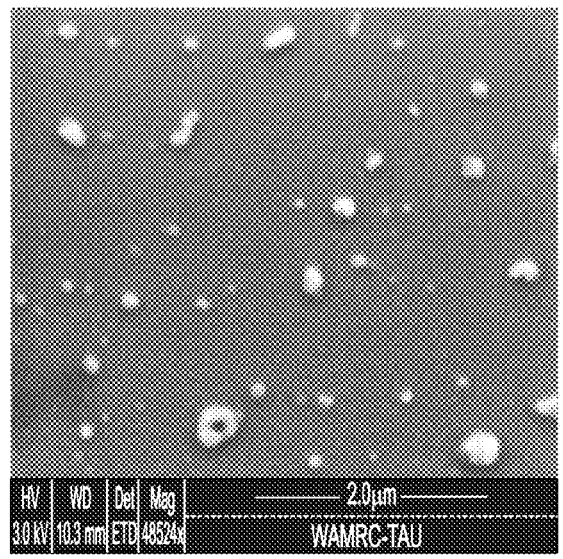
FIG. 9A
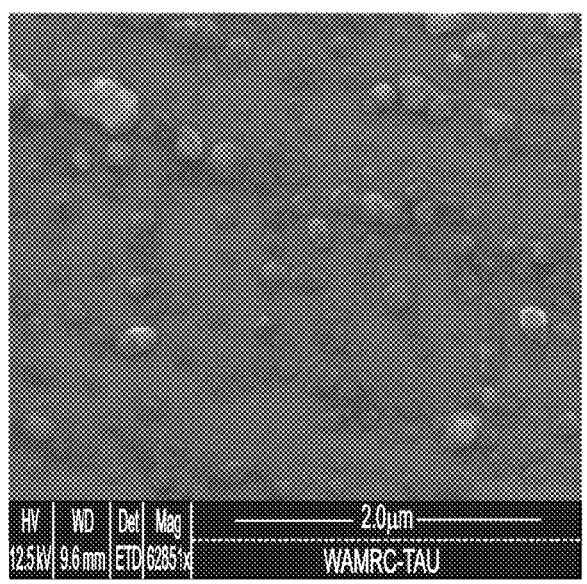 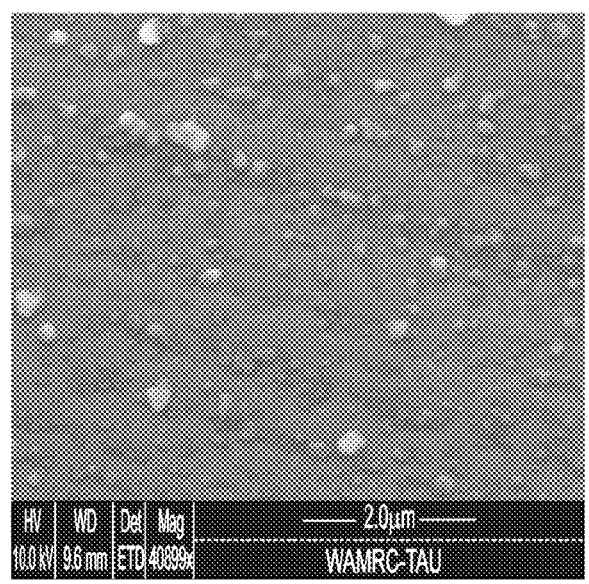
FIG. 9B

Selumetinib and Temozolomide loaded Mannose-PLGA/PLA NPs

POLYMERIC CONJUGATES AND USES THEREOF

RELATED APPLICATIONS

This application is a National Phase of PCT Patent Application No. PCT/IL2017/050236 having International filing date of Feb. 24, 2017, which claims the benefit of priority under 35 USC § 119(e) of U.S. Provisional Patent Application No. 62/299,423 filed on Feb. 24, 2016. The contents of the above applications are all incorporated by reference as if fully set forth herein in their entirety.

SEQUENCE LISTING STATEMENT

The ASCII file, entitled 74894SequenceListing.txt, was created on Apr. 30, 2020 and comprises 5,115 bytes.

FIELD AND BACKGROUND OF THE INVENTION

The present invention, in some embodiments thereof, relates to cancer therapy and, more particularly, but not exclusively, to polymeric matrices having associated therewith therapeutically active agent(s), and to uses thereof in treating various types of cancer.

The incidence of melanoma has increased dramatically during the last few decades becoming one of the most common forms of cancer. Patients with advanced metastatic melanoma have in average not more than 11 months of survival. Primary cutaneous melanomas are divided into four groups based on histopathology: superficial spreading melanoma, nodular melanoma, lentigo maligna melanoma, and acral lentiginous melanoma. Superficial spreading melanoma is the most common form. In the early growth phase, tumor cells spread laterally into the epidermis, forming an irregular pattern with an uneven color on the skin. Nodular melanoma occurs most often on the chest or back where it has a tendency to grow vertically into the skin, penetrating deeply if not removed. Nodular melanoma lesions are often characterized by a darkly-pigmented lump on the skin surface. Lentigo maligna melanoma most commonly occurs on the facial areas of elderly people. It grows slowly and may take several years to develop. Acral lentiginous melanoma is usually found on the palms of the hands, the soles of the feet, or around the toenails.

Melanoma is usually curable in its early stages, however, the disease may be fatal if it spreads to other parts of the body. Malignant melanoma usually develops via the transformation and proliferation of melanocytes that reside in the basal cell layer of the epidermis. Melanoma can also develop when melanocytes no longer respond to normal cellular growth control mechanisms, which allow the tumor cells to metastasize into nearby tissues or other organs, where they invade and compromise organ function. Thus, the development of alternative treatment for melanoma is critical and urgently needed.

Conventional chemotherapy for any cancer in general, and for recurrent and metastatic disease in particular, has limited therapeutic effect mostly due to dose-limiting toxicity and acquired resistance. On that end, a targeted approach has been developed, relying on inhibition of different key proteins in cancer progression.

C-Kit Inhibitors:

C-kit is a protein that acts as a fundamental growth factor receptor in epidermal melanocytes and has an essential role in the differentiation and migration of melanocytic cells during embryonic development [Carvajal et al. *JAMA* 305, 2327-2334 (2011)]. C-kit is also known as CD117, the receptor tyrosine kinase, found to be mutated in approximately 20% of acral, mucosal, and chronic sun-induced skin damage [Curtin et al. *Journal of Clinical Oncology* 24, 4340-4346 (2006)].

Imatinib and dasatinib, the structures of which are presented hereinbelow, are currently in clinical trials, serving as inhibitors of c-kit.

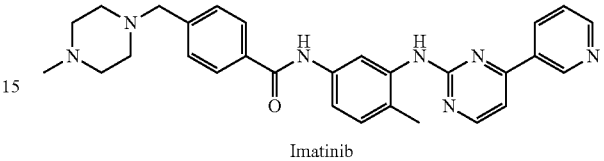

Imatinib

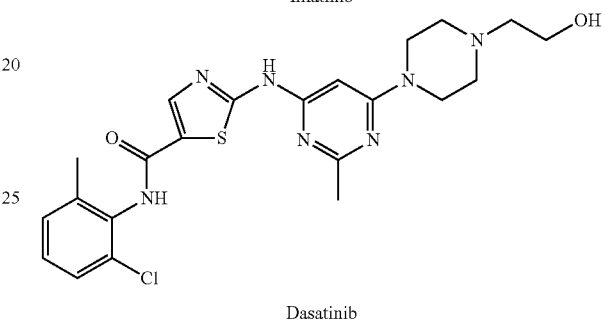

Dasatinib

BRAF/MEK Inhibitors:

The mitogen activated protein kinase (MAPK) plays an important role in extracellular signaling from the plasma membrane of the cell to its nucleus via an ordered series of different phosphorylation processes. MAPKs regulate different processes, such as proliferation, apoptosis and differentiation, of the cells [Raman et al. *Oncogene* 26, 3100-3112]. The RAS/RAF/MEK/ERK pathway plays a role in normal organogenesis; however, it can lead to malignant cellular proliferation, inhibition of apoptosis, and invasion when aberrantly activated.

In melanoma, the most commonly mutated gene is BRAF, with a frequency of 50%-70%. Up to 50% of melanoma patients have an exon 15 BRAF mutation, causing a dysregulated MAPK signaling pathway [Fonkem, E., et al. *Expert Rev Neurother* 12, 1207-1215 (2012)].

In more than 90% of the cases, this mutation occurs on the amino acid valine at position 600, which is replaced by a glutamic acid (V600E). BRAF V600E leads to ERK activation, resulting in proliferation and survival advantage of melanoma cells [Davies et al. *Nature* 417, 949-954 (2002); Davar & Kirkwood. *Expert Opinion on Investigational Drugs* 21, 1643-1659 (2012)]. Clinical data show that disease associated with BRAF mutation requires more aggressive clinical course. Patients that were treated with BRAF inhibitors showed longer overall survival compared with those that were not treated [Flaherty, K. T. *Journal of Clinical Oncology* 29, 1229-1230 (2011)].

The BRAF mutation was recently found in several cancer types, other than melanoma, including glioblastoma, colon, non-small cell lung cancer [see, for example, Takahashi, Y., et al. *World Journal of Surgical Oncology* 13, 100 (2015); Barras, D. *Biomarkers in Cancer* 7, 9-12 (2015); and Luk, P. P., et al. *Translational Lung Cancer Research* 4, 142-148 (2014)].

Three BRAF inhibitors, the structures of which are presented hereinbelow, are currently under evolution for melanoma treatment.

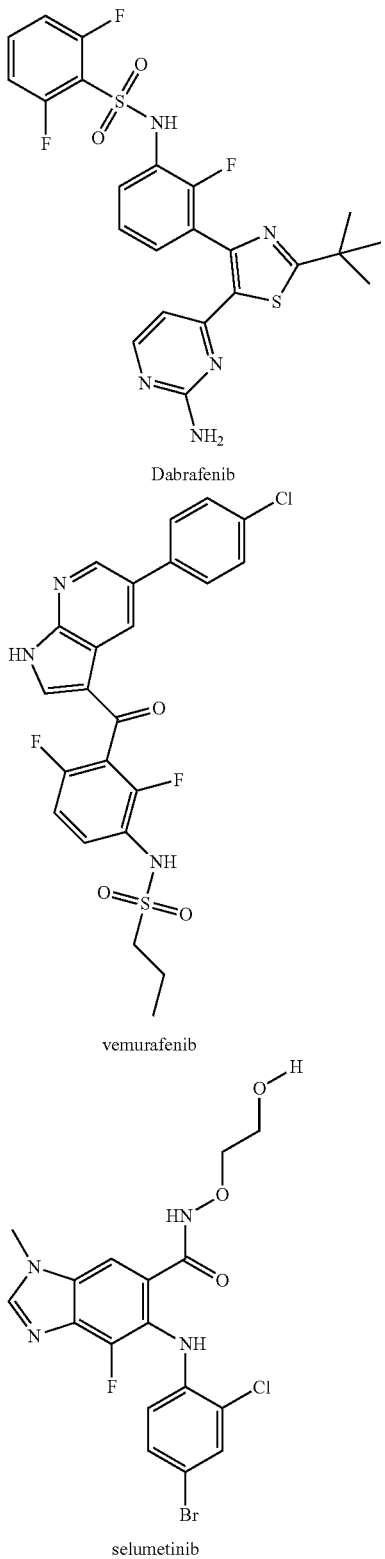

Dabrafenib vemurafenib selumetinib

Dabrafenib, a 4-(3-aminosulfonylphenyl)-5-(pyrimidin-3-yl) thiazole, is a highly selective and potent adenosine triphosphate-competitive BRAF inhibitor with more than 100-fold selectivity for mutant BRAF over wild-type BRAF as shown on cell lines. In addition, dabrafenib leads to dose-dependent inhibition of MEK and ERK phosphorylation in BRAF mutated cell lines, and induces tumor regression in melanoma xenografts. Dabrafenib was first clinically tested in study BRF112680, which was the first phase I human dose escalation study designed to evaluate its clinical efficacy, safety, and pharmacokinetics. Preliminary analysis of the initial phase I trial and an extended phase II cohort indicated that dabrafenib was active in the treatment of intracerebral melanoma metastases, with commensurate extra-cranial activity [Falchook et al. *The Lancet* 379, 1893-1901].

Highly specific and potent BRAF V600E inhibitor, designated as vemurafenib, has demonstrated promising results. In 2011, it was launched in the United States following FDA approval for BRAF V600E mutation-positive unresectable or metastatic melanoma. In a phase III randomized, controlled trial, patients with metastatic melanoma and BRAF mutation received first-line treatment with vemurafenib, and the primary endpoint was overall survival (OS). These results showed that in addition to improved OS, vemurafenib significantly reduced the risks of death and disease progression by 63% and 74%, respectively, compared to dacarbazine. The response rate in patients who received vemurafenib was 48.4%, which was almost 9 times higher than that in patients who received conventional chemotherapy (5.5%). Furthermore, 84% of the patients who received vemurafenib were alive after 6 months compared to 64% of those who received dacarbazine, i.e., the median OS with vemurafenib (10.5 months) was longer than that with dacarbazine. See, Chapman et al. *New England Journal of Medicine* 364, 2507-2516 (2011).

MEK is a protein that belongs to the MAPK pathway downstream of BRAF. Selumetinib, an orally-administered selective inhibitor of MEK1/2, was developed for the potential treatment of patients with cancers, such as NSCLC, pancreatic cancer, colorectal cancer, biliary cancer, and thyroid carcinoma [rado et al. *Br J Cancer* 106, 1583-1586 (2012)]. Selumetinib monotherapy has shown no clinical benefits over chemotherapy. Nonetheless, addition of selumetinib to chemotherapeutic agents commonly used in these diseases, showed promising results. For example, synergistic combinations of drugs were selumetinib with docetaxel for KRAS-mutant advanced non-small-cell lung cancer [Jänne et al. *The Lancet Oncology* 14, 38-47 (2013)], and selumetinib with temozolomide in patients with advanced uveal melanoma [Buder et al. *Cancer Medicine* 2, 674-686 (2013)]. Trematinib combined with debrafinib showed promising results for melanoma [Flaherty et al. *New England Journal of Medicine* 367, 1694-1703 (2012)]. Increased MAPK reactivation in early resistance to dabrafenib/trametinib combination therapy of BRAF-mutant metastatic melanoma was observed and resistance is usually developed in 6-9 months [Long, G. V., et al. *Nat Commun* 5(2014)]. New combinations of drugs that target other pathways or other compartment of the tumor are sought for, for improved treatment.

P-Selectin:

P-selectin is a cell adhesion molecule responsible for leukocyte recruitment and platelet binding, which is expressed constitutively in endothelial cells. Upon endothelial activation with ionizing radiation, P-selectin translocates to the cell membrane [Hallahan et al. *Cancer Res* 58, 5216-5220 (1998); Bonfanti et al. *Blood* 73, 1109-1112 (1989)]. Elevated P-selectin expression has been found in the vasculature of human lung, breast, colon and kidney cancers [Hanley, W. D., et al. *FASEB J* 20, 337-339 (2006); Shamay, Y., et al. *Science translational medicine* 8, 345ra387 (2016)]. P-selectin has also been reported to promote metastasis in melanoma murine model [Qi, C.-L., et al. *PloS one* 9, e91320 (2014)]. Recently, P-sel expression was found in GB cells, both on cell lines and patient-derived primary cells (Ferber et al. P-Selectin targeted delivery of PTX to brain tumors across the BBB using dendritic polyglycerol sulfate. in press).

Polymeric Drug Delivery:

Chemotherapy has had limited success in the treatment of cancer over the years. This can be attributed, in part, to the untoward toxicity of the therapeutic agent to normal cells. The design of tailor-made polymer conjugates provides a synthetic approach that can overcome some of the problems. Limited therapeutic effect due mostly to dose-limiting toxicity, limited aqueous solubility, in vivo instability, poor pharmacokinetics and no selectivity of promising anticancer drugs have long been stumbling blocks in anticancer drug development. A polymer-drug conjugate model has been proposed for delivering an anticancer drug to a tumor, and has been recognized to have enhanced uptake and to persist longer in tumors than in normal tissues, even in the absence of a targeting moiety. This effect was coined as 'the enhanced permeability and retention (EPR) effect', and the phenomenon has been attributed to the greater permeability of disordered capillary endothelia in malignant tumors towards macromolecules than normal tissue and the poorly-functional lymphatics in solid tumors, as schematically illustrated in Background Art FIG. 1A.

Several synthetic polymers have been successfully introduced into clinical practice, including polyethylene glycol (PEG), polystyrene-maleic anhydride copolymer (SMA), N-(2-hydroxypropyl)-methacrylamide copolymer (HPMA), and poly($\alpha$,L-glutamic acid) (PGA). Most polymers can be divided into non-degradable and biodegradable polymers. Several synthetic polymer-based anticancer drug conjugates have entered clinical trials, i.e., PK1 [Putnam, D. & Kopeček, J. in Biopolymers II, Vol. 122 (eds. Peppas, N. & Langer, R.) 55-123 (Springer Berlin Heidelberg, 1995)], Opaxio [Langer, C. J., et al. Journal of Thoracic Oncology 3, 623-630 (2008)] and SMANCS [Maeda, H. Advanced Drug Delivery Reviews 46, 169-185 (2001)].

Poly ($\alpha$,L-Glutamic Acid)(PGA):

PGA is composed of naturally occurring L-glutamic acid linked together through amide bonds, rather than a non-degradable C—C backbone. The pendent free $\gamma$-carboxyl group in each repeating unit of L-glutamic acid is negatively charged at a neutral pH, which renders the polymer water soluble. The carboxyl groups also provide functionality for drug attachment. PGA is non-immunogenic, non-toxic, and biodegradable by cathepsin B, an enzyme that is highly expressed in most tumor tissues. These features make PGA a promising candidate as a carrier in polymer-drug conjugates for selective delivery of anticancer drugs. The cellular uptake of negatively charged polymers can be hindered due to electrostatic repulsion forces between the polymers and the rather negatively charged surface of the cells. Although PGA is no exception to this rule, it does not diminish the EPR effect and the accumulation and retention of PGA-drug conjugates in solid tumors.

One of the conjugates that already passed phase 1 and phase 2 clinical trials is CT-2103 consisting of PGA-paclitaxel (PTX). CT-2103 has $IC_{50}$ fifty percent higher than free drug but it is much less toxic and the maximum tolerated dose (MTD) of the conjugate was twice higher than the free drug even in patients who have failed prior taxane therapy [Singer, J., et al. in *Polymer Drugs in the Clinical Stage*, Vol. 519 (eds. Maeda, H., Kabanov, A., Kataoka, K. & Okano, T.) 81-99 (Springer US, 2003)]. Moreover, 10-fold amount of CT-2103 accumulated in the tumor in female mice (C57BL/6) bearing subcutaneous B16 melanoma compared to free PTX.

WO 2013/132485 describes, inter alia, a PGA-Paclitaxel-Doxorubicin (PGA-PTX-DOX) conjugate that demonstrated the benefits of polymer conjugation for selective biodistribution and enhanced therapeutic effect of two drugs on the same polymeric chain compared to each of them alone or a mixture of two separate conjugates. See also Markovsky et al. *J. Controlled Release* 187, 145-157 (2014).

Poly (Lactic-Co-Glycolic Acid) (PLGA):

PLGA is a biocompatible and biodegradable FDA-approved polymer, synthesized by co-polymerization of lactic acid and glycolic acid. It is widely used as drug carrier owing to its tunable properties according to polymer composition (lactic acid/glycolic acid ratio), crystallinity and MW. PLGA is often used in pharmaceutical formulations as a copolymer of PEG, to obtain nanoparticles with improved physico-chemical and biological properties.

Several PLGA-based nanoparticles have been developed for the delivery of anticancer drugs for the treatment of cancer, relying both on vasculature-dependent accumulation (EPR effect) and on receptor-mediated targeting. See, for example, Yoo et al. Journal of controlled release: official journal of the Controlled Release Society 68, 419-431 (2000); Rafiei, P. & Haddadi, A. International journal of nanomedicine 12, 935-947 (2017); Wang, C., et al. International journal of nanomedicine 12, 827-837 (2017); and Tivnan, A., et al. Oncotarget (2017).

Additional background art includes WO 2009/141823, WO 2009/141826 and WO 2009/141827.

SUMMARY OF THE INVENTION

According to an aspect of some embodiments of the present invention there is provided a polymeric conjugate comprising a polymeric matrix having associated therewith a first agent, the first agent down-regulates an activity or expression of a polypeptide associated with onset or progression of melanoma.

According to some of any of the embodiments described herein, the polypeptide associated with onset or progression of melanoma is selected from MEK, BRAF and c-kit.

According to some of any of the embodiments described herein, the first agent is an agent that down-regulates MEK and/or BRAF.

According to some of any of the embodiments described herein, the first agent is selected from the group consisting of selumetinib, dabrafenib, vemurafenib, PD318088, pimasertib, cobimetinib, sorafenib, LGX818, GDC 0879, imatinib, dasatinib and a structural analog thereof.

According to some of any of the embodiments described herein, the polymeric matrix further comprises an additional agent associated therewith, the additional agent acts in synergy with the first agent in the treatment of melanoma.

According to some of any of the embodiments described herein, additional agent is a second agent that down-regulates an activity or expression of a polypeptide associated with onset or progression of melanoma.

According to some of any of the embodiments described herein, the additional agent is a second agent that down-regulates MEK and/or BRAF, the second agent being different from the first agent.

According to some of any of the embodiments described herein, the second agent is selected from the group consisting of selumetinib, dabrafenib, vemurafenib, PD318088, Pimasertib, GDC 0879 and a structural analog thereof.

According to some of any of the embodiments described herein, the additional agent is an anti-angiogenesis agent.

According to some of any of the embodiments described herein, the additional agent is paclitaxel.

According to some of any of the embodiments described herein, the additional agent is temozolomide or campothecin.

According to some of any of the embodiments described herein, the polymeric matrix comprises a polymeric backbone comprised of a plurality of backbone units, wherein a first portion of the backbone units has the first agent covalently attached thereto.

According to some of any of the embodiments described herein, the polymeric matrix further comprises an additional agent that acts in synergy with the first agent in the treatment of melanoma, the additional agent being covalently attached to a second portion of the backbone units.

According to some of any of the embodiments described herein, at least one of the first agent and the additional agent, if present, is attached to the backbone units via a linker.

According to some of any of the embodiments described herein, the linker is a biodegradable linker.

According to some of any of the embodiments described herein, the linker is a hydrolysable linker.

According to some of any of the embodiments described herein, the biocleavable linker is an enzymatically cleavable linker.

According to some of any of the embodiments described herein, the enzymatically cleavable linker is cleaved by an enzyme which is overexpressed in melanoma cells.

According to some of any of the embodiments described herein, the conjugate is represented by Formula I:

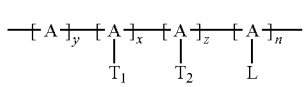

Formula I wherein: A is a backbone unit within the polymeric backbone; A-T1 is a backbone unit within the polymeric backbone having attached thereto the first agent; A-T2 is a backbone unit within the polymeric backbone having attached thereto an additional agent that acts in synergy with the first agent in the treatment of melanoma; A-L is a backbone unit having attached thereto a targeting moiety; y ranges from 50 to 99.9 mol percent; x ranges from 0.1 to 50 mol percent; z ranges from 0 to 50 mol percent; and n ranges from 0 to 10 mol percents.

According to some of any of the embodiments described herein, the plurality of backbone units forms a polymeric backbone corresponding to a polymeric backbone of polyglutamic acid (PGA).

According to some of any of the embodiments described herein, the polymeric matrix comprises a plurality of particles, and the first agent is associated with at least a first portion of the particles.

According to some of any of the embodiments described herein, the conjugate further comprises an additional agent that acts in synergy with the first agent, the additional agent is associated with at least a second portion of the particles.

According to some of any of the embodiments described herein, the conjugate further comprises an additional agent that acts in synergy with the first agent, the additional agent is associated with the at least a first portion of the particles.

According to some of any of the embodiments described herein, the particles comprise PLGA.

According to some of any of the embodiments described herein, the conjugate further comprises a targeting moiety attached to the polymeric matrix, the targeting moiety being a ligand of a cell-surface receptor expressed in melanoma cells.

According to an aspect of some embodiments of the present invention there is provided a pharmaceutical composition comprising the polymeric conjugate as described herein in any of the respective embodiments and any combination hereof, and a pharmaceutically acceptable carrier.

According to an aspect of some embodiments of the present invention there is provided a conjugate as described herein in any of the respective embodiments and any combination hereof, or a composition as described herein in any of the respective embodiments and any combination hereof, for use in the treatment of a cancerous disease associated with the polypeptide.

According to an aspect of some embodiments of the present invention there is provided a conjugate as described herein in any of the respective embodiments and any combination hereof, or a composition as described herein in any of the respective embodiments and any combination hereof, for use in the treatment of melanoma.

According to an aspect of some embodiments of the present invention there is provided a process of preparing the conjugate of any one of claims 12-26, the process comprising coupling the first agent, and optionally the additional agent, if present, to a polymer corresponding to the polymeric backbone.

According to some of any of the embodiments described herein, the process further comprises, prior to the coupling, modifying the first agent and/or the additional agent, to thereby generate a reactive group chemically compatible with a reactive group of the polymer.

According to an aspect of some embodiments of the present invention there is provided a structural analog of an agent that down-regulates activity or expression of a polypeptide associated with onset of progression of melanoma, the analog comprising a reactive group usable in coupling the agent to the polymeric backbone as described herein.

According to an aspect of some embodiments of the present invention there is provided a process of preparing PGA, essentially as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A (Background Art) presents a schematic illustration of the EPR effect, showing healthy tissue with an intact blood vessel compared to permeable blood vessel within the tumor tissue [Ferber et al. in *Cancer Targeted Drug Delivery* (eds. Bae, Y. H., Mrsny, R. J. & Park, K.) 509-542 (Springer New York, 2013)].

Figure 1B:
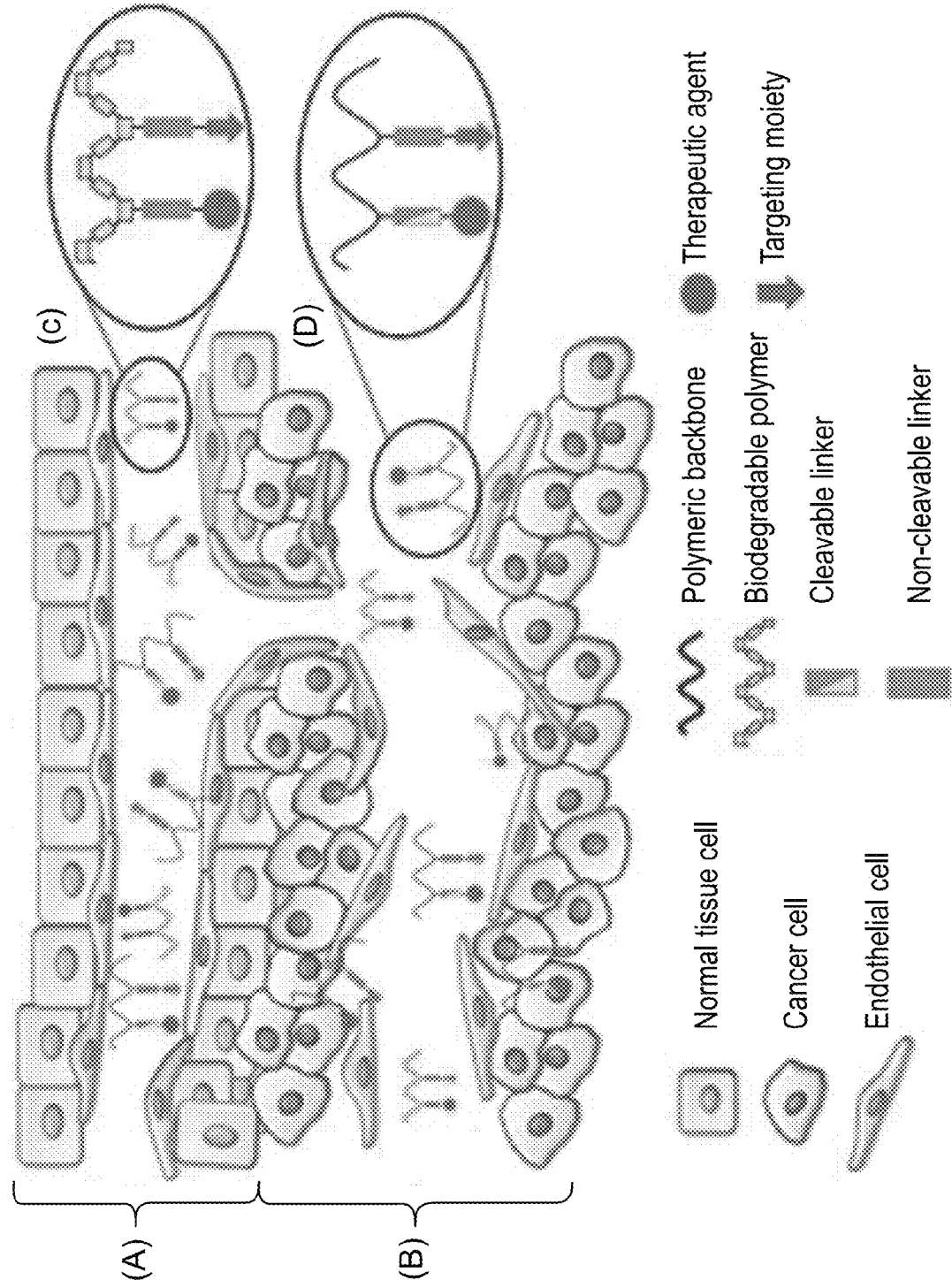

FIG. 1B (Background Art) presents a schematic illustration of the EPR effect, showing passive targeting of polymers to cancer site. (A) denotes healthy tissue with an intact blood vessel. (B) denotes permeable blood vessel within the tumor tissue. (C) denotes biodegradable polymeric backbone with a therapeutic agent and a targeting moiety. (D) denotes non-degradable (biostable) polymeric backbone with a therapeutic agent and a targeting moiety [Polyak et al. *Polym. Adv. Technol.* 24, 777-790 (2013)].

FIGS. 2A-K present the chemical structures of exemplary polymeric conjugates according to some embodiments of the present invention, featuring biodegradable linkers linking the therapeutically active agents to the respective polymeric backbone units. In FIGS. 2A-E the biodegradable linker is GFLG (SEQ ID NO:15).

Figure 3A:
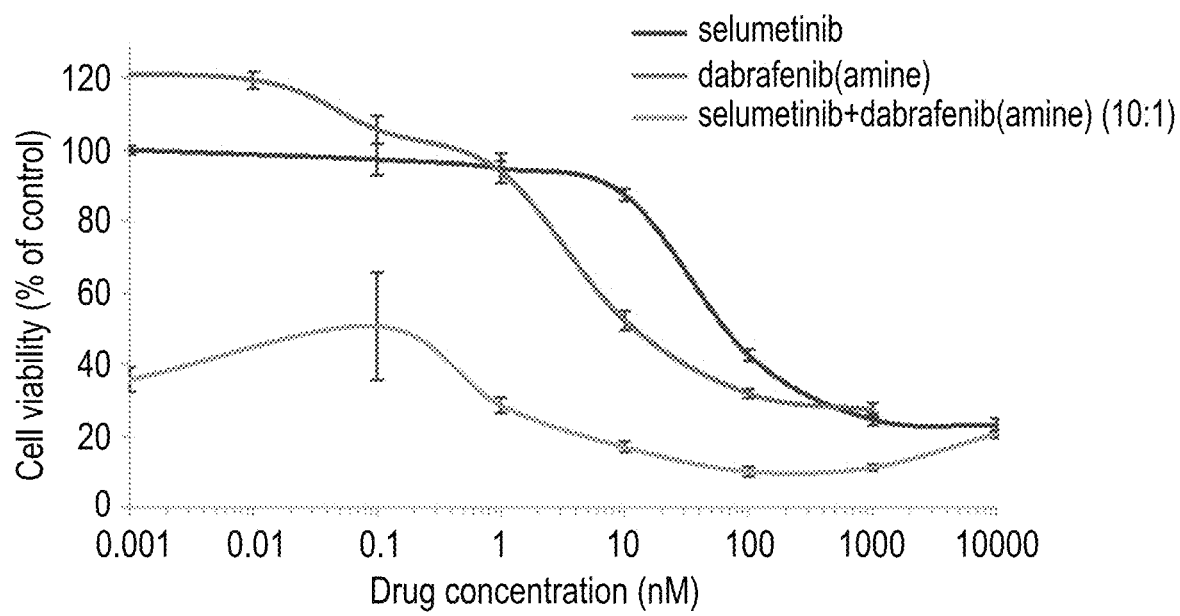
Figure 3B:
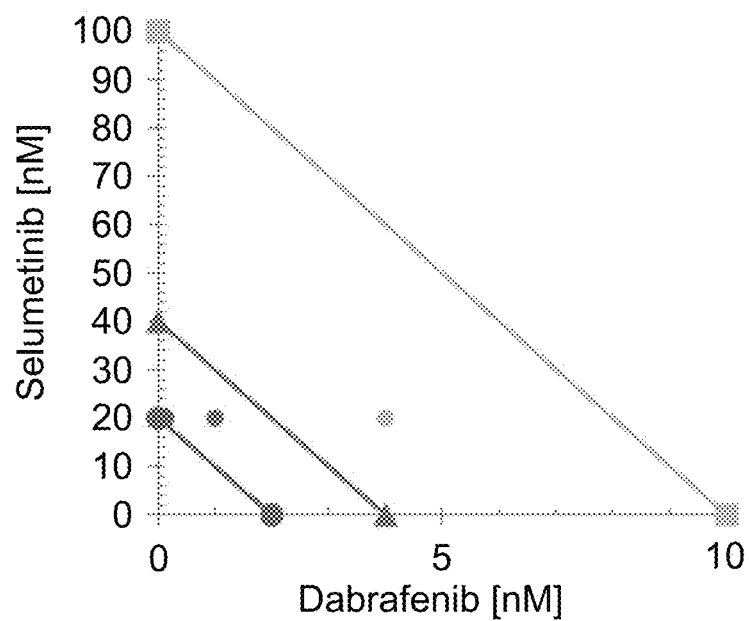

FIGS. 3A-B present comparative plots (FIG. 3A) and an Isobologram (FIG. 3B) showing that selumetinib and dabrafenib inhibit synergistically the proliferation of melanoma cells when conjugated to a polymeric backbone chain at a 10:1 mol ratio.

Figure 4A:
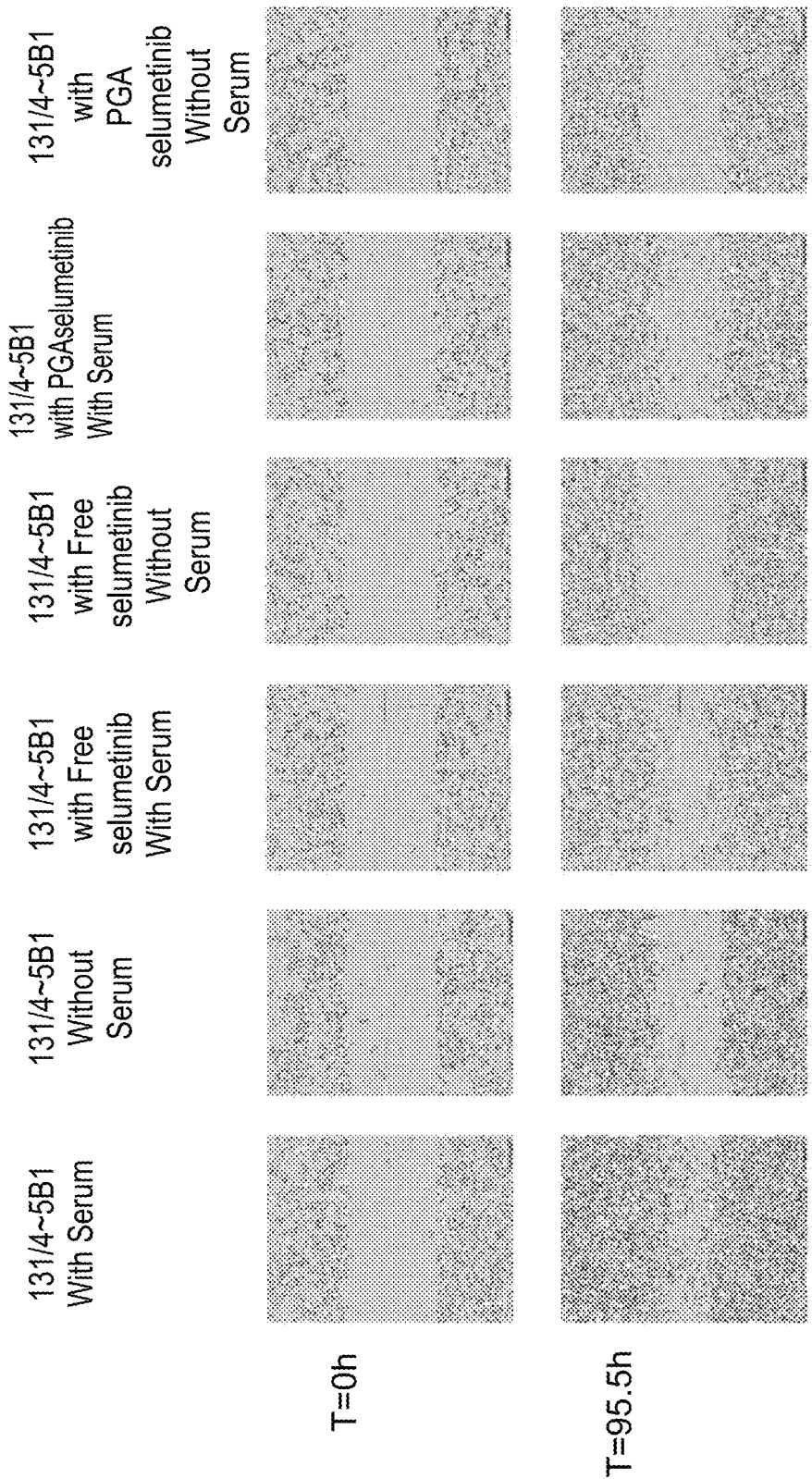
Figure 4B:
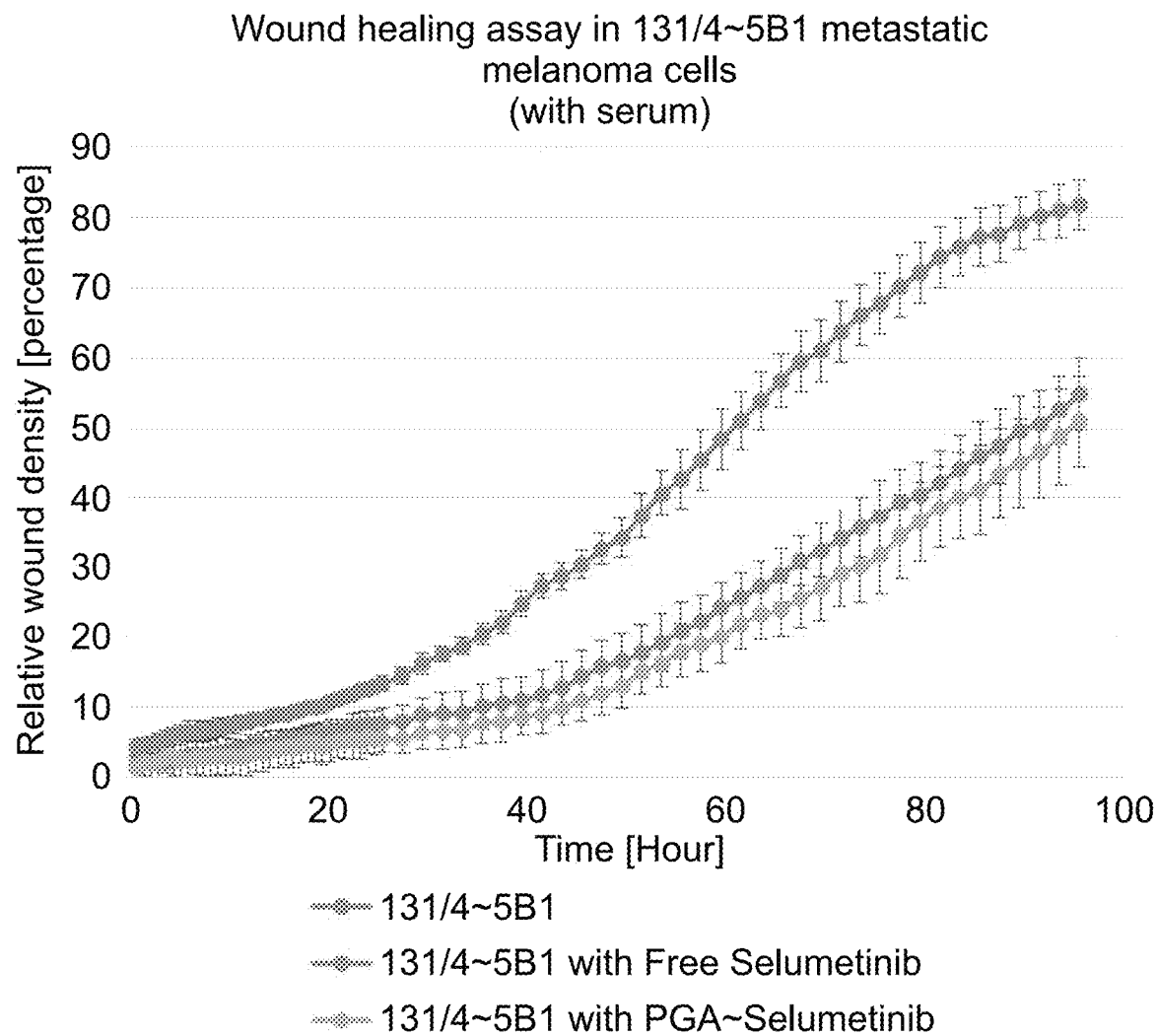
Figure 4C:
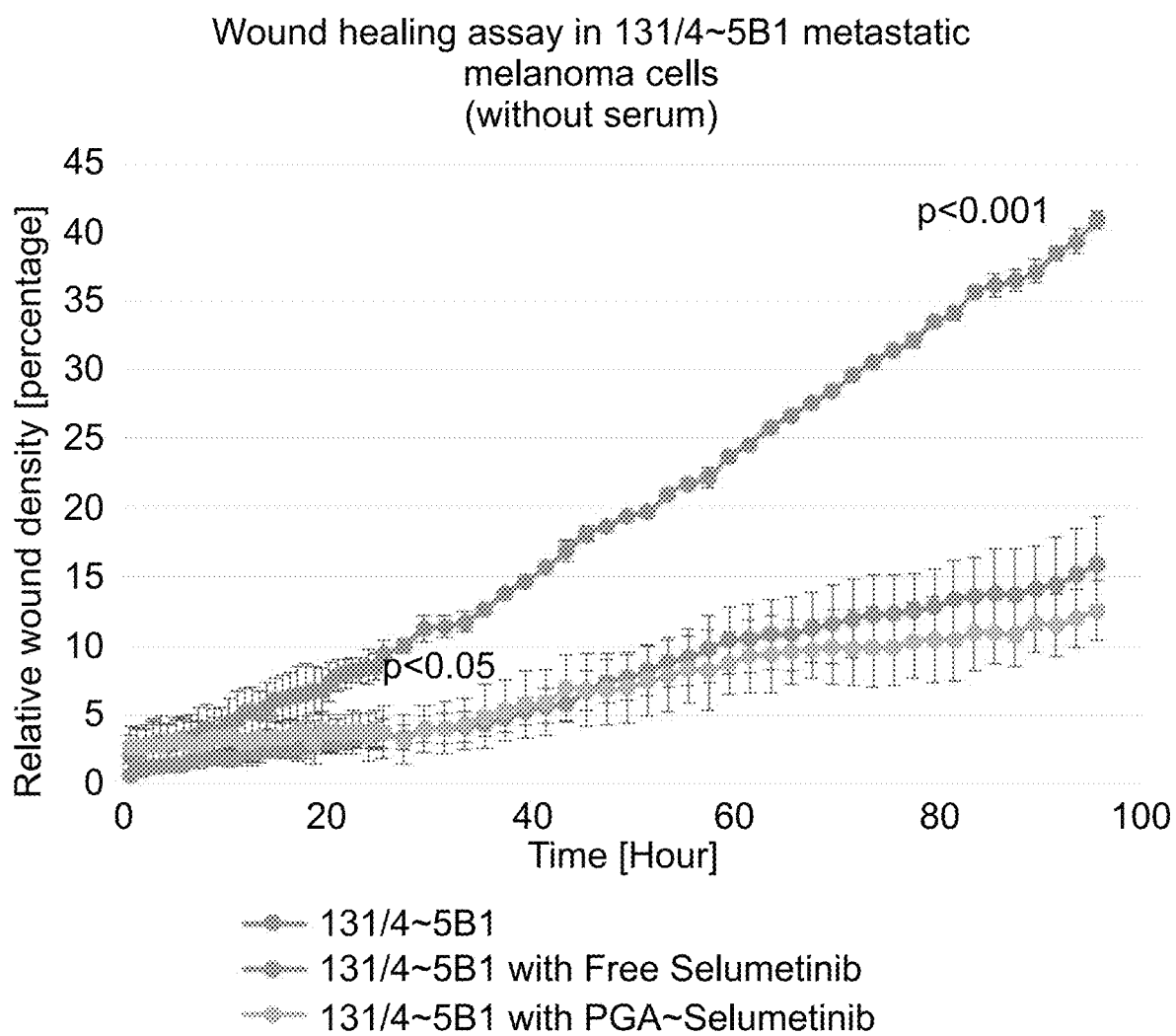

FIGS. 4A-C present data obtained in a wound healing assay conducted with melanoma cells grown with or without serum, in the presence free selumetinib, PGA-selumetinib and control (cells only). FIG. 4A presents images of a monolayer of melanoma cells that have undergone a scratch obtained prior to treatment (T=0) and the end of the incubation period with the different treatments (T=95.5 h). FIGS. 4B and 4C present comparative plots showing the relative density of wound in cells grown with serum (FIG. 4B) and without serum (FIG. 4C) from time=0 to 95 hours after treatment. Blue plots show data obtained for cells only, Orange plots for cells treated with free selumetinib, and Grey plots for cells treated with PGA-selumetinib. Wound healing scale bar 0.3 cm=300 μm.

Figure 5A:
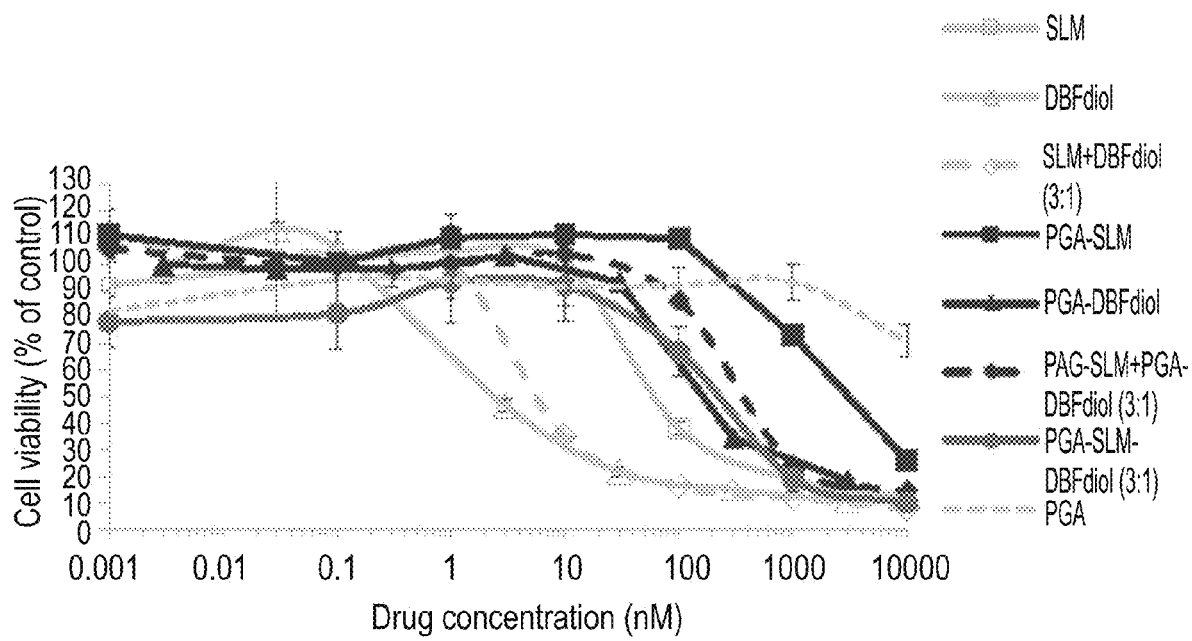
Figure 5B:
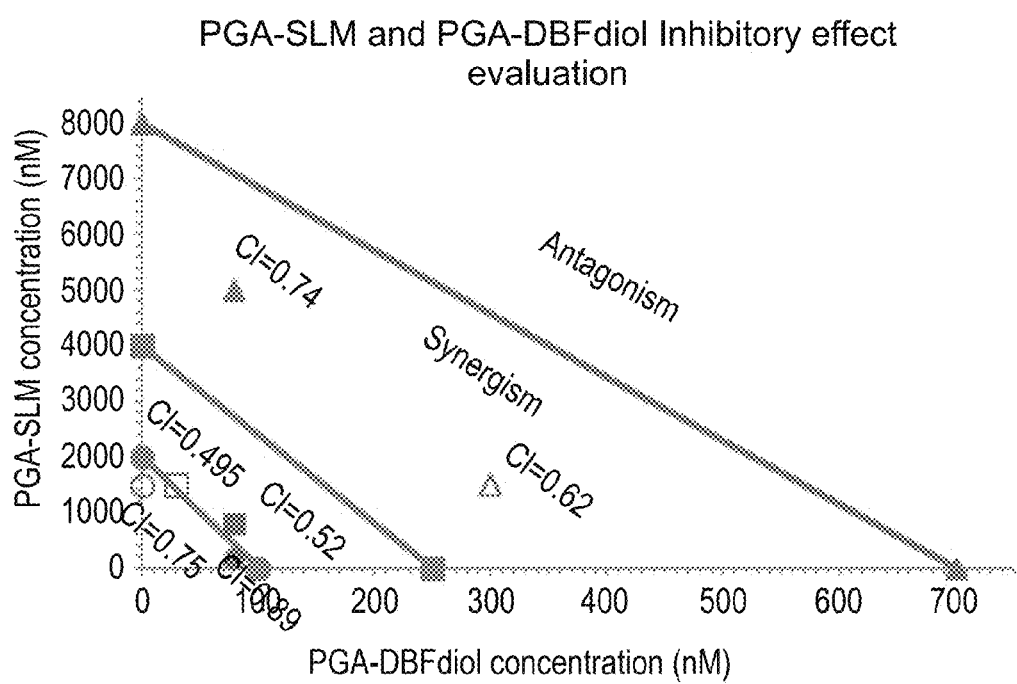

FIGS. 5A-B present comparative plots (FIG. 5A) and an Isobologram (FIG. 5B) showing inhibition of proliferation of 131/4-5B1 melanoma cells by free selumetinib, free dabrafenib-diol, their combination, PGA-selumetinib, PGA-dabrafenib(diol), the combination of both separate conjugates and PGA-selumetinib-debrafenib(diol) conjugate.

Figure 6:
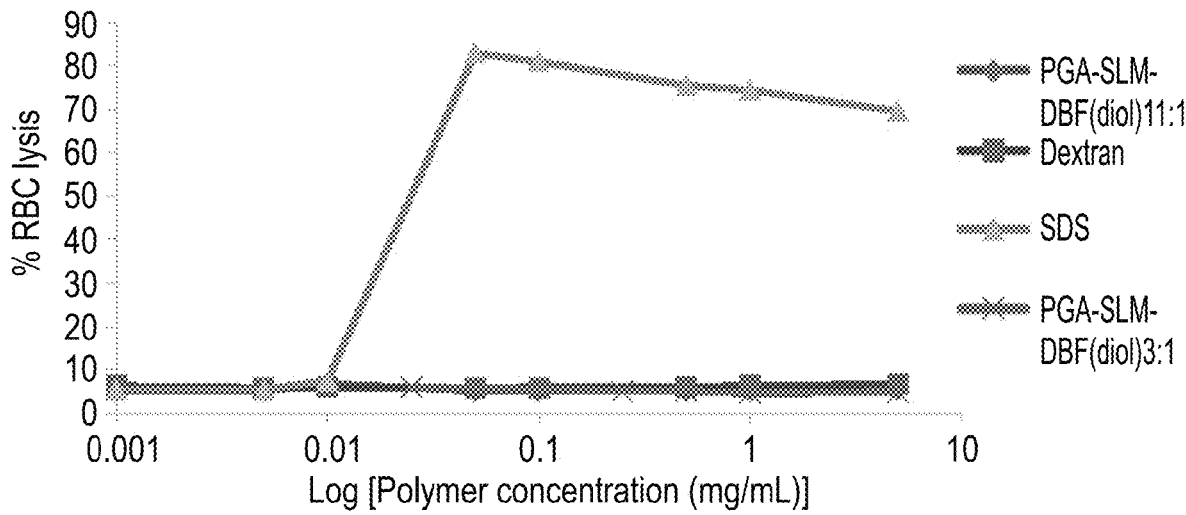

FIG. 6 presents data obtained in a lysis assay of PGA-SLM-DBFdiol (conjugates at 3:1 and 11:1 mol ratio on rat red blood cells.

Figure 7:
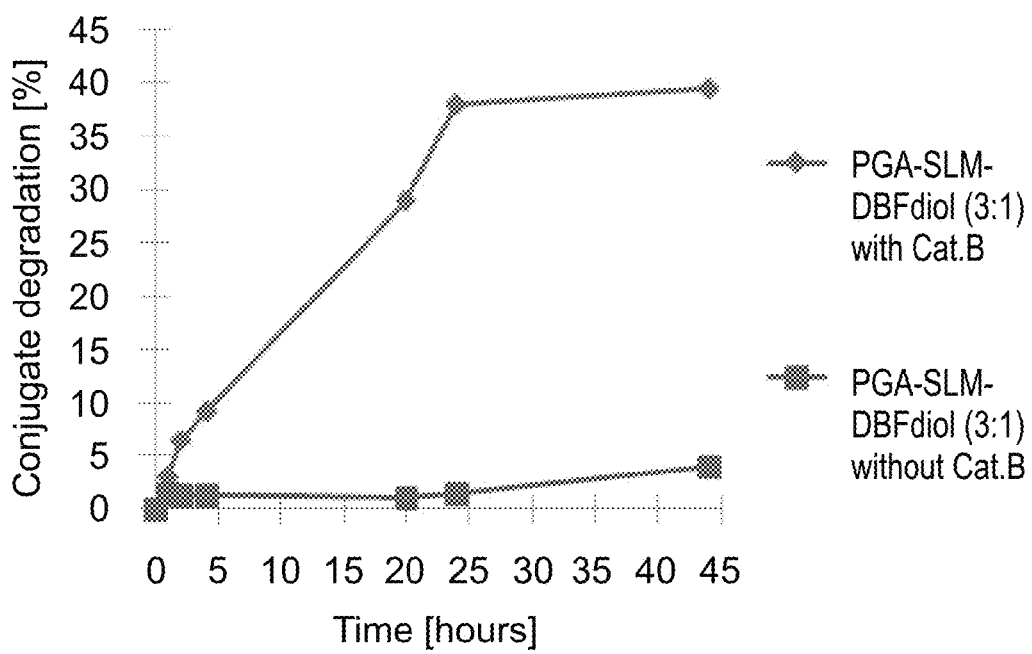

FIG. 7 presents comparative plots showing degradation of PGA-Selumetinib-Dabrafenib(diol)(3:1) at pH=5.5 in the presence (Blue) and absence (Red) of human Cathepsin B.

Figure 8:
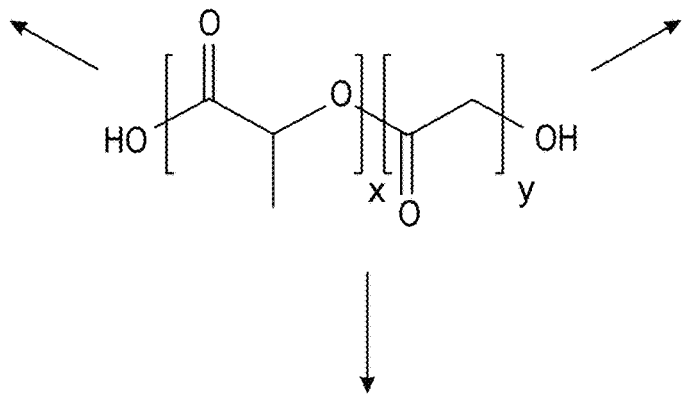

FIG. 8 presents a schematic illustration of PLGA backbone entrapping a combination of several drugs.

FIGS. 9A-B present environmental SEM images of PLGA-Nanoparticles (FIG. 9A) and Mannose-PLGA-Nanoparticles (FIG. 9B), prepared by Double emulsion-solvent evaporation (w/o/w) method.

Figure 10:
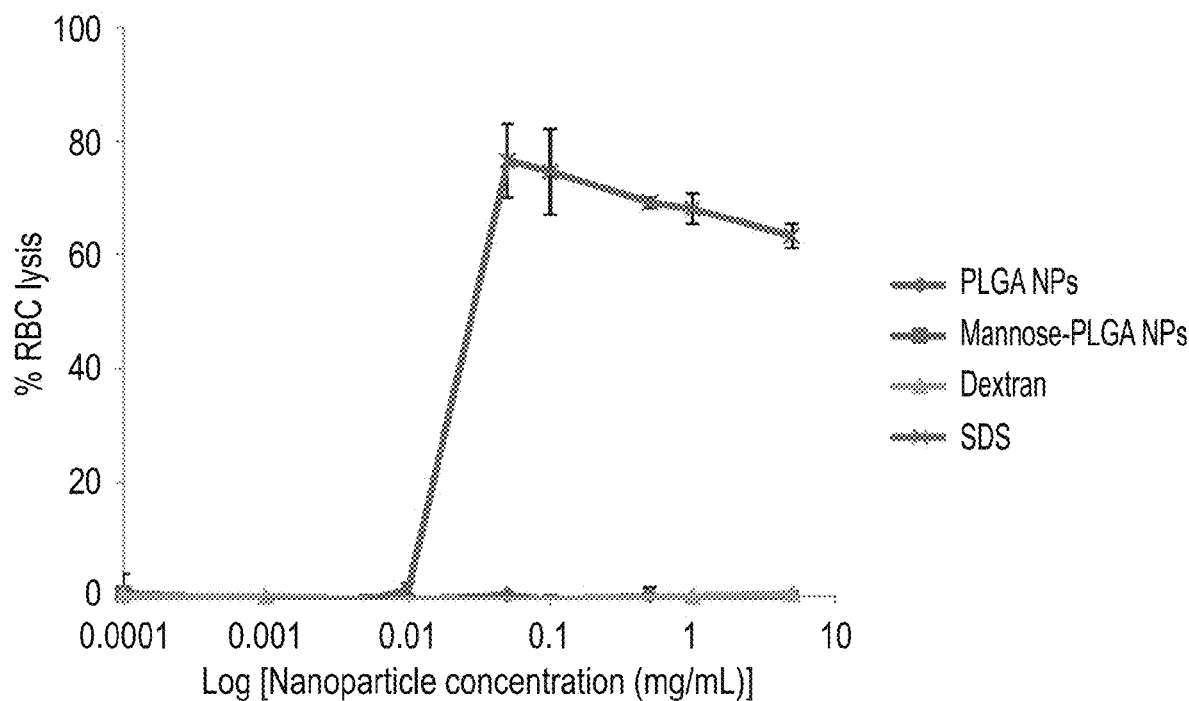

FIG. 10 presents data obtained in a lysis assay of PLGA-Nanoparticles and Mannose-PLGA-Nanoparticles on rat red blood cells.

Figure 11:
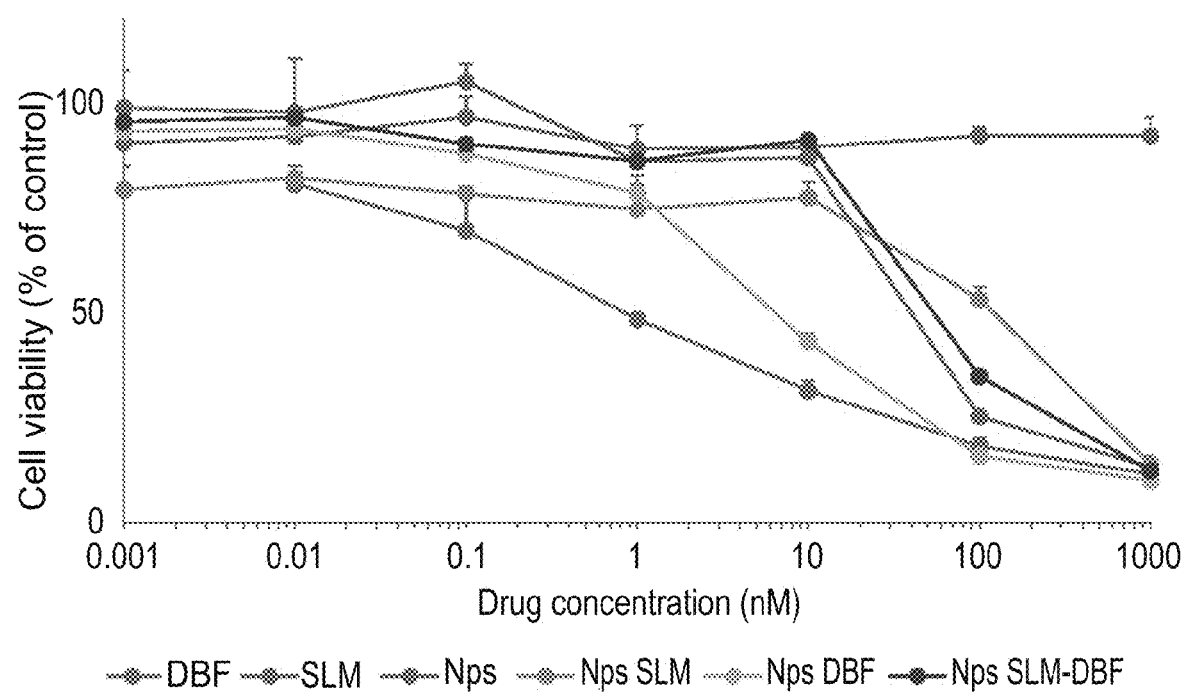

FIG. 11 presents comparative plots showing the anticancer activity of free dabrafenib, free selumetinib, PLGA-dabrafenib NPs, PLGA-selumetinib NPs and PLGA-dabrafenib-selumetinib NPs on human melanoma A375 cells.

Figure 12A:
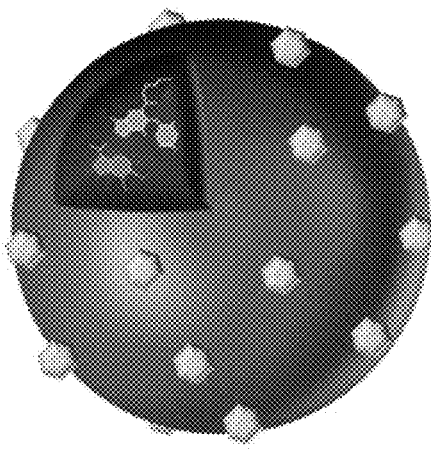
Figure 12B:
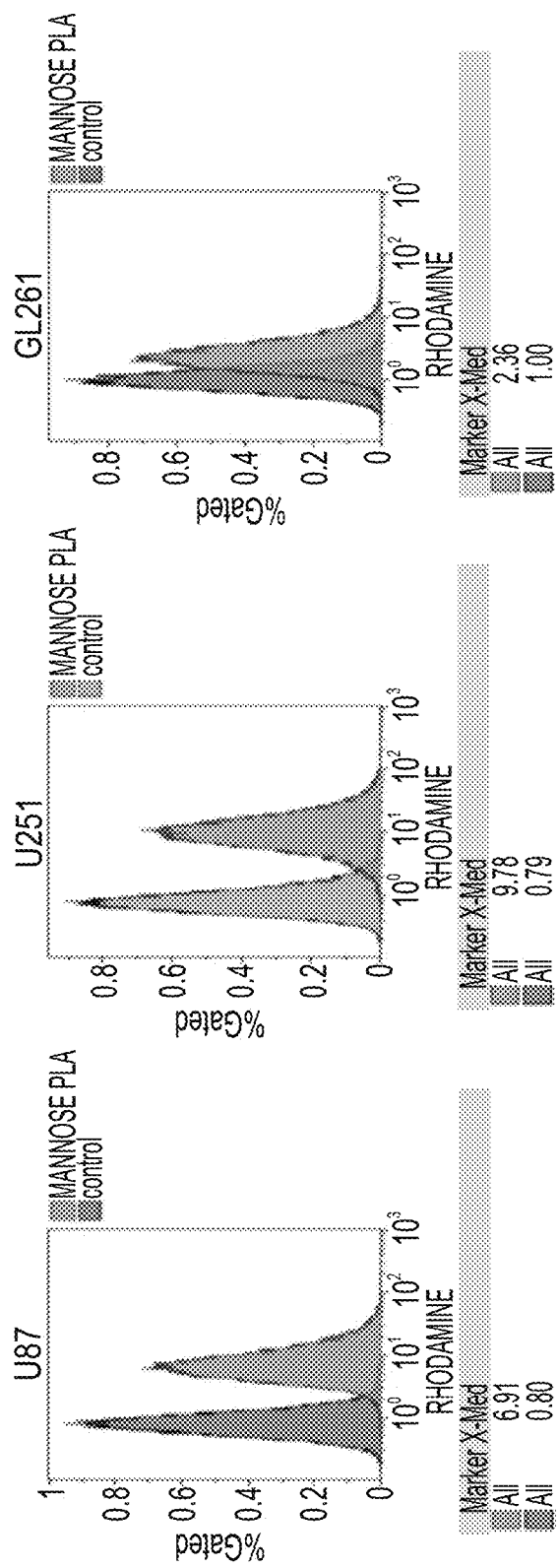

FIGS. 12A-B is a schematic representation of PLA/PLGA-mannose-NP encapsulating DBF and SLM (FIG. 12A) and FACS analysis of U87, U251 and GL261 cells incubated with labeled Mannose-PLGA (FIG. 12B).

Figure 13A:
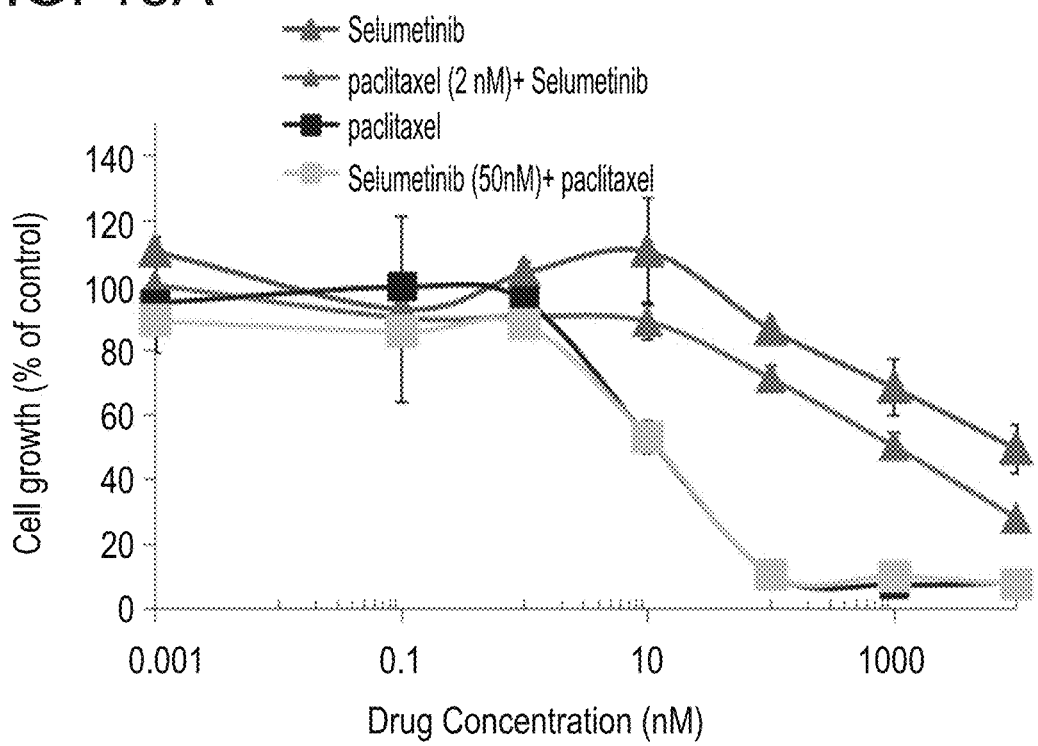
Figure 13B:
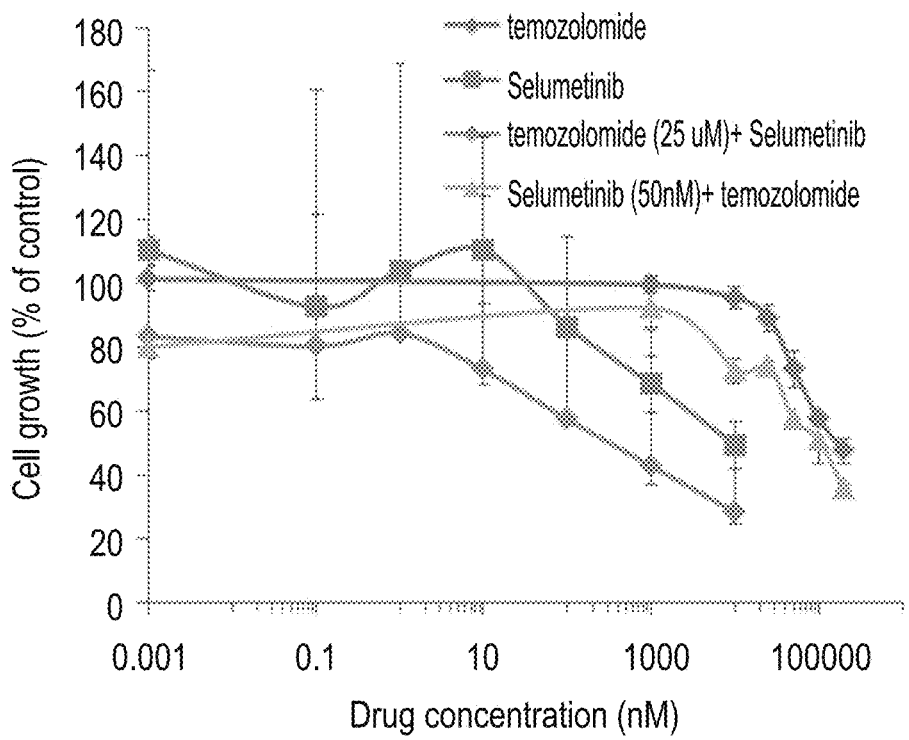

FIGS. 13A-B present comparative plots showing the effect of free selumetinib, Paclitaxel or both (FIG. 13A), or free selumetinib, temozolomide or both (FIG. 13B) on the proliferation of Ret-mCherry melanoma cells.

Figure 14:
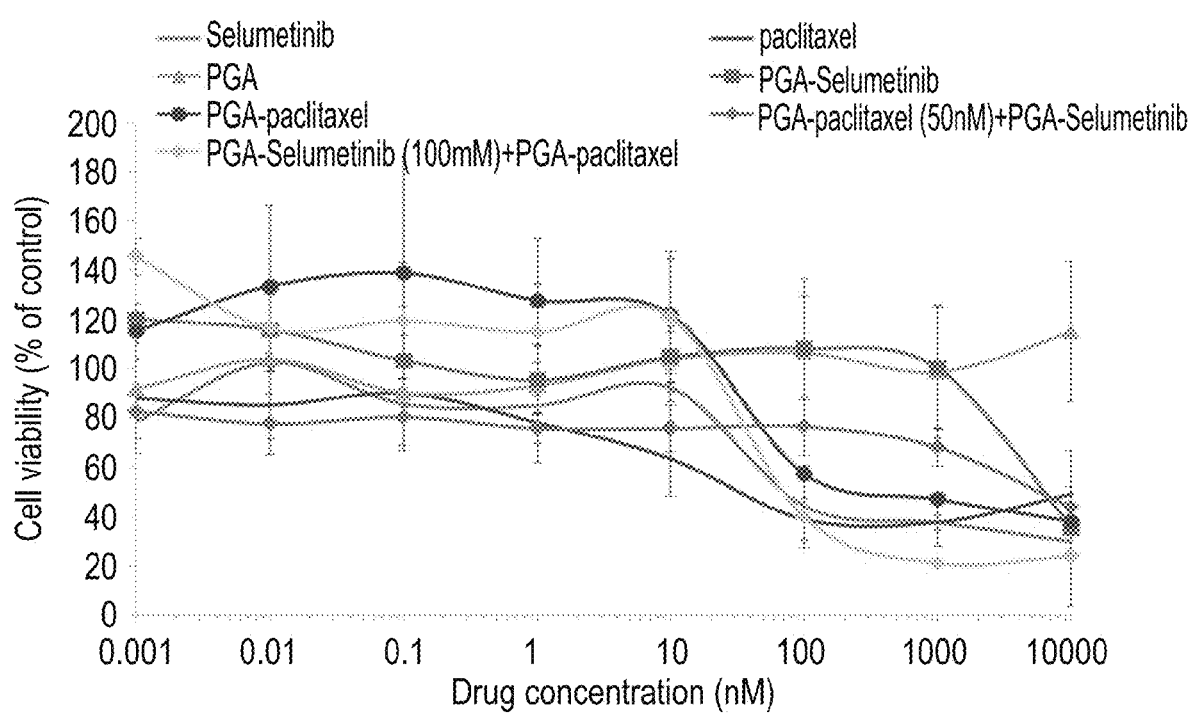

FIG. 14 presents comparative plots showing the effect of free selumetinib, PGA-Selumetinib, free Paclitaxel, PGA-paclitaxel or both on proliferation of A375 melanoma cells.

DESCRIPTION OF SPECIFIC EMBODIMENTS OF THE INVENTION

The present invention, in some embodiments thereof, relates to cancer therapy and, more particularly, but not exclusively, to polymeric matrices having associated therewith therapeutically active agent(s), and to uses thereof in treating various types of cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have conceived combining the advantageous EPR effect with the promising effect of agents that interfere with pathways involved in onset and progression of melanoma and have designed and practiced polymeric matrices containing one or more BRAF and/or MEK inhibitors while following the requirements of the EPR effect (e.g., shown in FIG. 1B), which penetrate almost exclusively into cancer tissue.

The present inventors have designed and successfully synthesized conjugates in which BRAF and/or MEK inhibitors are covalently linked to PGA or loaded into PLGA nanoparticles, have studied the influence of different linkers on drug biodistribution and drug release, and have characterized the physico-chemical and biological properties of the conjugates bearing a single drug or a combination of two drugs loaded at different ratios.

The present inventors have designed and successfully practiced PGA-modified dabrafenib, PGA-selumetinib, and PGA-selumetinib-modified dabrafenib conjugates, Nanoparticles-PLGA-dabrafenib, Nanoparticles-PLGA-selumetinib, and Nanoparticles-PLGA-selumetinib-dabrafenib and Mannose-Nanoparticles-PLGA-dabrafenib, Mannose-Nanoparticles-PLGA-selumetinib, and Mannose-Nanoparticles-PLGA-selumetinib-dabrafenib and have demonstrated that their combination resulted in a synergistic inhibition of melanoma cells proliferation and migration.

The present inventors have shown that the combination of free MEK inhibitor (e.g., selumetinib or trametinib or cobimetinib) and free BRAF inhibitor (e.g., dabrafenib or vemurafenib) has a synergistic inhibitory effect on melanoma cells proliferation and migration. See, FIGS. 3A and 3B.

Selumetinib, an ATP-independent inhibitor of mitogen-activated protein kinase (MEK or MAPK/ERK kinase) 1 and 2, that showed clinical efficacy in melanoma and NSCLC patients, was conjugated to PGA. The PGA-selumetinib demonstrated an inhibitory effect on human primary and metastatic melanoma cells proliferation and migration with an $IC_{50}$ value of 1-3 µM. See, FIGS. 4A and 4B (migration) and FIGS. 5A and 5B (proliferation). Nanoparticles-PLGA-selumetinib conjugate has an inhibitory effect on human primary melanoma cells proliferation with an $IC_{50}$ value of 50 nM. See, FIG. 11.

In addition, a PGA diol-modified-dabrafenib (DBFdiol) conjugate was demonstrated to exhibit an $IC_{50}$ value of 180 nM. See, FIGS. 5A and 5B. Nanoparticles-PLGA-dabrafenib exhibit $IC_{50}$ of 6 nM. See, FIG. 11.

Conjugates that bear a synergistic combination of dabrafenib and selumetinib on one polymeric backbone were also synthesized. It was found that the drugs are simultaneously released following cathepsin B cleavage, an overexpressed enzyme in inflammation and cancer in general and in melanoma in particular, allowing for their synergistic effect to occur. See, FIGS. 5A and 5B (synergistic activity on proliferation) and FIG. 7 (drug release).

Additional combinations were synthesized for the treatment of melanoma which does not bear the BRAF mutation. These include the combination of a MEK inhibitor with paclitaxel and temozolomide. See, FIGS. 13A, 13B and 14.

Embodiments of the present invention relate to polymeric conjugates comprising a polymeric matrix having associated therewith an agent that downregulates an activity or expression of a polypeptide associated with onset or progression of melanoma, and optionally and preferably, an additional agent that acts in synergy with said agent.

In some embodiments, the polymeric matrix is or comprises a polymeric backbone having the agent(s) covalently attached to the backbone units forming the polymeric backbone.

Embodiments of the present invention relate to polymeric conjugates comprising a polymeric backbone comprised of a plurality of backbone units, wherein a first portion of said backbone units has attached thereto an agent that downregulates an activity or expression of a polypeptide associated with onset or progression of melanoma, and optionally and preferably, a second portion of said backbone units has attached thereto an additional agent that acts in synergy with said agent.

In some of these embodiments, the conjugates are represented by Formula I, as described herein.

In some embodiments, the polymeric matrix is or comprises nanoparticles loaded with (physically entrapping or encapsulating or embedding) the one or more agent(s) as described herein.

Embodiments of the present invention relate to polymeric conjugates comprising a polymeric nanoparticle being in association (e.g., loaded with, embedding, encapsulating, entrapping) an agent that downregulates an activity or expression of a polypeptide associated with onset or progression of melanoma, and optionally and preferably, an additional agent that acts in synergy with said agent.

Embodiments of the present invention further relate to synthetic methodologies for preparing polymeric conjugates as described herein.

Embodiments of the present invention further relate to methods employing or uses of the conjugates in treating cancer treatable by downregulating expression and/or activity of the polypeptide. In some embodiments, the cancer is melanoma, for example, CNS-metastasizing melanoma. In some embodiments, the polypeptide is a mutated polypeptide (e.g., mutated BRAF) and the cancer is associated with the mutated polypeptide. In some embodiments, the cancer is a CNS-metastasizing cancer.

Polymeric Conjugates:

According to an aspect of some embodiments of the present invention there is provided a polymeric conjugate comprising a polymeric matrix having associated therewith an agent (a therapeutically active agent, a drug) that down-regulates an activity or expression of a polypeptide associated with onset or progression of melanoma, as defined herein.

In some embodiments, the polymeric matrix is or comprises a polymeric backbone having the agent(s) covalently attached to the backbone units forming the polymeric backbone.

According to an aspect of some embodiments of the present invention there is provided a polymeric conjugate comprising a polymeric backbone comprised of a plurality of backbone units, wherein a portion of the backbone units has an agent (a therapeutically active agent, a drug, a first agent) attached thereto, the agent being such that down-regulates an activity or expression of a polypeptide associated with onset or progression of melanoma.

Polymeric conjugates according to these embodiments are also referred to herein as "polymeric conjugates having a drug (or an agent) covalently attached to a polymeric backbone".

In some embodiments, the polymeric matrix is or comprises polymeric nanoparticles, as defined herein, and the agent that down-regulates an activity or expression of a polypeptide associated with onset or progression of melanoma is associated with the nanoparticles non-covalently, for example, by electrostatic interactions and/or by being encapsulated, embedded and/or entrapped in and/or on the nanoparticle.

Polymeric conjugates according to these embodiments are also referred to herein as "nanoparticles having a drug (or an agent) associated therewith".

By "polymeric conjugate" it is meant a conjugate formed between an agent as described herein and a polymeric matrix in which the agent is associated with the polymeric matrix by means of chemical (e.g., covalent, electrostatic) and/or physical (e.g., entrapment, encapsulation or absorbance) interactions.

In some embodiments, the polymeric conjugates described herein are advantageously characterized by one or more of the following:

As discussed hereinabove, the tumor vasculature possesses an enhanced capacity for the uptake of macromolecules and colloidal drug carriers having a high molecular weight and large hydrodynamic diameter due to the EPR effect. Therefore, a conjugate as described herein, having a large enough hydrodynamic diameter is beneficial. The term "large enough" is used herein to describe a conjugate having a hydrodynamic diameter which leads to an increase in the ratio of conjugate accumulated in the tumor tissue as compared to other tissues. The determination of the optimal ratio is well within the capability of those skilled in the art. For example, the ratio may be 1.1, 2, 3, 4, 5 etc. In some embodiments, the hydrodynamic diameter is in the range of from 3 nm to 500 nm.

The hydrodynamic diameter can be measured as described below under the Materials and Methods of the Example section which follows herein below.

In some embodiments, the polymeric conjugate is characterized by low mass distribution, that is, by a polydispersity index (PDI) Mw/Mn which is lower than 3, or lower than 2.5, or lower than 2, or lower than 1.5. The PDI can be determined by methods well known in the art. Exemplary methods are described in the Examples section that follows.

In some embodiments, the polymeric conjugate is characterized by zeta potential in the range of 0 to −100 mV.

The zeta potential can be determined by methods well known in the art. Exemplary methods are described in the Examples section that follows.

According to some of any of the embodiments described herein, the conjugates of the present embodiments may be administered or otherwise utilized, either as is, or as a pharmaceutically acceptable salt, enantiomer, diastereomer, solvate, hydrate or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

The phrase "pharmaceutically acceptable salts" is meant to encompass salts of the moieties and/or conjugates which are prepared with relatively nontoxic acids or bases, depending on the particular substituents found on the compounds described herein. When conjugates of the present invention contain relatively acidic functionalities, base addition salts can be obtained by contacting the neutral (i.e., non-ionized) form of such conjugates with a sufficient amount of the desired base, either neat or in a suitable inert solvent. Examples of pharmaceutically acceptable base addition salts include sodium, potassium, calcium, ammonium, organic amino, or magnesium salt, or a similar salt. When conjugates of the present invention contain relatively basic functionalities, acid addition salts can be obtained by contacting the neutral form of such conjugates with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific conjugates of the present invention contain both basic and acidic functionalities that allow the conjugates to be converted into either base or acid addition salts.

The neutral forms of the conjugates are preferably regenerated by contacting the salt with a base or acid and isolating the parent conjugate in a conventional manner. The parent form of the conjugate differs from the various salt forms in certain physical properties, such as solubility in polar solvents, but otherwise the salts are equivalent to the parent form of the conjugate for the purposes of the present invention.

In an example, a pharmaceutically acceptable salt of PGA is utilized. An exemplary such salt is a sodium salt.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

The conjugates described herein may possess asymmetric carbon atoms (optical centers) or double bonds; the racemates, diastereomers, geometric isomers and individual isomers are encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The conjugates described herein can exist in unsolvated forms as well as solvated forms, including hydrated forms. In general, the solvated forms are equivalent to unsolvated forms and are encompassed within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Certain conjugates of the present invention may exist in multiple crystalline or amorphous forms. In general, all physical forms are equivalent for the uses contemplated by the present invention and are intended to be within the scope of the present invention.

The Polymeric Matrix:

According to any of the embodiments described herein the phrase "polymeric matrix" describes a three-dimensional matrix which comprises, or substantially consists of (e.g., at least 50%, or at least 80%, or more) polymeric chains of one or more polymeric materials.

A polymeric matrix can be in a form of micelles, micro- or nano-spheres, micro- or nanoparticles, of entangled and/or cross-linked polymeric chains, and other forms.

As used herein throughout, the terms "polymer" or "polymeric material" or "polymeric substance" are used interchangeably and describe an organic substance composed of a plurality of repeating structural units (backbone units) covalently connected to one another. The term "polymer" as used herein encompasses organic and inorganic polymers and further encompasses one or more of a homopolymer, a copolymer or a mixture thereof (a blend). The term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone units can differ from one another by the pendant groups thereof.

Polymers which are suitable for use in the context of the present embodiments are biocompatible, non-immunogenic and non-toxic. The polymers serve as carriers that enable specific delivery into tumor tissue. As described hereinabove, the specific delivery is due to the enhanced permeability and retention (EPR) effect discussed hereinabove. Furthermore, conjugation to polymers may restrict the passage through the blood brain barrier and may prolong the circulating half-life of the drugs, hence inhibiting the growth of tumor endothelial and epithelial cells by exposing the cells to the conjugated drugs in the circulation for a longer time compared to the free drugs. Additionally, polymer-drug conjugates may act as drug depots for sustained release, producing prolonged drug exposure to tumor cells. Water-soluble polymers may be used to stabilize drugs, as well as to solubilize otherwise insoluble compounds such as, for example, Paclitaxel.

A polymeric material (e.g., polymer from which the polymeric backbone of a polymeric conjugate as described herein is derived, or corresponds to, as discussed herein), may be or may comprise a biostable polymer, a biodegradable polymer or a combination thereof.

The term "biostable", as used in this context of embodiments of the invention, describes a substance (a compound or a polymer) that remains intact under physiological conditions (e.g., is not degraded in vivo).

The term "biodegradable" describes a substance which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that at least 50 weight percents of the substance decompose within a time period shorter than one year.

The term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

The polymers can be water-soluble or water-insoluble. In some embodiments, the polymers are water soluble at room temperature.

The polymers can further be charged polymers or non-charged polymers. Charged polymers can be cationic polymers, having positively charged groups and a positive net charge at a physiological pH; or anionic polymers, having negatively charged groups and a negative net charge at a physiological pH. Non-charged polymers can have positively charged and negatively charged group with a neutral net charge at physiological pH, or can be non-charged.

In some embodiments, the polymer has an average molecular weight in the range of 100 Da to 800 kDa. In some embodiments, the polymer has an average molecular weight lower than 60 kDa. In some embodiments, the polymer's average molecular weight range is 15 to 60 kDa.

Polymeric substances that have a molecular weight higher than 10 kDa typically exhibit an EPR effect, as described herein, while polymeric substances that have a molecular weight of 100 kDa and higher have relatively long half-lives in plasma and an inefficient renal clearance. Accordingly, a molecular weight of a polymeric conjugate can be determined while considering the half-life in plasma, the renal clearance, and the accumulation in the tumor of the conjugate.

The molecular weight of the polymer can be controlled, at least to some extent, by the degree of polymerization (or co-polymerization).

The polymer used in the context of embodiments of the invention can be a synthetic polymer or a naturally-occurring polymer. In some embodiments, the polymer is a synthetic polymer.

Polymeric materials usable in the context of the present embodiments include, without limitation, polyacrylates, polyvinyls, polyamides, polyurethanes, polyimines, polysaccharides, polypeptides, polycarboxylates, and mixtures thereof.

Exemplary polymeric materials include, but are not limited to, polyglutamic acid (PGA), a poly(hydroxyalkylmethaacrylamide) (HPMA), a polylactic acid (PLA), a poly(lactic-co-glycolic acid) (PLGA), a poly(D,L-lactide-co-glycolide) (PLA/PLGA), a polyamidoamine (PAMAM), a polyethylenimine (PEI), dextran, pollulan, alginate, chitosan, polyglycerol, a water soluble polyamino acid, a polyethylenglycol (PEG) and co-polymers and mixtures thereof.

These polymers can be of any molecular weight, as described herein, and preferably have a molecular weight within the range of from 10 to 200 kDa, or from 10 to 60 kDa, or from 10 to 40 kDa.

Polymeric Conjugates Comprising a Polymeric Backbone Having a Drug Covalently Attached Thereto:

Some embodiments of the present invention relate to polymeric conjugates in which the polymeric matrix is or comprises a polymeric backbone comprised of a plurality of backbone units and having attached to a portion of these backbone units an agent as described herein (e.g., a drug).

This portion of backbone units is also referred to herein as a first portion, and the agent as a first agent.

By "portion" it is meant one, two or more backbone units, including all backbone units. In some embodiments, the "portion" is defined by the mol % of the backbone units in each portion, as detailed hereinafter.

The polymeric backbone of a polymeric conjugate according to these embodiments may be derived from, or correspond to, a polymeric backbone of polymers such as, for example, polyacrylates, polyvinyls, polyamides, polyurethanes, polyimines, polysaccharides, polypeptides, polycarboxylates, and mixtures thereof.

Exemplary polymeric backbones which are suitable for use in the context of the present embodiments are polymeric backbones which correspond to the polymeric backbones of polymers such as, but are not limited to, polyglutamic acid (PGA), a poly(hydroxyalkylmethaacrylamide) (HPMA), a polylactic acid (PLA), a poly(lactic-co-glycolic acid) (PLGA), a poly(D,L-lactide-co-glycolide) (PLA/PLGA), a polyamidoamine (PAMAM), a polyethylenimine (PEI), dextran, pollulan, alginate, chitosan, polyglycerol, a water soluble polyamino acid, a polyethylenglycol (PEG) and mixtures thereof.

These polymers can be of any molecular weight, as described herein, and preferably have a molecular weight within the range of from 10 to 200 kDa, or from 10 to 60 kDa, or from 10 to 40 kDa.

It is to be understood that the polymers as discussed herein describe those polymers that are formed from homogenic or heterogenic, non-functionalized monomeric units, and that the polymeric backbone constituting the polymeric conjugate according to these embodiments corresponds to such polymers by being comprised of the same monomeric units, while some of these monomeric backbone units have moieties/agents attached thereto, as described herein. Thus, the polymeric backbone of the polymeric conjugate is similar to that of the polymers described herein, and differs from the polymers by having the above-described agents attached to some of the backbone units therein.

In some of any of the embodiments described herein, the polymeric backbone is derived from, or corresponds to, polyglutamic acid (PGA).

PGA is a polymer composed of units of naturally occurring L-glutamic acid linked together through amide bonds. The pendant free γ-carboxyl group in each repeating unit of L-glutamic acid is negatively charged at a neutral pH, which renders the polymer water-soluble. The carboxyl groups also provide functionality for drug attachment. PGA is biodegradable and FDA-approved.

Cysteine proteases, particularly cathepsin B, play key roles in the lysosomal degradation of PGA to its nontoxic basic components, L-glutamic acid, D-glutamic acid and D,L-glutamic acid. The cellular uptake of negatively charged polymers can be hindered due to electrostatic repulsion forces between the polymers and the rather negatively charged surface of the cells. Although PGA is no exception to this rule, it does not diminish the EPR effect and the accumulation and retention of PGA-drug conjugates in solid tumors. Specific receptor-mediated interactions of PGA-drug conjugates containing targeting ligands may also increase the rate of polymer uptake into the target cells.

As used herein, "a polyglutamic acid" or "polyglutamic acid polymer" encompasses poly(L-glutamic acid), poly(D-glutamic acid), poly(D,L-glutamic acid), poly(L-gamma glutamic acid), poly(D-gamma glutamic acid) and poly(D, L-gamma glutamic acid).

PGA is usually prepared from poly(γ-benzyl-L-glutamate) by removing the benzyl protecting group with the use of hydrogen bromide. A sequential copolymer of protected PGA may be synthesized by peptide coupling reactions. For the preparation of high-molecular-weight homopolymers and block or random copolymers of protected PGA, triethylamine-initiated polymerization of the N-carboxyanhydride (NCA) of γ-benzyl-L-glutamate is used.

In some embodiments, the PGA is prepared essentially as described in further detail hereinafter, and demonstrated in the Examples section that follows (See, Example 1).

For any of the polymeric conjugates described herein, the plurality of the backbone units forming the polymeric backbone in the conjugate comprises two or more different portions of backbone units that differ from one another by the presence and/or nature of the moiety or agent covalently attached thereto. For example, one portion of the backbone units are "free" backbone units, and one portion of the backbone units have a therapeutically active agent (an agent as described herein, e.g., a first agent) covalently attached thereto. In another example, a third portion of the backbone units have another therapeutically active agent (an additional agent, e.g., a second agent, as described herein) covalently attached thereto, or a targeting moiety covalently attached thereto, or a labeling agent covalently attached thereto.

The different backbone units that have a moiety or agent attached thereto can be randomly dispersed within the polymeric backbone.

In some of any of the embodiments of the invention, a polymeric conjugate as described herein comprises a polymeric backbone comprised of a plurality of backbone units, whereby a portion of these backbone units have a therapeutically active agent (a first agent as described herein) covalently attached thereto. When the conjugate comprises two or more therapeutically active agents, the polymeric backbone is further comprised of other portions of the backbone units, each comprises a different therapeutically active agent covalently attached to the backbone units. When the polymer also comprises a targeting moiety, another portion of these backbone units have the targeting moiety covalently attached thereto. Those backbone units within the polymeric backbone that do not have a moiety covalently attached thereto are referred to herein as "free" or "non-functionalized" backbone units.

Thus, in some embodiments, a polymeric backbone as described herein is formed of a plurality of backbone units, which are covalently linked to one another so as to form the polymeric backbone. The backbone units are therefore such that, if not having certain moieties attached thereto, as described herein, form a polymeric backbone of a polymer. The plurality of backbone units as described herein, and the polymeric backbone comprised thereof, are therefore also defined herein as derived from, or corresponding to, the polymeric backbone of such a polymer. The plurality of backbone units as described herein, and the polymeric backbone comprised thereof, therefore correspond to, or are derived from, a polymer, whereby one or more moieties or agents, as described herein, are covalently attached to one or more portions of the backbone units. Since once the one or more moieties/agents are covalently attached to one or more portions of the backbone units forming the polymeric backbone, the backbone units forming the polymeric backbone are not identical to one another, as in the case of an "intact" polymer, and hence the polymeric conjugate is actually a copolymer, or has a copolymeric backbone, which is comprised of two or more types of backbone units. The phrase "polymeric backbone" as used herein therefore describes a "copolymeric backbone" comprised of at least two different types of backbone units.

It is to be noted that portions of the backbone units differ from one another by the presence/absence and/or type of the moiety or agent that are covalently attached to the backbone unit, but maintain the chemical structure of the portion of the backbone unit that forms the polymeric backbone. In analogy to a peptide, the portions of the backbone units differ from one another by the side chain of the amino acids. The portions of the backbone units thus differ from one another by the presence and/or nature of the pendant group thereof.

In some of any of the embodiments described herein, a polymeric conjugate as described herein comprises a polymeric (or copolymeric) backbone formed from a plurality of backbone units, and the plurality of backbone units comprise the following backbone units:

-A-, which represents a backbone unit within the polymeric backbone, or, in other words, a backbone unit of the polymer from which the polymeric backbone is derived, and is "free" of moieties that attached thereto, and one or more of the following backbone units:

-A-T1-, which represents a backbone unit of the polymer from which the polymeric backbone is derived (a backbone unit within the polymeric backbone), having a first agent as described herein (T1) covalently attached thereto;

-A-T2-, which represents a backbone unit of the polymer from which the polymeric backbone is derived (a backbone unit within the polymeric backbone), having an additional agent as described herein (T2) covalently attached thereto, the second therapeutically active agent being different from T1; and -A-L-, which represents a backbone unit of the polymer from which the polymeric backbone is derived (a backbone unit within the polymeric backbone), having a targeting moiety covalently attached thereto.

The backbone units can be arranged within the polymeric backbone in any order.

In some embodiments, the plurality of backbone units forming the polymeric backbone comprises the following portions of backbone units:

-(A)$_y$;
-(A-T1)$_x$-;
-(A-T2)$_z$-; and
-(A-L)$_n$,
wherein:

A is a backbone unit within the polymeric backbone, as described herein;

A-T1 is a backbone unit within the polymeric backbone having covalently attached thereto the first agent (T1), as described herein;

A-T2 is a backbone unit within the polymeric backbone having covalently attached thereto an additional agent (T2), as described herein;

A-L is a backbone unit within the polymeric backbone having covalently attached thereto a targeting moiety (L), as described herein;

y ranges from 50 to 99.9 mol percents, or from 70 to 99.9 mol percents;

x ranges from 0.1 to 50 mol percents, or from 0.1 to 20 mol percents;

z ranges from 0 to 50 mol percents, or from 0 to 20 mol percents; and n ranges from 0 to 20 mol percents.

In some of any of the embodiments described herein, the polymeric conjugate comprises a polymeric backbone comprised of a plurality of backbone monomeric units as described herein, the polymeric backbone being represented by Formula I as follows:

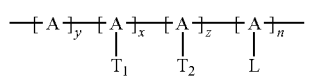

Formula I wherein:
A is a backbone unit forming said polymeric backbone;
T1 is the first agent (e.g. a MEK and/or BRAF inhibitor);
T2 is an additional agent (e.g., an additional MEK and/or BRAF inhibitor, or an additional agent such PTX or temozolomide or camptothecin);
L is a targeting moiety;
y ranges from 50 to 99.9 mol percents;
x ranges from 0.1 to 50, or 0.1 to 20 mol percent;
z ranges from 0 to 50 mol percent or from 0 to 20 mol percents; and
n ranges from 0 to 10 mol percent.

In some of these embodiments, the plurality of backbone units may comprise also -(A-T3)k- units. A "A-T3" unit is a backbone unit within the polymeric backbone that has covalently attached thereto a third therapeutically active agent, being different from T1 and T2. "k" ranges from 0.1 to 20 mol percent.

In some of any of the embodiments described herein for polymeric conjugates having covalently attached thereto one or more therapeutically active agents, the plurality of backbone units may further comprise backbone units to which a targeting moiety, as described herein, is attached, and which are referred to herein as -(A-L)n- backbone units.

In some of any of the embodiments described herein, a load of any of the therapeutically active agents, when present within the polymeric conjugate, denoted by "x", "z" or "k", ranges from 0.1 to 20 mol percent, or from 1 to 20 mol percent, and can be, for example, 0.1, 0.5, 1, 2, 3, 4, 5, 6, 7 8, 9, 10, 11, 12, 13, 14, 15, 16, 17, 18, 19 and 20, and even higher values, including any value therebetween.

In some of any of the embodiments described herein, the load of the targeting moiety, when different from 0, denoted as "n" in Formula I, ranges from 0.1 to 20 mol percent, or from 0.1 to 10 mol percent, or from 1 to 10 mol percent, and can be, for example, 0.1, 0.5, 1, 2, 3, 4, 5, 6, 7 8, 9, 10, 11, 12, 13, 14, 15, 16, 17, 18, 19 and 20, and even higher values, including any value therebetween.

The number of "free" backbone units, y, is in accordance with the load of the other moieties.

Herein, the phrases "loading onto the polymer", or simply "load", are used to describe the amount of an agent or moiety that is attached to the polymeric backbone of the conjugates described herein, and is represented herein by the mol percent (mol %) of this agent or moiety in the conjugate, as defined hereinafter.

Herein "mol percent" represents the number of moles of an attached moiety per 1 mol of the polymeric conjugate, multiplied by 100.

The % loading can be measured by methods well known by those skilled in the art, some of which are described hereinbelow under the Materials and Methods of the Examples section that follows.

The mol % of an agent or moiety corresponds to a mol % of the backbone units having this agent or moiety attached thereto.

In some of any of the embodiments described herein, the polymeric backbone is derived from PGA.

In each of the conjugates described in these embodiments, the therapeutically active agent(s) and/or the targeting moiety can each independently be linked to the respective portion of the backbone units in the polymeric backbone directly, or indirectly, through a linker moiety (also referred to herein as a linker, a linker group, a linking moiety or a linking group), whereby, in some embodiments, the direct/indirect linkage is designed as being cleavable at conditions characterizing the desired bodily site (e.g., by certain enzymes or pH), as detailed herein below.

Hence, according to some of any of the embodiments described herein, at least one of the therapeutically active agent(s) and/or the targeting moiety, if present, is attached to the respective backbone units via a linker. The linker linking each of the therapeutically active agent(s) to the polymer and the linker linking the targeting moiety to the polymer may be the same or different.

The linker described herein refers to a chemical moiety that serves to couple the targeting moiety and/or the therapeutically active agent(s) to the polymeric backbone (to the respective portion of backbone units) while not adversely affecting either the targeting function of the targeting moiety or the therapeutic effect of the targeting moiety and/or the therapeutically active agent(s).

In some embodiments, the linker is a biodegradable linker.

The phrase "biodegradable linker", as used herein, describes a linker that is capable of being degraded, or cleaved, when exposed to physiological conditions. Such physiological conditions can be, for example, pH, a certain enzyme, and the like. This phrase as is also referred to herein interchangeably as "biocleavable linker".

In some embodiments, the linker is designed as being cleavable at conditions characterizing the desired bodily site (e.g., by certain enzymes or pH), as detailed hereinbelow.

According to some embodiments, the biodegradable linker is a pH-sensitive linker, a hydrolysable linker or an enzymatically cleavable linker.

In some embodiments, the linker is capable of being cleaved by pre-selected cellular enzymes, for instance, those found in melanocytes or melanoma cells. Alternatively, an acid hydrolysable linker could comprise an ester or amide linkage.

In some embodiments the biodegradable linker is an enzymatically-cleavable linker. Such a linker is typically designed so as to include a chemical moiety, typically, but not exclusively, an amino acid sequence that is recognized by a pre-selected enzyme. Such an amino acid sequence is often referred to in the art as a "recognition motif". A conjugate comprising such a linker typically remains substantially intact in the absence of the pre-selected enzyme in its environment, and hence does not cleave or degrade so as to the release the agent attached thereto until contacted with the enzyme.

In some embodiments, the enzymatically cleavable linker is cleaved by an enzyme which is overexpressed in melanoma cells. A conjugate comprising such a linker ensures, for example, that a substantial amount of a conjugated therapeutically active agent is released from the conjugate only at the tumor tissue, thus reducing the side effects associated with non-selective administration of the drug and further enhancing the concentration of the drug at the tumor site.

An exemplary enzyme which is suitable for use in the context of these embodiments include, without limitation, Cathepsin B.

Suitable linkers include, but are not limited to, alkyl chains; alkyl chains optionally substituted with one or more substituents and in which one or more carbon atoms are optionally interrupted by a nitrogen, oxygen and/or sulfur heteroatom.

Other suitable linkers include amino acids and/or oligopeptides.

Such alkyl chains and/or oligopeptides can optionally be functionalized so as allow their covalent binding to the moieties linked thereby (e.g., the polymeric backbone and the targeting moiety, the polymer and the therapeutically active agent). Such a functionalization may include incorporation or generation of reactive groups that participate in such covalent bindings, as detailed herein under.

In some embodiment, the linker is a biodegradable oligopeptide which contains, for example, from 2 to 10 amino acid residues.

In some embodiments, the linker is a Cathepsin B-cleavable linker.

Cathepsin B is a lysosomal enzyme overexpressed in both epithelial and endothelial tumor cells. Suitable exemplary linkers having cathepsin-B cleavable sites include amino acid sequences such as, but are not limited to -[Cit-Val]- (SEQ ID NO:11), -[Arg]- (SEQ ID NO:21), -[Arg-Arg]- (SEQ ID NO:22), -[Phe-Lys]- (SEQ ID NO:12) -[Val-Arg]- (SEQ ID NO:13), -[Phe-Arg]- (SEQ ID NO:14), -[6-Glu-8-Asp]- (SEQ ID NO:23), -[Gly-Phe-Leu-Gly]- (SEQ ID NO:15), -[Gly-Phe-Ala-Leu]- (SEQ ID NO:16) and -[Ala-Leu-Ala-Leu]- (SEQ ID NO:17), -[Gly-Leu-Gly]- (SEQ ID NO:18), -[Gly-Phe-Gly]- (SEQ ID NO:19), -[Gly-Phe-Leu-Gly-Phe-Lys]- (SEQ ID NO:20) and combinations thereof.

An oligopeptide linker which contains the pre-selected amino acid sequence (recognition motif) can also be constructed such that the recognition motif is repeated several times within the linker, to thereby enhance the selective release of the attached agent. Various recognition motifs of the same or different enzymes can also be incorporated within the linker. Similarly, the linker may comprise multiple pH sensitive bonds or moieties. Linkers comprising such multiple cleavable sites can enhance the selective release of the therapeutically active agent at the desired bodily site, thereby reducing adverse side effects, and further enhance the relative concentration of the released drug at the bodily site when it exhibits its activity.

In cases where the targeting moiety and/or the therapeutically active agent(s) is/are bound directly to the polymeric backbone, the bond linking these moieties can also be biodegradable, for example, a hydrolysable bond, an enzymatically-cleavable bond or a pH-sensitive bond. Such a bond can be formed upon functionalizing the polymeric backbone, the targeting moiety and/or the therapeutically active agent, so as to include compatible reactive groups, as defined herein, for forming the required bond.

According to some embodiments, the biodegradable linker is a pH-sensitive linker or an enzymatically-cleavable linker.

A pH-sensitive linker comprises a chemical moiety that is cleaved or degraded only when subjected to a certain pH condition, such as acidic pH (e.g., lower than 7), neutral pH (6.5-7) or basic pH (higher than 7).

Such a linker may, for example, be designed to undergo hydrolysis under acidic or basic conditions, and thus, the conjugate remains intact and does not release the agents attached to the polymer in the body, until it reaches a physiological environment where a pH is either acidic or basic, respectively.

Exemplary pH-sensitive linkers include, but are not limited to, a hydrazone bond, a hydrazine-containing linker, ester (including orthoester) bond, amide bond of cis-aconytil residue, a trityl group, acetals, ketals, Gly-ester and a -[Gly-Phe-Gly]- moiety.

The peptide linker may also include a peptide sequence which serves to increase the length of the linker. Longer peptides may be advantageous due to a more efficient steric interaction of the linker with the cleaving enzyme due to enhanced accessibility.

Other linkers are described in the Examples section that follows.

In some embodiments, when one of the therapeutically active agents covalently attached to the backbone unit is paclitaxel, it is attached to a backbone unit within the polymeric backbone via a hydrolysable linker (e.g., an ester bond or a linker that comprises an ester bond), which can be, for example, cleavable by hydrolases.

In some embodiments a therapeutically active agent and/or targeting moiety is linked to the polymeric backbone or to the linker via a spacer. In some embodiments the therapeutically active agent is linked to the polymeric backbone or to the linker via a spacer. The spacers can be the same or different.

The term "spacer" as used herein describes a chemical moiety that is covalently attached to, and interposed between, the polymeric backbone and the linker, or the targeting moiety/therapeutically active agent, thereby forming a bridge-like structure between the polymeric backbone and/or the targeting moiety/therapeutically active agent. Alternatively, the spacer may be covalently attached to, and interposed between, the linker and the therapeutically active agent and/or the targeting moiety.

Hence, according to some embodiments at least one of the therapeutically active agent(s) and the targeting moiety is attached to the polymeric backbone and/or to the linker via a spacer.

Suitable spacers include, but are not limited to, alkylene chains, optionally substituted by one or more substituents and which are optionally interrupted by one or more nitrogen, oxygen and/or sulfur heteroatom.

Other suitable spacers include amino acids and amino acid sequences, optionally functionalized with one or more reactive groups for being coupled to the polymeric backbone/targeting moiety/therapeutically active agent/linkers.

In some embodiments, the spacer has the formula G-(CH$_2$)n-K, wherein n is an integer from 1 to 10; and G and K are each a reactive group such as, for example, NH, O or S. In some embodiments, G and K are each NH and n is 2.

An exemplary spacer is —[NH—(CH$_2$)$_m$NH$_2$]— wherein "m" stands for an integer ranging from 1-10. Preferably m is 2.

In some embodiments, the spacer is an amino acid sequence, optionally an inert amino acid sequence (namely, does not affect the affinity or selectivity of the conjugate). Such a spacer can be utilized for elongating or functionalizing the linker.

Exemplary such sequences include, for example, -[Gly-Gly-] and —[Phe-Lys]-.

In some cases, a spacer is utilized for enabling a more efficient and simpler attachment of the targeting moiety and/or therapeutically active agent to the polymeric backbone or linker, in terms of steric considerations (renders the site of the polymer to which coupling is effected less hindered) or chemical reactivity considerations (adds a compatible reactive group to the site of the polymer to which coupling is effected). In some cases, the spacer may contribute to the performance of the resulting conjugate. For example, the spacer may render an enzymatically cleavable spacer less sterically hindered and hence more susceptible to enzymatic interactions.

In some embodiments, the spacer facilitates the attachment of the moiety or agent to the polymeric backbone or the linker. This may be effected by imparting a reactive group to the moiety to be attached, which is chemically compatible with functional groups in the polymeric backbone and/or the linker attached to the polymeric backbone, and/or by modifying the solubility of the moiety to be attached to the polymer, so as to facilitate the reaction between the polymer (or co-polymer) and the moiety.

In some embodiments, the spacer is a degradable spacer, which is capable of undergoing degradation reactions so as to release the agent attached thereto. In some embodiments, the spacer is biodegradable, as defined herein.

A spacer may also be used in order to attach other agents (e.g., a labeling agent, as described hereinbelow) to the conjugate.

The spacer may be varied in length and in composition, depending on steric consideration and may be used to space the angiogenesis targeting moiety and/or therapeutically active agent form the polymeric backbone.

In some embodiments the spacer is a substituted or unsubstituted aryl group and substituted or unsubstituted heteroaryl group whereby the substituents can be carbonate, C-amido, N-amido and amine, whereby the spacer may be linked to the first and/or additional agent/targeting moiety/linker/polymer either directly, through the aromatic group or alternatively, via one or more of the substituents.

In some embodiments, the spacer is a degradable spacer selected such that it undergoes a spontaneous degradation once it is cleaved from the polymeric conjugate.

In some embodiments, the spacer is a degradable spacer selected such that it undergoes a spontaneous degradation once it is cleaved from the polymeric conjugate.

Such a spacer can be, for example, attached to a biodegradable linker at one end and to a therapeutically active agent (e.g., a first agent or an additional agent) or a targeting moiety at another end, such that once the biodegradable linker is cleaved, so as to release the spacer and the moiety attached thereto, the spacer undergoes a spontaneous degradation so as to release the moiety attached thereto.

Exemplary spacers that can undergo such a spontaneous degradation include, but are not limited, chemical moieties that can undergo a spontaneous 1,4-, 1,6-, 1,8-, etc. elimination, via a cascade of immolative electronic reactions. Such chemical groups are known in the art, or, otherwise, can be devised by those skilled in the art.

In an exemplary embodiment, the spacer is such that can undergo a spontaneous 1,6-benzyl elimination. An example of such a spacer is p-aminobenzyl carbonate (PABC). Such a spacer can be used, for example to attach paclitaxel to PGA-derived backbone units, and is obtained by conjugating PTX with p-aminobenzyl alcohol (PABA). Such a spacer results in forming an ester bond between PTX and the polymer.

The spacer may be varied in length and in composition, depending on steric consideration and may be used to space the anti-angiogenic agent and/or bone targeting moiety form the polymeric backbone.

Exemplary conjugates according to the present embodiments can be represented by the following formulae:

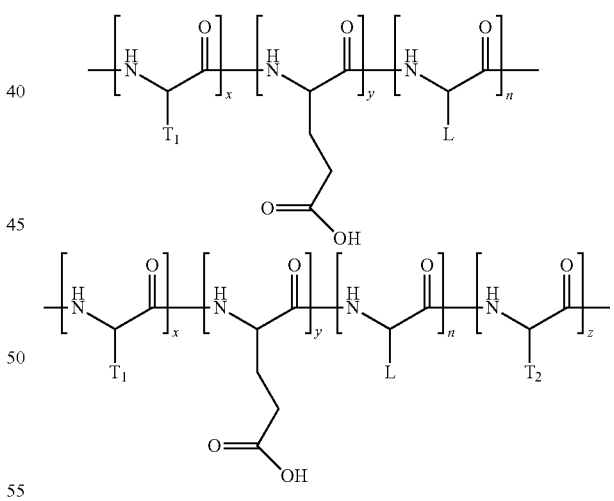

with T1, T2, L, x, y, z and n are as described herein.

Each of the polymeric conjugates described herein may further comprise a labeling agent, as described herein, attached to the polymeric backbone. The labeling agent can be attached to the N-terminus of the polymeric backbone, either directly, or by means of a spacer, as described herein. Alternatively, the labeling agent can be attached to a portion of the backbone units forming the polymeric backbone, directly or via a spacer, such that the plurality of backbone units forming the polymeric backbone further comprises units of the type -[A-P]m, whereas:

P is the labeling moiety;

A-P is a backbone unit having the labeling moiety attached thereto; and m ranges from 0.1 to 10 mol percent.

In some embodiments, the labeling agent can be attached to any of the therapeutically active agent(s) and/or targeting moieties attached to the polymeric backbone. For example, the labeling agent can be attached to a targeting moiety which is a peptide, as described herein.

Further according to embodiments of the present invention there are provided processes of preparing any of the conjugates described herein, having the agent (drug) covalently attached to a polymeric backbone.

Conjugates can be prepared by attaching the agents/moieties to the backbone units of already polymerized monomers or by attaching each of the agents/moieties to monomeric units and then polymerizing the monomeric units, or by any combination of the above.

Exemplary processes are presented in the Examples section that follows.

In some embodiments, the process comprises coupling the agent(s) to the polymer from which the polymeric backbone is derived, or to which the polymeric backbone corresponds.

In some embodiments, the process further comprises, prior to the coupling, preparing the polymer, typically by polymerizing a plurality of monomers that form the polymeric backbone.

In general, the polymerization technique is selected so as to allow controlling the degree of polymerization and/or the load of the moieties that are attached to the backbone.

Exemplary techniques include NCA ring-opening polymerization, which is suitable for PGA polymeric backbones.

As discussed in detail in the Examples section that follows, the present inventors have devised and practiced a process of preparing PGA which allows improved control over the polymer's properties (e.g., Mw, Mn, Mz, PDI and/or degree of polymerization).

Embodiments of the present invention therefore relate to a novel process of preparing PGA.

In some embodiments, preparing PGA comprises polymerizing a plurality of monomers, each of said monomers being N-carboxyanhydride (NCA) of γ-benzyl-L-glutamate.

In some embodiments, the polymerization is performed in the presence of an initiator. While any initiator commonly used in NCA ring-opening polymerization is contemplated, the present inventors have prepared and utilized an initiator which is an ammonium salt of tetrafluoroboric acid.

A process as described herein, in some embodiments, comprises polymerizing a plurality of (optionally carboxy-protected) NCA of L-glutamate (e.g., N-carboxyanhydride of γ-benzyl-L-glutamate) monomers, in the presence of an ammonium salt of tetrafluoroboric acid.

In some embodiments, the ammonium salt of tetrafluoroboric acid is an alkylammonium salt, and in some of these embodiments, the alkyl is of 1 to 20, or of 1-15, or of 1-12, or of 1-10 carbon atoms in length. In some embodiments, the alkyl is a branched alkyl. In some embodiments, the alkyl is neopentyl.

In some embodiments, a process of preparing a conjugate as described herein comprises coupling the first agent, and optionally the additional agent, if present, to a polymer corresponding to the polymeric backbone. Exemplary coupling methodologies and agents are described in the Examples section.

In some embodiments, the coupling is effected so as to form an ester bond (e.g., between a carboxylate group of the polymer and a hydroxy group of the agent), or an amide bond (e.g., between a carboxylate group of the polymer and an amine group of the agent).

Any coupling agent known as usable for forming esters or amide bonds, including, for example, coupling agents known as usable in forming peptide bonds, are contemplated. An exemplary usable coupling agent is BOP-Cl.

In some embodiments, the coupling is effected so as to form a hydrazine-containing or hydrazone-containing bond, by means of suitable linkers and/or spacers containing such bonds.

In some embodiments, the process further comprises, prior to the coupling, preparing the first agent or the additional agent, by modifying a known agent so as to facilitate its coupling to the polymeric backbone, to thereby obtain a structural analog of the agent, as described in further detail hereinafter.

Modifying the agent can be effected by generating a reactive group that is chemically compatible with a reactive group of the polymer (e.g., a reactive group present in the pendant groups of the polymer). Such a modification include, for example, converting a functional group (e.g., a substituent) of the agent (drug), which is not sufficiently reactive towards the coupling (e.g., is not chemically compatible with a reactive group of the polymer), to a reactive group as described herein (e.g., hydroxy or amine or diol or ketone or hydrazine).

Alternatively, or in addition, modifying the agent can be effected by attaching to the agent a moiety that comprises (e.g., terminates with) a reactive group as described herein.

Exemplary reactive groups that are usable in coupling to PGA, that is, that are chemically compatible with a carboxylate, include, but are not limited to, hydroxy, alkoxy, diol, amine, hydrazine, acyl, carbonyl (ketone) and any other group that can form a bond with a carboxylate.

In some embodiments, the reactive group generated on the agent is selected such that the bond formed with the reactive group of the polymer is a biodegradable bond, as described herein. Exemplary such bonds include, for example, hydrolysable bonds such as ester bonds, and pH sensitive bonds such as hydrazone-containing bonds.

Exemplary modified agents (structural analogs) are described hereinafter and are exemplified in the Examples section that follows.

Modified Therapeutically Active Agents:

According to an aspect of some embodiments of the present invention there is provided a structural analog of an agent that down-regulates activity or expression of a polypeptide associated with onset of progression of melanoma, the analog comprising a reactive group usable in coupling the agent to the polymeric backbone as described herein. Exemplary such analogs are described in the Examples section that follows.

By "structural analog" of a compound or agent it is meant a derivative of the compound (agent) which has a skeleton structure substantially the same as the compound or agent, yet one or more groups, preferably substituents of one or more positions of the skeleton structure, is/are replaced by another substituent(s), while retaining the biological activity of the compound. In some embodiments, the replacing substituent is or comprises a reactive group as described herein.

The structural analogs described herein are therefore characterized as exhibiting a biological activity which is substantially the same as that of the original compound. By "substantially the same" it is meant, for example, exhibiting an IC$_{50}$ under the same experimental condition which is ±20%, or ±10% or ±5% the IC$_{50}$ of the original compound or agent.

The structural analogs are also referred to herein as "modified" with respect to the parent compound, or as modified therapeutically active agents or drugs. The nature of the modification, for example, the added reactive group, is indicated either as "reactive group"-modified agent, or as an agent ("reactive group"). For example, when an agent is modified so as to feature an amine group not present in its inherent structure, it is also referred to herein an amine-modified agent or as an agent (amine).

In some embodiments, the reactive group is usable in coupling the agent to a chemically compatible reactive group of a polymer corresponding to the polymeric backbone, as described herein.

Exemplary structural analogs according to the present embodiments are presented in Schemes 9, 10 and 11 in the Examples section that follows.

Nanoparticles Having a Drug Associated Therewith:

According to some embodiments of the present invention, the polymeric conjugate comprises a polymeric matrix in association with a first agent as described herein, such that the drug (the therapeutically active agent, e.g., an agent as described herein) is in association with a polymer as described herein, or a polymeric matrix made of a polymer as described herein.

In some of these embodiments, the association is via electrostatic interactions.

In some embodiments, the association is via a physical association, and the agents (the first agent an optionally an additional agent as described herein) can be embedded, entrapped or encapsulated in a polymeric matrix (e.g., polymeric particles such as nanoparticles) or absorbed to a polymeric matrix.

In some embodiments, the polymeric matrix comprises a plurality of particles, for example, nanoparticles.

The nanoparticles can be of any shape, and are preferably characterized by at least one dimension (e.g., a diameter, or length) that ranges from 0.1 to 900 nm, or from 0.1 to 500 nm, or from 1 nm to 300 nm.

As demonstrated in the Examples section that follows, nanoparticles having at least one dimension that ranges from 1 to 100 nm can also be obtained.

In some of these embodiments, the conjugate comprises polymeric nanoparticles entrapping therein the first and optionally an additional agent, as described herein.

In some embodiments, the polymeric matrix comprises a plurality of particles (e.g., nanoparticles) and the first agent is associated with a first portion of said particles.

In some embodiments, the polymeric conjugate further comprises an additional agent as described herein, and the additional agent is associated with a second portion of said particles.

In some embodiments, the first agent and the additional agent are associated with the same particle, or the same portion of particles (e.g., the first portion).

In some embodiments, the nanoparticles are made of a polymeric material that is or comprises PLGA (see, for example, FIG. 8 and Example 5). Exemplary nanoparticles comprise PLGA and PLA, and may optionally further comprise a PLGA-PEG copolymer (e.g., block copolymer).

In some embodiments, the nanoparticles feature a targeting moiety attached to the surface thereof. The targeting moiety can be covalently attached to the polymeric material or be otherwise associated with the nanoparticles surface (e.g., by electrostatic interactions, or by absorption).

Any of the targeting moieties described herein is contemplated in these embodiments.

In some embodiments, the targeting moiety is mannose.

Nanoparticles encapsulating or entrapping therein the agent(s) as described herein can be prepared by any of the methods known in the art for preparing polymeric particles.

In some embodiments, there are provided processes of preparing nanoparticles entrapping the first agent, and optionally an additional agent, as described herein.

An exemplary method involves an emulsion-solvent removal technique, such as, for example, double emulsion-solvent evaporation (w/o/w) technique, in which an organic solution comprising the polymeric substance is emulsified once or twice with an aqueous solution. The agent is added to the organic and/or aqueous solution, depending on its solubility. Emulsification can be performed by any technique known in the art, e.g. probe sonicator.

Another exemplary method involves a use of a microfluidic chip to which an organic solution containing the polymeric substance and the agent(s) and an aqueous solution are added.

When the particles comprise a targeting moiety attached thereto, the targeting moiety can be attached to the polymeric particle or to a polymer from which the nanoparticle is prepared, prior to its preparation.

Targeting Moieties:

In some of any of the embodiments described herein, the polymeric matrix further comprises a targeting moiety associated therewith (e.g., covalently attached thereto).

Herein, a targeting moiety is a moiety, which is typically derived from a compound that exhibits high affinity to polypeptides that are expressed on the surface of tumor cells or in the microenvironment of tumor cells (e.g., endothelial cells).

In some of any of the embodiments described herein, the targeting moiety is a ligand of a cell-surface receptor that is expressed in tumor cells and/or endothelial cells.

In some of any of the embodiments described herein, the targeting moiety is a ligand of a cell-surface receptor that is expressed in endothelial cells, e.g., proliferating endothelial cells.

In some embodiments, the targeting moiety is an angiogenesis targeting moiety. The phrase "angiogenesis targeting moiety" describes a chemical moiety that can bind to a location in a mammal in which neovascularization, such as neovascularization of tumor cells, occurs (e.g., can bind to an angiogenesis-associated receptor). The phrase "neovascularization" is meant to encompass two unique processes: vasculogenesis, the de novo assembly of blood vessels, and angiogenesis, the formation of new capillary sprouts from pre-existing vessels.

The angiogenesis targeting moiety described herein is derived from compounds that can selectively bind to a location in a mammal in which neovascularization occurs and hence may serve to deliver the conjugate described herein to the desired location.

In some embodiments the targeting moiety is capable of binding to an angiogenesis-associated integrin as a cell-surface receptor expressed in proliferating endothelial cells. In some embodiments, the targeting moiety targets the $\alpha_v\beta_3$ integrin receptor.

The $\alpha_v\beta_3$ integrin is overexpressed on proliferating endothelial cells such as those present in growing tumors, as well as on some tumor cells of various origins. The RGD sequence represents the minimal amino acid domain, in several extracellular matrix proteins, which has been demonstrated to be the binding site of the transmembrane integrins proteins family [Bazzoni et al. 1999, *Current Opinion in Cell Biology*; (11) pp. 573-581].

Accordingly, in some embodiments, the angiogenesis targeting moiety comprises at least one Arg-Gly-Asp (RGD; SEQ ID NO:7) moiety, or a peptidomimetic thereof (e.g. E-[c(RGDfK)$_2$]; SEQ ID NO:10), and can optionally further include other amino acids, amino acid derivatives, or other chemical groups (e.g., alkylene chains).

In some embodiments, the RGD-containing moiety is an oligopeptide. The oligopeptide can be a cyclic oligopeptide (including, for example, monocyclic, bicyclic and tricyclic oligopeptides) or a linear oligopeptide, and can include, in addition to the Arg-Gly-Asp amino acid sequence, from 1 to 10 amino acids.

It has been further found that the substrate specificity of RGD-containing moieties results from the different conformations of the RGD sequence in different matrix proteins.

In an embodiment, the oligopeptide is a cyclic peptide comprising a c[Arg-Gly-Asp-Phe-Lys] amino acid sequence (SEQ ID NO:8).

In some embodiments, the angiogenesis targeting moiety comprises two or more Arg-Gly-Asp-containing moieties, wherein the moieties can be the same or different.

Exemplary Arg-Gly-Asp-containing moieties that are suitable for use in the context of embodiments of the invention include, but are not limited to c(RGDfk) (SEQ ID NO:8), RGD4C (SEQ ID NO:9), E-[c(RGDfK)$_2$] (SEQ ID NO:10) and other RGD-containing cyclic peptides such as those described in Haubner et al. [*J. Am. Chem. Soc.* 1996, 118, 7881-7891] and Capello, et al. [*J. Nucl. Med.* 2004, 45(10), 1716-20] and in WO 97/06791 and U.S. Pat. No. 5,773,412. Exemplary effective RGD cyclic peptides are the Arg-Gly-Asp (RGD) cyclic pentapeptides in which two amino acids such as D-tyrosine and lysine were added to the RGD and the pentapeptide was transformed into cyclic pentapeptide.

In some embodiments, the RGD-containing moiety can comprise two or more -Arg-Gly-Asp-moieties, being either linked to one another or being spaced by one or more amino acids or any other spacer, as defined herein.

In some embodiments, the targeting moiety is such that exhibits high affinity to P-selectin, which is expressed in melanoma, glioblastoma and other cancer cells. An exemplary such targeting moiety is a monosaccharide such as mannose.

In some embodiments, the cell-surface receptor is NCAM and the targeting moiety is NCAM targeting moiety.

In some embodiments, the NCAM targeting moiety is a ligand of the NCAM receptor, and, in some embodiments, it is a ligand that is specific to NCAM receptor.

In some embodiments, the ligand of NCAM is a peptide. Such peptides are referred to herein and in the art as NCAM-targeting peptides or abbreviated as NTP.

In some embodiments, the peptide comprises the amino acid sequence DDSDEEN (SEQ ID NO:5), which is known to target NCAM. In some of these embodiments, the NTP may further comprise one or more amino acid residues, at each terminus thereof, which may serve, for example, to facilitate attachment to the polymeric backbone and/or to improve its targeting by improved exposure (reduced stearic hindrance by the polymer). In some embodiments, the NCAM targeting peptide is of the 8-amino acid sequence GDDSDEEN (SEQ ID NO:1).

In some embodiments, the NCAM targeting peptide comprises an amino acid sequence of the C3 peptide, ASKKPKRNIKA (SEQ ID NO:6). In some of these embodiments, the peptide may further comprise one or more amino acid residues, at each terminus thereof, which may serve, for example, to facilitate attachment to the polymeric backbone and/or to improve its targeting by improved exposure (reduced stearic hindrance by the polymer). In some embodiments, the NCAM targeting peptide is of the sequence GASKKPKRNIKA (SEQ ID NO:3), with added glycine spacer at the N-terminal.

In some embodiments, the targeting moiety is an RGD-containing moiety, and is usable (has a high affinity) for tumor endothelial cells and also for tumor cells like breast cancer, melanoma and glioblastoma.

In some embodiments, the targeting moiety is an NCAM targeting peptide or Antibody and is usable (has high affinity) for NCAM which is overexpressed on tumor endothelial cells, and/or tumor cells of, for example, neuroblastoma, glioblastoma, melanoma, Wilms' tumor, renal cell carcinoma.

In some embodiments, the targeting moiety is a P-selectin targeting peptide or antibody and is usable (has high affinity) for P-selectin which is overexpressed on tumor endothelial cells, and/or tumor cells of, for example, glioblastoma, melanoma, ovarian carcinoma, head and neck squamous cell carcinoma, breast cancer and renal cell carcinoma.

In some embodiments, the targeting moiety is usable (has high affinity) for targeting a bone mineral (e.g., hydroxyapatite) and can be, for example, can be an aminobisphosphonate such as alendronate.

Additional cell surface receptors include, for example, Her-2 neu (Erb-2), which can be targeted using antibody to Her-2; and EGFR which can be targeted using, for example, peptides or small molecules such as Iressa, Tarceva, etc.

Additional targeting moieties which are ligands of cell-surface receptors as described herein are also contemplated.

Labeling Agents:

In some of any of the embodiments described herein, the polymeric matrix has a labeling agent associated therewith (e.g., covalently attached thereto).

The attachment of a labeling agent to the conjugate enables utilizing these conjugates for monitoring bone related disease or disorders, for example, monitoring the therapeutic effect exhibited by the conjugate described herein.

As used herein, the phrase "labeling agent" describes a detectable moiety or a probe. Exemplary labeling agents which are suitable for use in the context of these embodiments include, but are not limited to, a fluorescent agent, a radioactive agent, a magnetic agent, a chromophore, a bioluminescent agent, a chemiluminescent agent, a phosphorescent agent and a heavy metal cluster.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}$Tc, $^{18}$F $^{131}$I and $^{125}$I.

The term "magnetic agent" describes a substance which is attracted to an externally applied magnetic field. These substances are commonly used as contrast media in order to improve the visibility of internal body structures in Magnetic resonance imaging (MRI). The most commonly used compounds for contrast enhancement are gadolinium-based. MRI contrast agents alter the relaxation times of tissues and body cavities where they are present, which depending on the image weighting can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process The term "chemiluminescent agent" describes a substance which emits light as the result of a chemical reaction.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

The Agents:

The phrase "therapeutically active agent", which is interchangeably referred to herein as "drug" or simply as "agent", describes a compound which exhibits a beneficial pharmacological effect when administered to a subject and hence can be used in the treatment of a condition that benefits from this pharmacological effect. This phrase encompasses an agent associated with a polymeric matrix as described herein, for example, a first agent, and the additional agent, as described herein.

In some of any of the embodiments described herein the agent (e.g., first agent) associated with a polymeric matrix according to the present embodiments, is such that downregulates an activity and/or expression of a polypeptide associated with the onset and/or progression of melanoma.

By "associated with onset and/or progression of melanoma" it is meant that the polypeptide has an essential role in the differentiation, proliferation and/or migration of melanoma cells and is typically involved in one or more signaling pathways that affect differentiation, proliferation and/or migration of melanoma cells. The polypeptide can be, for example, a mutated polypeptide that is expressed by a mutated gene that is associated with the onset of melanoma and/or with acquired resistance of melanoma cells, a polypeptide that is overexpressed or exhibits an aberrant activity as a result of a mutated gene associated with the onset and/or with acquired resistance of melanoma cells, and/or a polypeptide that regulates cellular pathways that lead to malignant cellular proliferation, inhibition of apoptosis, and/or invasion when aberrantly activated.

By "downregulation" and grammatical diversions thereof it is meant that an activity and/or expression of the polypeptide is inhibited by at least 10%, at least 20%, at least 30%, at least 40%, at least 50%, and preferably by 60% or more.

In some embodiments, the polypeptide is involved in the mitogen activated protein kinase (MAPK) pathway.

Several polypeptides are involved in key pathways (e.g., MAPK pathway) associated with the onset and/or progression of melanoma, some are discussed hereinabove. All such polypeptides are contemplated.

In some embodiments, the polypeptide is associated with proliferation of melanoma cells.

In some embodiments, inhibition of an activity of the polypeptide reduces or inhibits proliferation of melanoma cells.

In some embodiments, inhibition of an expression of the polypeptide reduces or inhibits proliferation of melanoma cells.

In some embodiments, the polypeptide is associated with metastasis of melanoma cells.

In some embodiments, inhibition of an activity of the polypeptide reduces or inhibits metastasis of melanoma cells.

In some embodiments, inhibition of an expression of the polypeptide reduces or inhibits metastasis of melanoma cells.

Exemplary polypeptides include MEK, BRAF and c-kit, as described hereinabove.

In some embodiments, the polypeptide is a mutated polypeptide, which is expressed by a mutated gene that is associated with the onset and/or progression of melanoma.

It is to be noted that while a first agent as described herein is defined as therapeutically active agent towards melanoma, this agent is not to be regarded as therapeutically active only towards melanoma cells. Thus, polypeptides associated with the onset and/or progression of melanoma, as described herein, are also associated with the onset and/or progression of other types of cancer, and agents known to downregulate such polypeptides and hence usable in treating melanoma, are usable in treating also such types of cancer.

In exemplary embodiments, the first agent is an agent that down-regulates MEK and/or BRAF, which is also referred to as MEK inhibitor (MEKi), BRAF inhibitor (BRAFi) or a MEK/BRAF inhibitor (MEKi/BRAFi). Exemplary such agents are indicated hereinabove and in the Examples section that follows. Any other MEK and/or BRAF inhibitors are contemplated.

Some such inhibitors are therapeutically active in tumors which exhibit BRAF mutation and some are active only in tumors that exhibit BRAF mutation.

Exemplary agents include selumetinib, debrafenib, vemurafenib, PD318088, Pimasertib, cobimetinib, sorafenib, LGX818, GDC 0879, and other c-kit, MEK and/or BRAF inhibitors indicated herein, or a structural analog thereof.

In exemplary embodiments, the first agent is selumetinib.

In exemplary embodiments, the first agent is debrafenib or a structural analog thereof.

In some of any of the embodiments described herein, a therapeutically active agent is an agent useful in treating melanoma or metastases thereof, e.g., brain metastases, either per se, or when used with one or more of the agents (an additional agent) described herein.

According to some of any of the embodiments described herein, the polymeric conjugate comprises an additional agent (an additional therapeutically active agent, e.g., a second agent).

In some of the embodiments where the conjugate comprises two therapeutically active agents, these agents act in synergy or at least exhibit an additive therapeutic effect.

In embodiments pertaining to conjugates in which the drug is covalently attached to a polymeric backbone, the additional (e.g., second) agent is attached to another portion of backbone units of the polymeric backbone, which portion is referred to herein as a second portion. A third portion, comprising yet another additional agent is also contemplated.

In some of the embodiments pertaining to nanoparticles having a drug associated therewith, the additional agent is also in association with the polymeric matrix. In some of these embodiments, both the first and second agents are associated (e.g., encapsulated) within the same nanoparticle, and in some embodiments, the polymeric matrix comprises a plurality of nanoparticles, wherein a first portion of the nanoparticles comprises the first agent associated with the nanoparticle and a second portion of the nanoparticles comprises the additional agent in association with the nanoparticles. A third portion, comprising yet another additional agent is also contemplated.

In some of these embodiments, the first and second agents act in synergy.

By "act in synergy" it is meant that when both agents are contacted together with a polypeptide associated with melanoma as described herein, for example, with cells expressing such a polypeptide (e.g., melanoma cells), the therapeutic activity is higher than the additive activity of each agent alone. In some embodiments, the therapeutic activity is downregulation of a polypeptide associated with melanoma as described herein. In some embodiments, the therapeutic activity is associated with inhibiting growth, proliferation, differentiation, migration and/or angiogenesis of the cells expressing the polypeptide (e.g., melanoma cells).

By "act in synergy" it is also meant that when an activity of a polymeric conjugate bearing the two agents is higher than the activity of a mixture of a polymeric conjugate bearing one agent and a polymeric conjugate bearing another agent, whereby the activity is as described herein.

Synergy can be determined by methods known in the art. In some embodiments, synergy is determined by means of an isobologram, as widely described in the art.

In some embodiments, the additional agent is a second agent that down-regulates an activity or expression of a polypeptide associated with onset or progression of melanoma. The polypeptide can be the same or different as that of the first agent, yet the second agent is different from the first agent.

In some embodiments, the second agent is a second agent that down-regulates MEK and/or BRAF, the second agent being different from the first agent.

Exemplary second (additional) agents include, without limitation, selumetinib, debrafenib, vemurafenib, PD318088, Pimasertib, cobimetinib, sorafenib, LGX818, GDC 0879 and structural analogs thereof.

In some embodiments, a first agent downregulates MEK and an additional (a second) agent downregulates BRAF.

In some of these embodiments, the first and second agents act in synergy.

In some embodiments, the first agent downregulates MEK and the additional (e.g., second) agent also downregulates MEK but is different from the first agent. In some of these embodiments, the first and second agents act in synergy.

In some embodiments, the first agent downregulates a polypeptide as described herein (e.g., MEK or BRAF), and the additional agent is an agent usable in treating cancer by affecting other pathways associated with the cancer.

In some embodiments, the additional agent is an agent that is usable in the treatment of melanoma.

In some embodiments, the additional agent acts in synergy with the first agent in the treatment of melanoma.

In some embodiments, the additional agent is an anti-angiogenesis agent.

The phrase "anti-angiogenesis agent", which is also referred to herein interchangeably as "anti-angiogenic agent" or "angiogenesis inhibitor", describes an agent having the ability to (a) inhibit endothelial cell proliferation or migration, (b) kill proliferating endothelial cells, and/or (c) inhibit the formation of new blood vessels in a tissue.

An exemplary anti-angiogenic agent is Paclitaxel.

In some embodiments, the additional agent is paclitaxel.

In some embodiments, the additional agent is temozolomide.

In some embodiments, the additional agent is camptothecin or any of its derivatives.

Any other agents that can act together with the first agent in treating cancer that is associated with the polypeptide as described herein (e.g., in treating melanoma) are contemplated as the additional agent.

In some embodiments, the additional agent comprises two or more agents, each being attached to a different portion of backbone units in the polymeric backbone, in embodiments pertaining to conjugates having a drug covalently attached to a polymeric backbone.

In some embodiments, the additional agent comprises two or more agents, being associated with nanoparticles as described herein, either to the same portion of nanoparticles associated with the first agent, or with different portions of particles.

Any of the agents described herein can be attached to the backbone units using synthetic methodologies known in the art, or otherwise described herein and exemplified in the Examples section that follows.

Any of the agents described herein can be associated with polymeric matrices as described herein using synthetic methodologies known in the art, or otherwise described hereinafter and exemplified in the Examples section that follows.

Uses:

The conjugates described herein are usable in treating any cancer in which downregulating a polypeptide as described herein is beneficial.

In some embodiments, the conjugates described herein are usable in treating cancers associated with a polypeptide as described herein. That is, in some embodiments, the conjugates described herein are usable in treating cancers in which a polypeptide as described is associated with the onset and/or progression of the cancer.

In some embodiments, the conjugates described herein are usable in treating cancers associated with an aberrant activity and/or expression of a polypeptide as described herein. In some embodiments, the conjugates described herein are usable in treating cancers in which onset and/or progression of the disease is associated with a mutated gene that expresses a mutated polypeptide as described herein and/or with overexpression of the polypeptide and/or with aberrant activity of the polypeptide. In some embodiments, the conjugates described herein are usable in treating melanoma.

In some embodiments, the conjugates described herein are usable in treating a cancer associated with BRAF mutation. In some of these embodiments, the BRAF mutation is BRAF V600E or V600D.

As discussed herein, a high frequency of a BRAF mutation is found in melanoma patients. Yet, a BRAF mutation is also found in substantial frequencies in other types of cancers.

Non-limiting examples of cancers which have been identified to date as associated with a BRAF mutation as described herein include glial cancers such as Pilocytic astrocytoma; Diffuse astrocytoma; Anaplastic astrocytoma; Oligodendroglioma; Anaplastic oligodendroglioma; Oligoastrocytoma; Anaplastic oligoastrocytoma; Primary glioblastoma; Secondary glioblastoma; Giant cell glioblastoma; Gliosarcoma; Gliomatosis cerebri; Ependymoma; Anaplastic ependymoma; Pleomorphic xanthoastrocytoma; Pleomorphic xanthoastrocytoma with anaplasia; Medulloblastoma; Ganglioglioma; Meningioma; and Pituitary adenoma, and other cancer types.

In some embodiments, the conjugates described herein are usable in treating a cancer associated with de-regulated (e.g., aberrant) activity of a polypeptide as described herein.

Thus, according to another aspect of embodiments of the invention there is provided a method of treating cancer in a subject in need thereof. The method is effected by administering to the subject a therapeutically effective amount of any of the conjugates described herein. In some embodiments, the cancer is treatable by at least a first agent, and optionally by an additional agent, as described herein. In some embodiments the onset and/or progression of the cancer is associated with a polypeptide as described herein.

In some embodiments, the cancer is a CNS-metastasizing cancer.

Exemplary cancers include brain cancer (e.g., glioblastoma), non-small cell lung cancer (NSCLC), melanoma, and colon cancer.

In some embodiments, the cancer is glioblastoma.

In some embodiments, the cancer is melanoma.

Thus, according to another aspect of embodiments of the invention there is provided a method of treating melanoma in a subject in need thereof. The method is effected by administering to the subject a therapeutically effective amount of any of the conjugates described herein.

Accordingly, according to another aspect of some embodiments of the present invention there are provided uses of the conjugates described herein as a medicament. In some embodiments, the medicament is for treating cancer as described herein, in a subject in need thereof. In some embodiments, the medicament is for treating melanoma as described herein, in a subject in need thereof.

According to another aspect of some embodiments of the present invention, the conjugates described herein are for use in the treatment of cancer as described herein, in a subject in need thereof. In some embodiments, the conjugates described herein are for use in the treatment of melanomas described herein, in a subject in need thereof.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

This term encompasses any inhibition of tumor growth and/or metastasis, or any attempt to inhibit, slow or abrogate tumor growth and/or metastasis. The method includes killing cancer cells (e.g., melanoma cells) by non-apoptotic as well as apoptotic mechanisms of cell death.

It is understood that the conjugates of the present invention may be administered in conjunction with other drugs, including other anti-cancer and anti-angiogenic drugs, particularly those useful in treating cancer as described herein (e.g., melanoma). Such combinations are known in the art.

The term "melanoma" as used herein throughout describes any type of melanoma, as described hereinabove, and further encompasses metastases thereof, for example, brain (CNS) metastases of melanoma.

In some embodiments, the melanoma is a CNS-metastasizing melanoma.

The term "subject" (alternatively referred to herein as "patient") as used herein refers to an animal, preferably a mammal, most preferably a human, who has been the object of treatment, observation or experiment.

In some embodiments, the subject is identified (diagnosed) as having cancer as described herein. In some embodiments, the subject is identified (diagnosed) as having an aberrant activity and/or expression of a polypeptide as described herein. In exemplary embodiments, the subject is identified (diagnosed) as bearing a BRAF mutation as described herein.

As used herein, the terms "cancer", "cancerous disease" and "tumor" are interchangeably used. The terms refer to a malignant growth and/or tumor caused by abnormal and uncontrolled cell proliferation (cell division). The term "cancer" encompasses tumor metastases. The term "cancer cell" describes the cells forming the malignant growth or tumor.

Non-limiting examples of cancers and/or tumor metastases include any solid or non-solid cancer and/or tumor metastasis, including, but not limiting to, tumors of the gastrointestinal tract (e.g., colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic breast cancer, susceptibility to breast cancer, type 4 breast cancer, breast cancer-1, breast cancer-3, breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B-cell lymphoma, Diffuse large B-cell lymphoma (DLBCL), Burkitt lymphoma, cutaneous T-cell lymphoma, histiocytic lymphoma, lymphoblastic lymphoma, T-cell lymphoma, thymic lymphoma), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibro sarcoma, giant cell tumor, glial tumor, glioblastoma (e.g., multiforme, astrocytoma), glioma hepatoma, heterohybridoma, heteromyeloma, histiocytoma, hybridoma (e.g., B-cell), hypernephroma, insulinoma, islet tumor, keratoma, leiomyoblastoma, leiomyosarcoma, leukemia (e.g., acute lymphatic leukemia, acute lymphoblastic leukemia, acute lymphoblastic pre-B cell leukemia, acute lymphoblastic T cell leukemia, acute megakaryoblastic leukemia, monocytic leukemia, acute myelogenous leukemia, acute myeloid leukemia, acute myeloid leukemia with eosinophilia, B-cell leukemia, basophilic leukemia, chronic myeloid leukemia, chronic B-cell leukemia, eosinophilic leukemia, Friend leukemia, granulocytic or myelocytic leukemia, hairy cell leukemia, lymphocytic leukemia, megakaryoblastic leukemia, monocytic leukemia, monocytic-macrophage leukemia, myeloblastic leukemia, myeloid leukemia, myelomonocytic leukemia, plasma cell leukemia, pre-B cell leukemia, promyelocytic leukemia, subacute leukemia, T-cell leukemia, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme, multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

The phrase "therapeutically effective amount" describes the amount of a compound which is sufficient to effect treatment when administered to a subject in need of such treatment or prevention. As used herein this phrase describes the amount of conjugate which is sufficient to downregulate activity and/or expression of a polypeptide as described herein. In some embodiments, this phrase describes the amount of conjugate which is sufficient to treat cancer, as described herein. In some embodiments, this phrase describes the amount of conjugate which is sufficient to treat melanoma, as described herein.

According to another aspect of some embodiments of the present invention there are provided uses of any of the conjugates described herein, having a labeling agent as described herein, as diagnostic agents and/or in the manufacture of a diagnostic agent for monitoring cancer (e.g., melanoma) or monitoring cancer (e.g., melanoma) treatment.

Suitable imaging techniques include but are not limited to positron emission tomography (PET), gamma-scintigraphy, magnetic resonance imaging (MRI), functional magnetic resonance imaging (fMRI), magnetoencephalography (MEG), single photon emission computerized tomography (SPECT) computed axial tomography (CAT) scans, ultrasound, fluoroscopy and conventional X-ray imaging. The choice of an appropriate imaging technique depends on the nature of the labeling agent, and is within the skill in the art. For example, if the labeling agent comprises Gd ions, then the appropriate imaging technique is MRI; if the labeling agent comprises radionuclides, an appropriate imaging technique is gamma-scintigraphy; if the labeling agent comprises an ultrasound agent, ultrasound is the appropriate imaging technique, etc.

Pharmaceutical Composition:

According to another aspect of embodiments of the invention there is provided a pharmaceutical composition comprising, as an active ingredient, any of the conjugates described herein and a pharmaceutically acceptable carrier.

Accordingly, in any of the methods and uses described herein, any of the conjugates described herein can be provided to an individual either per se, or as part of a pharmaceutical composition where it is mixed with a pharmaceutically acceptable carrier.

As used herein a "pharmaceutical composition" refers to a preparation of one or more of the conjugates described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, antiviral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1, p.1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally, intrathecally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described hereinabove is packaged in a packaging material and identified in print, in or on the packaging material, for use in the treatment of melanoma.

According to another embodiment of the present invention, the pharmaceutical composition is packaged in a packaging material and identified in print, in or on the packaging material, for use in monitoring melanoma.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The compositions described herein may further comprise one or more additional agents usable in downregulating a polypeptide as described herein and/or in treating cancer as described herein, which are not in association with a polymeric matrix as described herein.

General:

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Herein throughout, the phrase "linking moiety" or "linking group" describes a group that connects two or more moieties or groups in a compound. A linking moiety is typically derived from a bi- or tri-functional compound, and can be regarded as a bi- or tri-radical moiety, which is connected to two or three other moieties, via two or three atoms thereof, respectively.

Exemplary linking moieties include a hydrocarbon moiety or chain, optionally interrupted by one or more heteroatoms, as defined herein, and/or any of the chemical groups listed below, when defined as linking groups.

When a chemical group is referred to herein as "end group" it is to be interpreted as a substituent, which is connected to another group via one atom thereof.

Herein throughout, the term "hydrocarbon" collectively describes a chemical group composed mainly of carbon and hydrogen atoms. A hydrocarbon can be comprised of alkyl, alkene, alkyne, aryl, and/or cycloalkyl, each can be substituted or unsubstituted, and can be interrupted by one or more heteroatoms. The number of carbon atoms can range from 2 to 20, and is preferably lower, e.g., from 1 to 10, or from 1 to 6, or from 1 to 4. A hydrocarbon can be a linking group or an end group.

As used herein, the term "amine" describes both a —NR'R" group and a —NR'— group, wherein R' and R" are each independently hydrogen, alkyl, cycloalkyl, aryl, alkaryl, heteroaryl, heteroalicyclic, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, alkenyl, alkynyl, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, silyl, guanyl, guanidine and hydrazine.

The term "amine" is used herein to describe a —NR'R" group in cases where the amine is an end group, as defined hereinunder, and is used herein to describe a —NR'— group in cases where the amine is a linking group or is or part of a linking moiety.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 6, or 1 to 4 carbon atoms (C(1-4) alkyl). The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, silyl, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Alkene (or alkenyl) and Alkyne (or alkynyl), as used herein, are an alkyl, as defined herein, which contains one or more double bond or triple bond, respectively.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, silyl, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyrane, morpholine, oxalidine, and the like. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, silyl, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, silyl, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, silyl, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, pyrrolidone, oxazole, indole, purine and the like.

The term "alkaryl" describes an alkyl, as defined herein, which is substituted by one or more aryl or heteroaryl groups, as defined herein. An example of alkaryl is benzyl.

The term "halide", "halogen" and "halo" describe fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "isocyanate" describes an —N=C=O group.

The term "isothiocyanate" describes an —N=C=S group.

The term "nitro" describes an —NO$_2$ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "carboxylate" as used herein encompasses C-carboxylate and O-carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R''' end group or a —NR'—C(=S)—NR"— linking group, with R', R" and R''' as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

An amide can be linear or cyclic. When cyclic, R' and the carbon atom are linked together to form a ring, in C-amide, and this group is also referred to as lactam. Cyclic amides can function as a linking group, for example, when an atom in the formed ring is linked to another group.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R''' end group or a —R'NC(=N)—NR"— linking group, as these phrases are defined hereinabove, where R', R" and R''' are as defined herein.

The term "hydrazine" describes a —NR'—NR"R''' end group or a —NR'—NR"— linking group, as these phrases are defined hereinabove, with R', R", and R''' as defined herein.

The term "hydrazone" describes a —C(=O)—NR'—NR"R''' end group or a C(=O)—NR'—NR"— linking group, as these phrases are defined hereinabove, with R', R", and R''' as defined herein.

As used herein, the term "hydrazide" describes a —C(=O)—NR'—NR"R''' end group or a —C(=O)—NR'—NR"— linking group, as these phrases are defined hereinabove, where R', R" and R''' are as defined herein.

As used herein, the term "thiohydrazide" describes a —C(=S)—NR'—NR"R''' end group or a —C(=S)—NR'—NR"— linking group, as these phrases are defined hereinabove, where R', R" and R''' are as defined herein.

As used herein, the term "alkylene glycol" describes a —O—[(CR'R")$_z$—O]$_y$R''' end group or a —O—[(CR'R")$_z$—O]$_y$— linking group, with R', R" and R''' being as defined herein, and with z being an integer of from 1 to 10, preferably, 2-6, more preferably 2 or 3, and y being an integer of 1 or more. Preferably R' and R" are both hydrogen. When z is 2 and y is 1, this group is ethylene glycol. When z is 3 and y is 1, this group is propylene glycol.

When y is greater than 4, the alkylene glycol is referred to herein as poly(alkylene glycol). In some embodiments of the present invention, a poly(alkylene glycol) group or moiety can have from 10 to 200 repeating alkylene glycol units, such that z is 10 to 200, preferably 10-100, more preferably 10-50.

The term "phosphonate" describes a —P(=O)(OR')(OR") end group or a —P(=O)(OR')(O)— linking group, as these phrases are defined hereinabove, with R' and R" as defined herein.

The term "carbonyl" or "carbonate" as used herein, describes a —C(=O)—R' end group or a —C(=O)— linking group, as these phrases are defined hereinabove, with R' as defined herein. This term encompasses ketones and aldehydes.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "cyclic ring" encompasses a cycloalkyl, a heteroalicyclic, an aryl (an aromatic ring) and a heteroaryl (a heteroaromatic ring).

Other chemical groups are to be regarded according to the common definition thereof in the art and/or in line of the definitions provided herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Analytical Methods

Dabrafenib was purchased from Jinan Trio Pharmatech Co., Ltd.

Selumetinib was purchased from Jinan Trio Pharmatech Co., Ltd.

Temozolomide was purchased from Lixin Pharmaceuticals.

Paclitaxel was purchased from Petrus Chemicals.

All other chemical reagents and solvents were purchased from known vendors unless otherwise indicated.

Dynamic Light Scattering (DLS) was used to determine particle size, using a Malvern Nano ZS (Malvern Instruments, UK) and Vasco$^y$ particle size analyzer. Cumulative analysis was used to determine the Z-average size.

Zeta potential was measured by Laser Doppler Velocimetry (LDV) in combination with Phase Analysis Light Scattering (PALS), using the same equipment.

SEM images were taken using Quanta 200 FEG Environmental SEM (FEI, Oregon, USA) at high vacuum and 5.0 KV. Diameters were measured by measureIT software, Particle's distribution was fitted to single-pick Gaussian using OriginPro software.

SLS measurements were performed using Wyatt MALS (DAWN® HELEOST II)

NMR ($^1$H, $^{19}$F, $^{13}$C) spectra were obtained using Bruker Avance I and Avance III 400 MHz ($^1$H) and 100 MHz ($^{13}$C) spectrometer.

GPC was performed using Viscotek GPCmax by Malvern using refractive index detector and PEG standards (purchased from Sigma-Aldrich) were used for calibration. DMF (purchased from Sigma, HPLC grade) was used as mobile phase.

| Abbreviations | |
|---|---|
| AcOH | Acetic acid |
| Ar | Aryl |
| Bn | Benzyl |
| BOC | tert-Butoxycarbonyl |
| bpy | 2,2'-bipyridine |
| BRAF | Serine/threonine kinase |
| Cat. | Catalyst |
| COD | 1,5-cyclooctadiene |
| COMU | (1-Cyano-2-ethoxy-2-oxoethylidenaminooxy)dimethylamino-morpholino-carbenium hexafluorophosphate |
| CPT | Camptothecin |
| DBF | Dabrafenib |
| DBU | 1,8-Diazabicycloundec-7-ene |
| DCC | N,N'-Dicyclohexylcarbodiimide |
| DCM | Dichloromethane |
| DDW | Double-distilled water |
| DEAD | Diethyl azodicarboxylate |
| DIC | N,N'-Diisopropylcarbodiimide |
| Dipea | N,N-Diisopropylethylamine |
| DMAP | 4-Dimethylaminopyridine |
| DMF | Dimethylformamide |
| EPR | Enhanced permeability and retention |
| eq' | Equivalent |
| ERK | Extracellular signal-regulated kinase |
| Et | Ethyl |
| FDA | Food and drug administration |
| Glu | Glutamic |
| Gly | Glycine |
| GFLG | Gly-Phe-Leu-Gly |
| HBTU | N,N,N',N'-Tetramethyl-O-(1H-benzotriazol-1-yl)uronium hexafluorophosphate |
| HMDS | Hexamethyldisilazane |
| HOBt | 1-Hydroxybenzotriazole |
| HPMA | N-(2-Hydroxypropyl) methacrylamide |
| m.p. | Melting point |
| MAPK | Mitogen-activated protein kinase |
| Me | Methyl |
| MEK | Threonine and tyrosine kinase |
| Mn | Number average molar mass |
| MTBD | 7-Methyl-1,5,7-triazabicyclo[4.4.0]dec-5-ene |
| Mw | Mass average molar mass |
| NCA | N-Carboxyanhydride |
| NSCLC | Non-small-cell lung carcinoma |
| OS | Overall survival |
| PBLG | Poly(γ-benzyl-1-glutamate) |
| PDC | Polymer-drug conjugate |
| PEG | Polyethylene glycol |
| PGA | Poly (α,L-glutamic acid) |
| PK1 | [N-(2-hydroxypropyl)methacrylamide copolymer doxorubicin] |
| PyBop | Benzotriazol-1-yl oxytripyrrolidinophosphonium hexafluorophosphate |
| R | Alkyl, Aryl, Allyl |
| Rt | Room temperature |
| RAF | Serine/threonine-protein kinase |
| RAS | Small GTPase protein |
| SLM | Selumetinib |
| SLS | Static light scattering |
| SMA | Polystyrene-maleic anhydride copolymer |
| SMANCS | Poly(styrene-comaleic acid)-neocarzinostatin |
| TFA | Trifluoroacetic acid |
| THF | Tetrahydrofuran |

Example 1

Poly (α,L-Glutamic Acid) (PGA) Syntheses

The challenge in PGA synthesis lies in obtaining PGA in different molecular weights with good polydispersity.

α-Amino acid-N-carboxyanhydride (NCA) ring opening polymerization is a conventional method, traditionally initiated using many different nucleophiles and bases, the most common being primary amines and alkoxide anions, as shown in Scheme 1 below [Cheng & Deming, *Peptide-Based Materials*, Vol. 310 (ed. Deming, T.) 1-26 (Springer Berlin Heidelberg, 2012)].

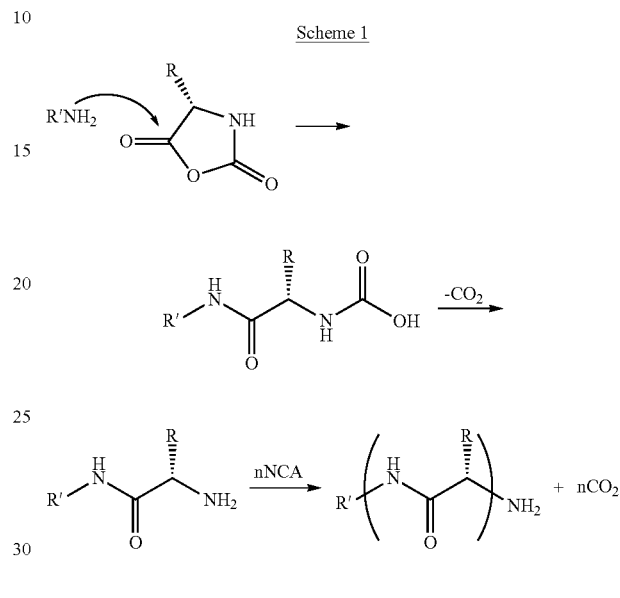

Scheme 1

One inherent problem in conventional NCA polymerizations is that there is no control over the reactivity of the growing polymer chain-end during the course of the polymerization. Once an initiator reacted with a NCA monomer, it is no longer active in the polymerization and the resulting primary amine, carbamate, or NCA anion end group is free to undergo a variety of undesired side reactions. Another problem is associated with the purity of the NCA monomers.

One strategy for eliminating side reactions in NCA polymerizations is the use of transition metal complexes as active species to control addition of NCA monomers to polymer chain-ends. The use of transition metals to control reactivity has been proven in organic and polymer synthesis as a means to increase both reaction selectivity and efficiency [Collman et al. *Principles and applications of organotransition metal chemistry*, 2nd edn. University Science, Mill Valley, (1987)]. The metal ions can be conveniently removed from the polymers by simple precipitation or dialysis of the samples after polymerization.

Using this approach, substantial advances in controlled NCA polymerization have been made in recent years. Highly effective nickel (0) and cobalt initiators were developed to allow the living polymerization of NCAs into high molecular weight polypeptides via an unprecedented activation of the NCAs into covalent propagating species (see, Scheme 2) [Deming, T. J. *Macromolecules* 32, 4500-4502 (1999); Deming, T. J. *Nature* 390, 386-389 (1997)]. These cobalt and nickel complexes are able to produce polypeptides with narrow chain length distributions (given by the polydispersity index, i.e., the weight-average molecular weight divided by the number-average molecular weight ($M_w/M_n$), which in this case is <1.2) and controlled molecular weights ($500<M_n<500,000$ g/mol) [Deming, T. J. & Curtin, S. A. *J. Am. Chem. Soc.* 122, 5710-5717 (2000)].

Scheme 2

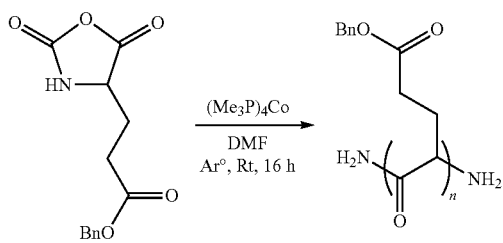

Another approach of controlling NCA polymerization is shown in Scheme 3 [Lu, H. & Cheng, J. *J. Am. Chem. Soc.* 129, 14114-14115 (2007)], involves polymerization of Bn-Glu NCA in the presence of hexamethyldisilazane (HMDS) as an initiator, and showed remarkable control of polymerizations, leading to formation of PBLG (Poly(γ-benzyl-1-glutamate)) with excellent chain length control.

Scheme 3

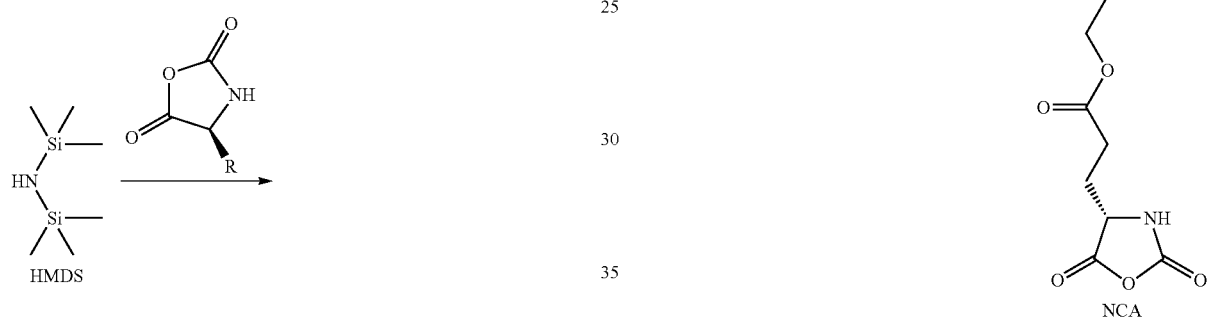

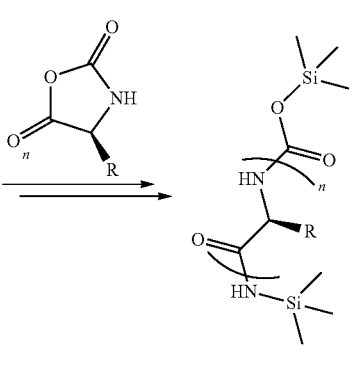

An Exemplary PGA Synthesis According to the Present Embodiments:

PGA was synthesized by ring opening polymerization of NCA of γ-benzyl-L-glutamate, prepared as depicted in Scheme 4. NCA monomers were recrystallized twice from THF/Hexane to obtain pure NCA (as determined by $^1$H-NMR analysis) with melting point of 92-93° C.

Scheme 4

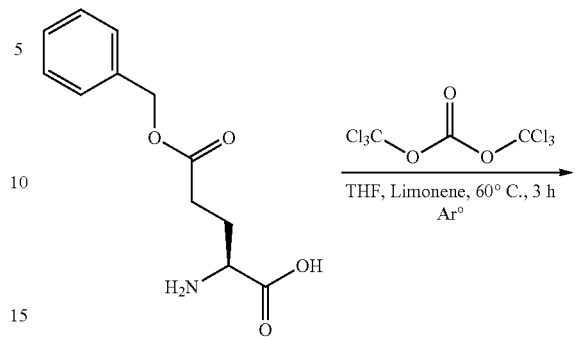

Neopentyl-NH$_3$BF was used as an initiator. Neopentyl-NH$_3$BF$_4$ was synthesized from neopentylamine and tetrafluoroboric acid diethyl ether complex in diethyl ether, as depicted in Scheme 5 below. The final product was verified by $^1$H-NMR and by $^{19}$F-NMR.

Scheme 5

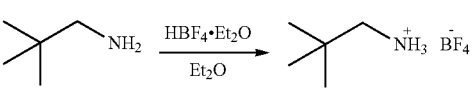

Polymerization of NCA was performed under inert conditions, while the DMF was dried with 4 Å molecular sieves for 24 hours, distilled in-vacuum at 30° C., and freshly used NCA and neopentyl-NH$_3$BF$_4$ were dried in high vacuum overnight prior to reaction. The synthesis of Poly(γ-benzyl-1-glutamate) (PLBG) is depicted in Scheme 6 below. The product was identified by GPC (DMF/0.1% NH$_4$OAc) and was determined to feature Degree of Polymerization of about 100 and PDI=polydispersity index of 1.18.

Scheme 6

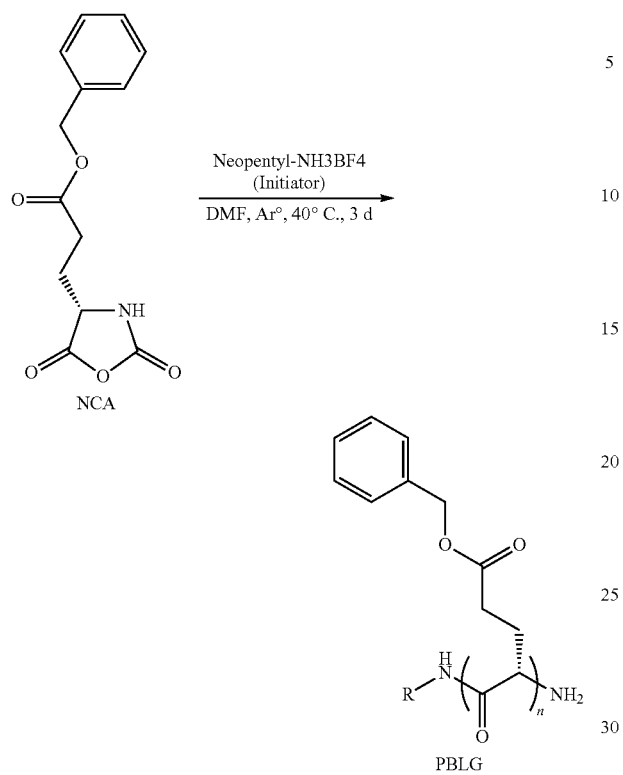

Deprotection of the product PBLG for further conjugations was performed by treatment with solution of 33% HBr/AcOH and TFA 50/50% volume, as depicted in Scheme 7 below. The final product was verified by 1H-NMR.

Scheme 7

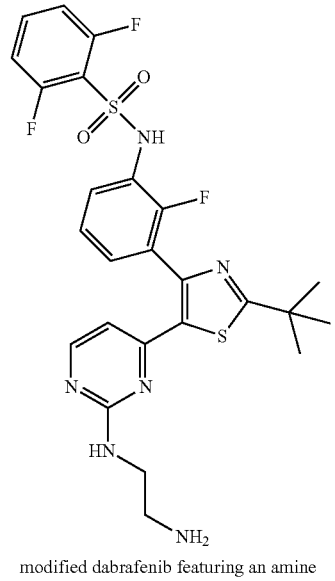

Example 2

Therapeutically Active Agents

The drugs that are currently in clinical trials, namely, dabrafenib (NCT01682083), vemurafenib (NCT01709292) and selumetinib (NCT01843062), were selected as exemplary therapeutically active agents.

In cases where the original drugs are not stable enough on the polymers or the desired loading on the polymer is not achieved, some synthetic approaches are utilized. For example, the drug is modified so as to be conjugated to the polymer stably and/or in sufficient load while retaining its activity, as shown for Dabrafenib, for example, in Scheme 8 below. Modification can be done, for example, by nucleophilic aromatic substitution, as exemplified for Dabrafenib in Scheme 9 below.

Scheme 8

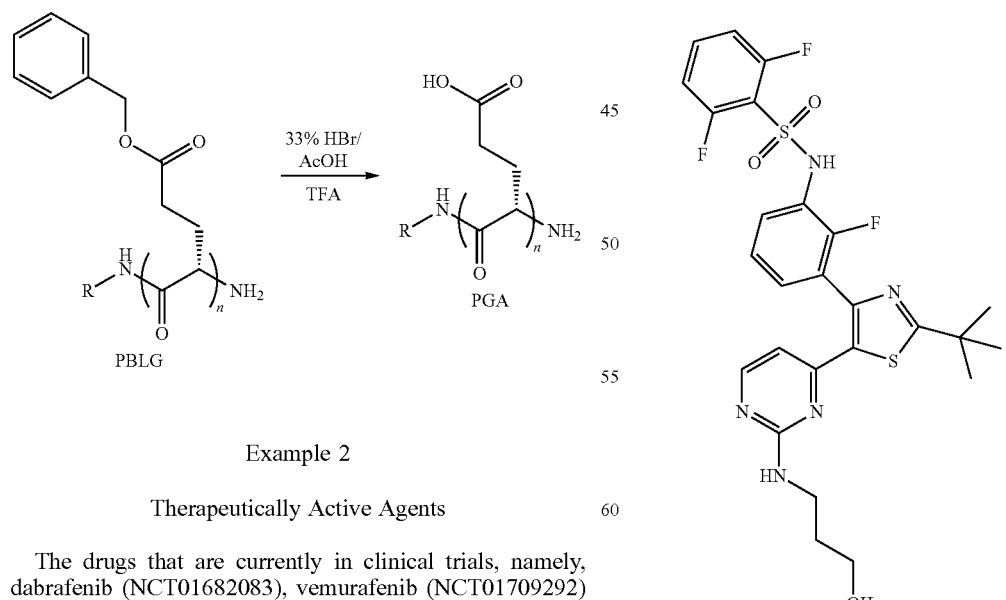

modified dabrafenib featuring an amine modified dabrafenib featuring hydroxy

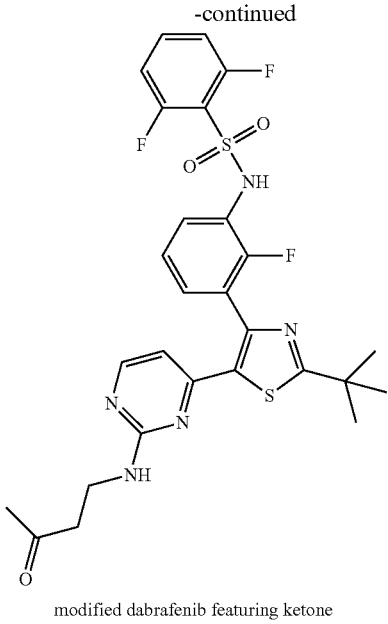

modified dabrafenib featuring ketone

Scheme 9

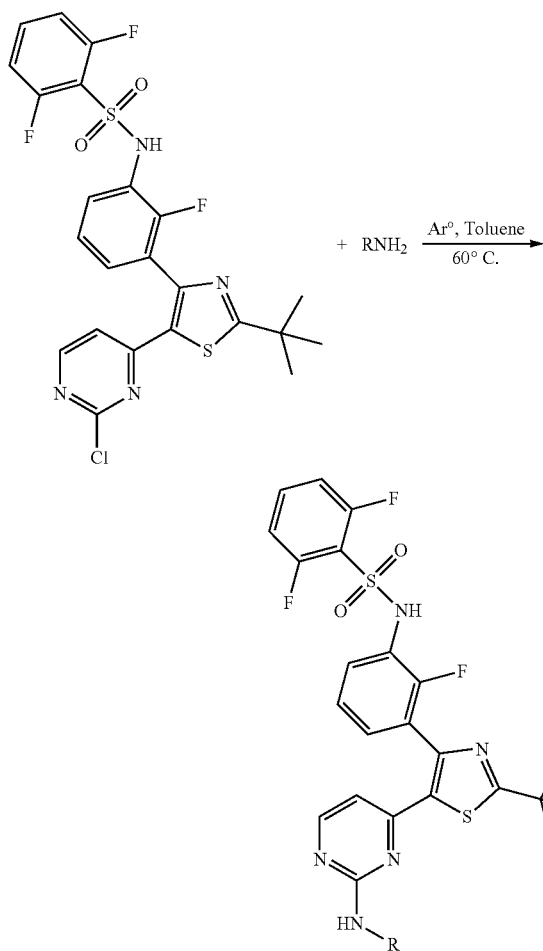

R = CH₂CH₂NH₂,
(CH₂)₃OH, (CH₂)₂COCH₃,
(CH₂)₆OH, (CH₂)₂O(CH₂)₂OH

A stable modified dabrafenib featuring a ketone functional group for hydrazine bond formation was synthesized using levulinic acid, as depicted in Scheme 10 below. The structure of the obtained compounds was verified by $^1H/^{13}C$-NMR.

Scheme 10

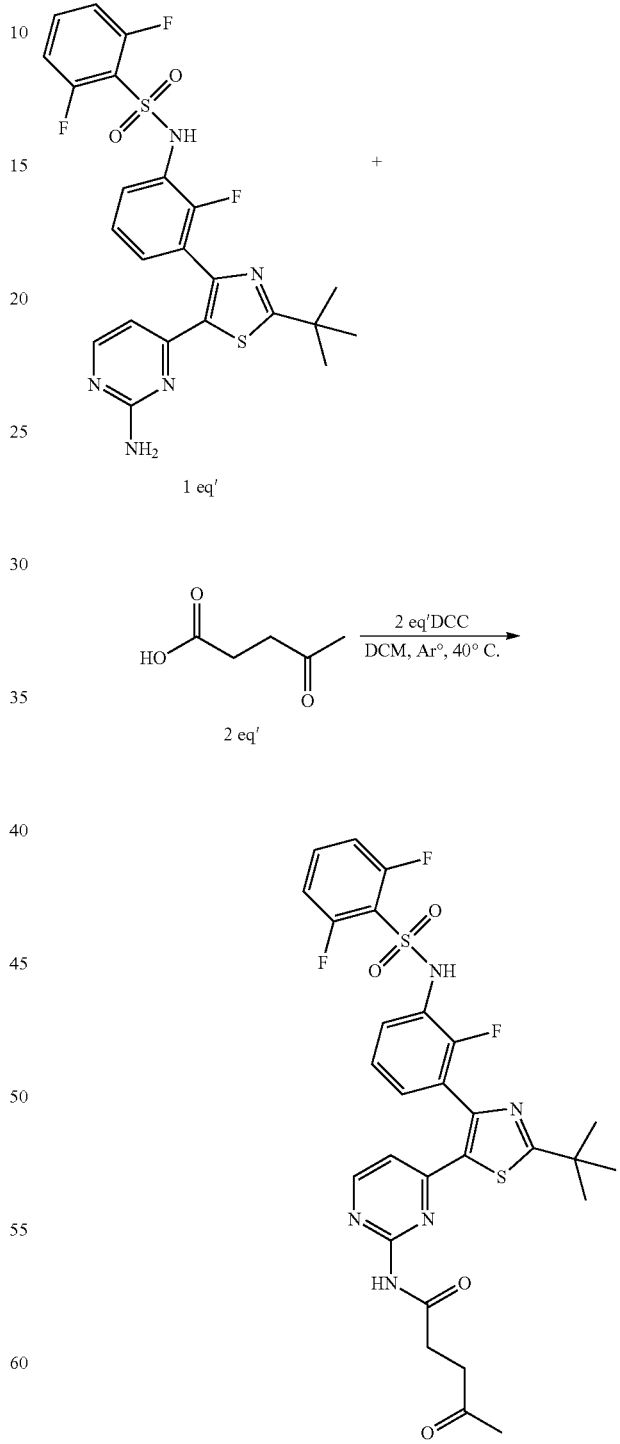

Dabrafenib modified to feature a diol functional group for further conjugation to 5 PGA was prepared as depicted in Scheme 11, and characterized by $^1H$-NMR.

Scheme 11

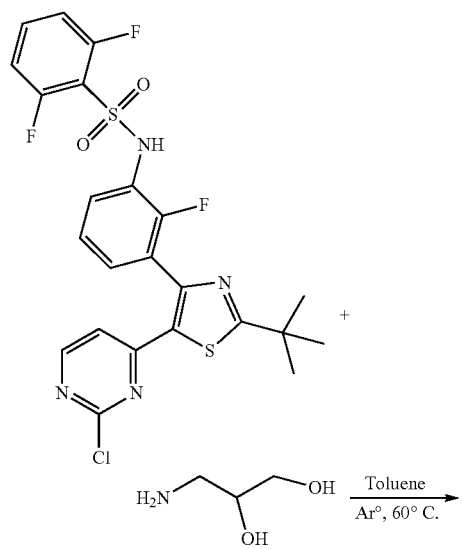

Scheme 12
Mitsunobu reaction

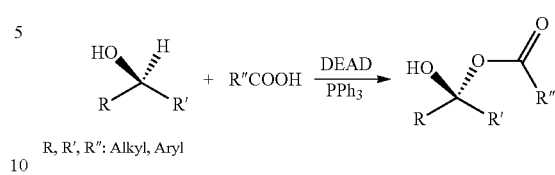

R, R', R": Alkyl, Aryl

Scheme 13
Steglich esterification

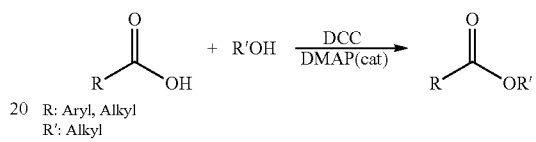

R: Aryl, Alkyl
R': Alkyl

Scheme 14

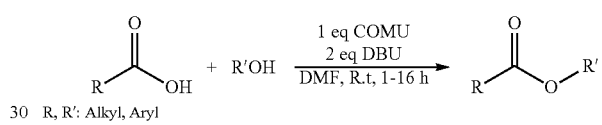

R, R': Alkyl, Aryl

Controllably Selective Preparation of Esters Using Uronium-Based Coupling Agents, as described, for example, in wibanire, J.-d. A. K. & Grindley, T. B. *Org. Lett.* 13, 2988-2991 (2011).

Scheme 15

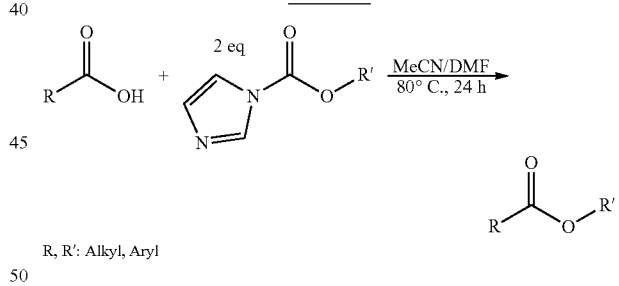

R, R': Alkyl, Aryl

Chemoselective Esterification and Amidation of Carboxylic Acids with Imidazole Carbamates, as described, for example, in Heller, S. T. & Sarpong, R. *Org. Lett.* 12, 4572-4575 (2010).

Scheme 16
Mukaiyama esterification

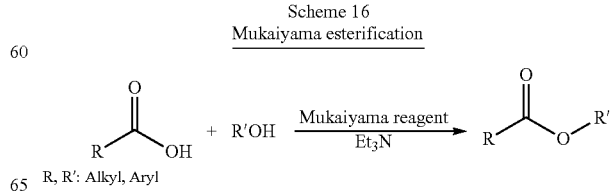

R, R': Alkyl, Aryl

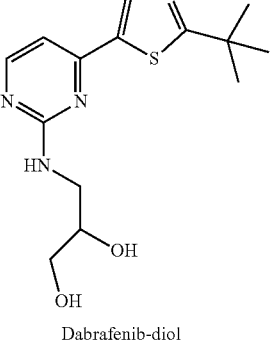

Dabrafenib-diol

Example 3

Polymer-Drug Conjugation

General Synthetic Pathways:

Exemplary synthetic methods of direct esterification and amidation can be employed in the synthesis of the polymer-drug conjugates of the present embodiments, while utilizing the available carboxylic acid group of PGA side chains, and corresponding amine or hydroxy functional groups of the drugs (therapeutically active agents), as depicted in Schemes 12-18 below.

Scheme 17

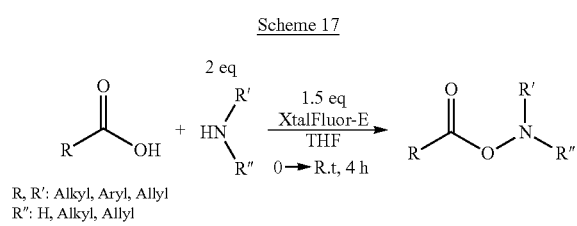

R, R': Alkyl, Aryl, Allyl
R": H, Alkyl, Allyl

Amidation of Carboxylic Acids by XtalFluor-E as Coupling Reagent, as described, for example, in Orliac et al. *Org. Lett.* 15, 902-905 (2013)

Scheme 18

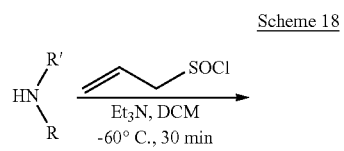

R: H, Alkyl
R': Alky, Ph, Benzyl
R": Alkyl, Vinyl, Benzyl, Ph

Amides in One Pot from Carboxylic Acids and Amines via Sulfinylamides, as described, for example, in Bai, J., Zambroń, B. K. & Vogel, P. *Org. Lett.* 16, 604-607 (2014)

PGA-Selumetinib Conjugate:

Selumetinib was conjugated to PGA by esterification reaction. Carboxylic acid groups of PGA side chains were activated by DIC, HOBt and DMAP that reacted with the primary alcohol of selumetinib, as depicted in Scheme 19 below, resulting in 1 mol % loading on the polymer. The polymeric conjugated was precipitated in cold diethyl ether, followed by salting with 0.5 M $NaHCO_3$ dialysis in 3.5 kDa membrane for 24 hours. After lyophilization, the polymer was characterized by NMR and SLS. Loading was determined by absorption calibration graph of pure selumetinib in 300 nm.

Several coupling agents were tested in order to define optimal conditions for selumetinib conjugation to PGA, and the obtained data is presented in Table 1 below. BOP-Cl was found to act as the best coupling reagent, enabling high loading of selumetinib on the PGA backbone, equivalent to 9.6 mol %.

Scheme 19

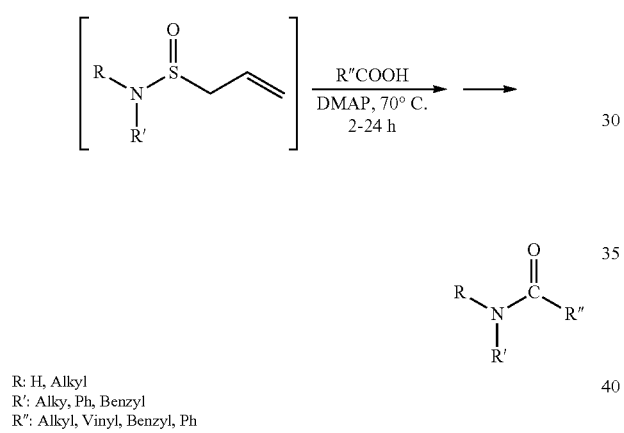

TABLE 1

| Exp. Number | PGA [Monomer Equiv'] | Selumetinib [Equiv'] | Coupling reagent [Equiv'] | Base [Equiv'] | Loading [mole %] | Loading [W/W %] |
|---|---|---|---|---|---|---|
| 72 | 100 | 20 | (HOBt/DIC) 15 | (DMAP/DIPEA) Cat' | 1 | 3 |
| 74 | 100 | 20 | (CDI) 110 | — | — | — |
| 76 | 100 | 20 | (DCC) 110 | (DMAP) Cat' | Traces | Traces |
| 77 | 100 | 10 | (Mukayama reagent) 100 | (DMAP) Cat' | 1 | 3 |
| 94 | 100 | 15 | (BOP-Cl) 30 | (DMAP/DIPEA) 60/25 | 9.6 | 29.1 |

Table 2 below presents the data obtained for physical characterization of PGA-selumetinib conjugate by SLS measurements.

TABLE 2

| Polydispersity | |
| --- | --- |
| Mw/Mn | 1.397(1%) |
| Mz/Mn | 5.608(30%) |
| Molar mass moments (g/mol) | |
| Mn | 4.824e+4(0.7%) |
| Mp | 4.524e+4(0.7%) |
| Mv | n/a |
| Mw | 6.737e+4(0.7%) |
| Mz | 2.705e+5(30%) |
| rms radius moments (nm) | |
| Rn | 24.3(4%) |
| Rw | 24.0(4%) |
| Rz | 23.9(4%) |

PGA-Dabrafenib Conjugate:

Conjugating dabrafenib to PGA via formation of an amide bond, using DCC, PyBop or HBTU as coupling agents was unsuccessful. Other coupling agents may be useful.

Modified Dabrafenib derivatives were therefore used. Modified Dabrafenib featuring a ketone group for conjugation via a hydrazone bond was prepared as shown in Scheme 10 above. Conjugation can be effected using a Glycine hydrazine linker.

Synthesis of glycine hydrazine was performed by treatment of Z-Glycine-OH and Boc-hydrazine with DCC, followed by deprotection of benzyl protection group by hydrogenation with 10% Pd/C, as described, for example, in oessens et al. *J. Controlled Release* 38, 141-150 (1996), and depicted in Scheme 20 below.

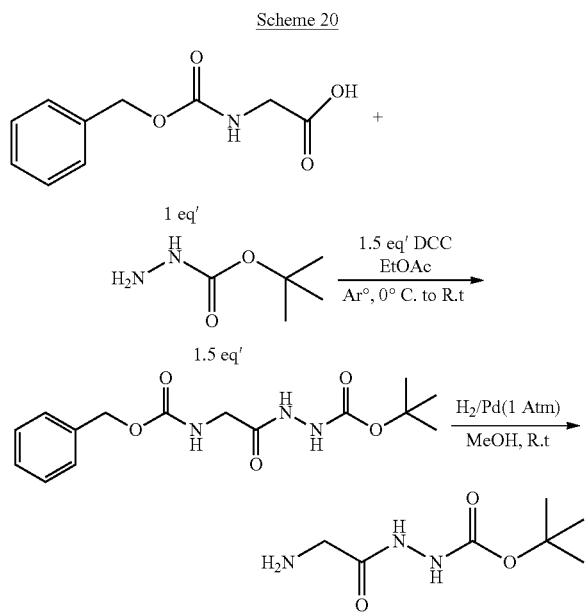

PGA-Selumetinib-Dabrafenib Conjugates:

A PGA conjugate for combination therapy includes two drugs attached to polymeric backbone units: MEK inhibitor (e.g., selumetinib) and BRAF inhibitor (e.g., a modified dabrafenib). A conjugate of PGA with BRAF inhibitor is prepared for comparative assays. The structures of exemplary such conjugates are depicted in Schemes 21 and 22 below. The ester bonds are sensitive to hydrolysis and/or cleavage by esterases.

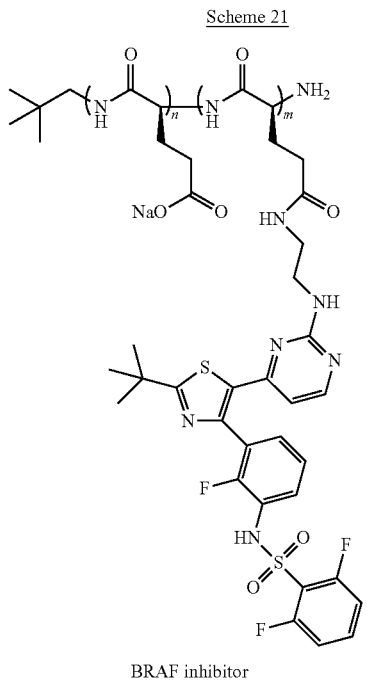

BRAF inhibitor

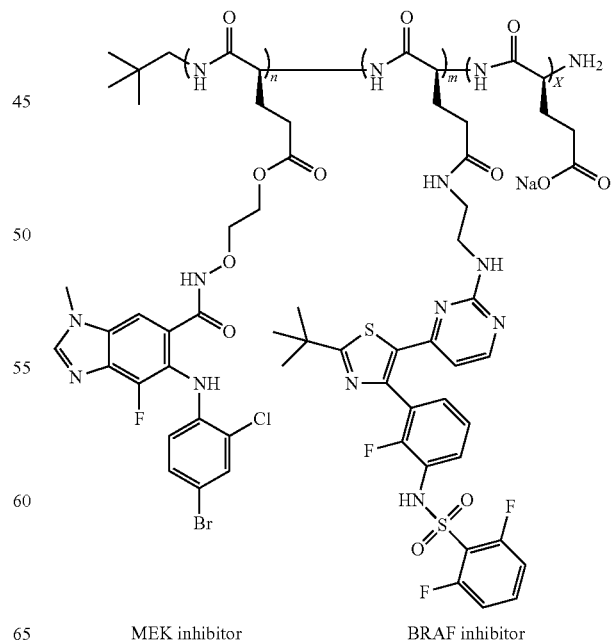

MEK inhibitor  BRAF inhibitor

Scheme 22

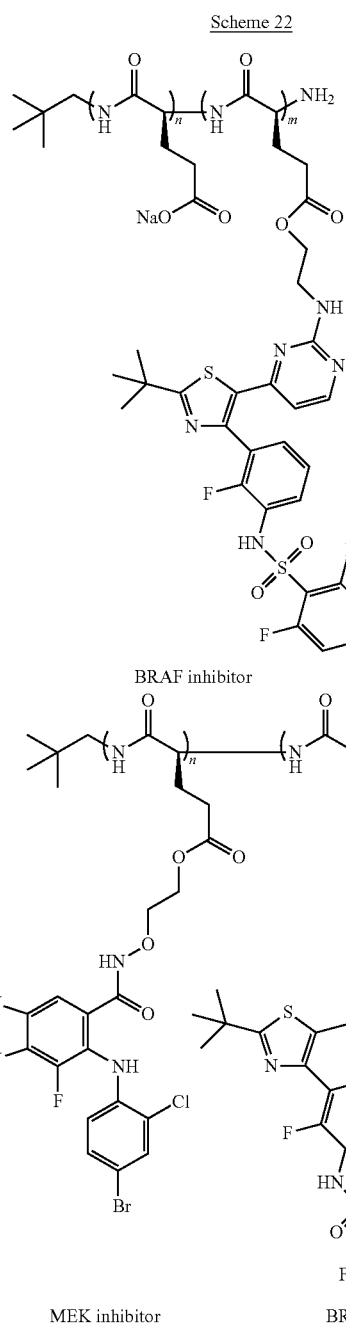

BRAF inhibitor

MEK inhibitor    BRAF inhibitor

Scheme 23 below presents the synthesis and chemical structure of a PGA conjugate with Selumetinib and diol-modified Dabrafenib (see, Scheme 11 above). PGA (50 mg; 100 equivalents of monomers), Selumetinib (10 equivalents) and diol-modified Dabrafenib (2 equivalents) were dissolved in 2.5 ml DMF and the mixture was cooled in ice bath for 15 minutes. BOP-Cl (30 equivalents), DMAP (60 equivalents), and DIPEA (25 equivalents) were thereafter added and the reaction mixture was stirred for 4 hours and then at room temperature for overnight. The reaction progression was monitored by TLC (using 10% MeOH/DCM as eluent).

Once the reaction was completed, a 10% NaCl solution was added to ice-cooled reaction mixture, followed by addition of 0.3 ml of 0.5M HCl, and the resulting mixture was stirred at room temperature for 1 hour. The precipitant was thereafter collected and washed 3 times with 20 ml DDW, dissolved in DDW/0.5M NaHCO$_3$ and dialyzed in 3.5 KDa MWCO tube until a pure conjugate was obtained, as determined by HPLC. The conjugate was thereafter lyophilized to afford a white powder.

Molar ratio of the drugs was determined by $^{19}$F-NMR using as internal standard Trifluoroethanol. The ratio SLM:DBFdiol was determined as 3:1.

The same procedure was used to prepare the conjugates depicted in Schemes 21 and 22, using the corresponding modified DBF. The ratio SLM:DBFamine was determined as 10:1.

Scheme 23

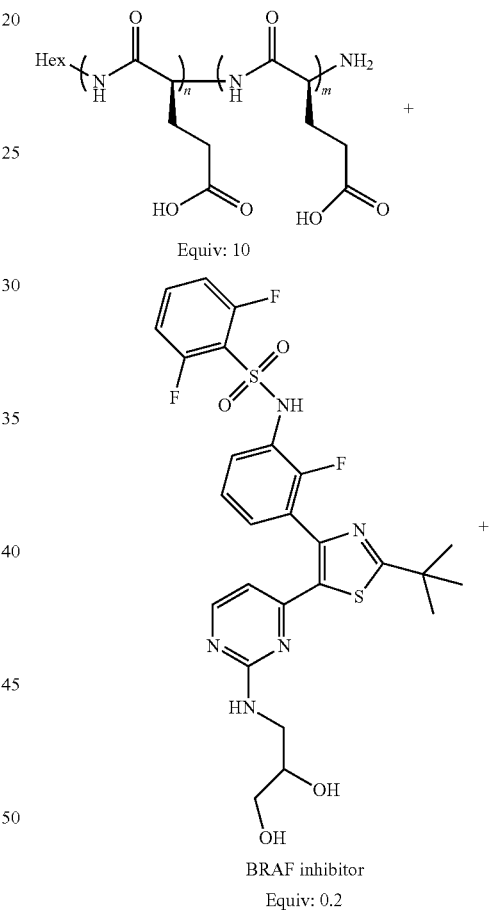

BRAF inhibitor
Equiv: 0.2

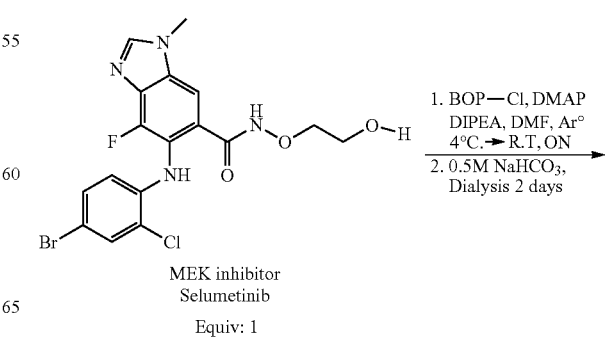

MEK inhibitor
Selumetinib
Equiv: 1

1. BOP—Cl, DMAP
   DIPEA, DMF, Ar°
   4°C.→R.T, ON
2. 0.5M NaHCO$_3$,
   Dialysis 2 days -continued

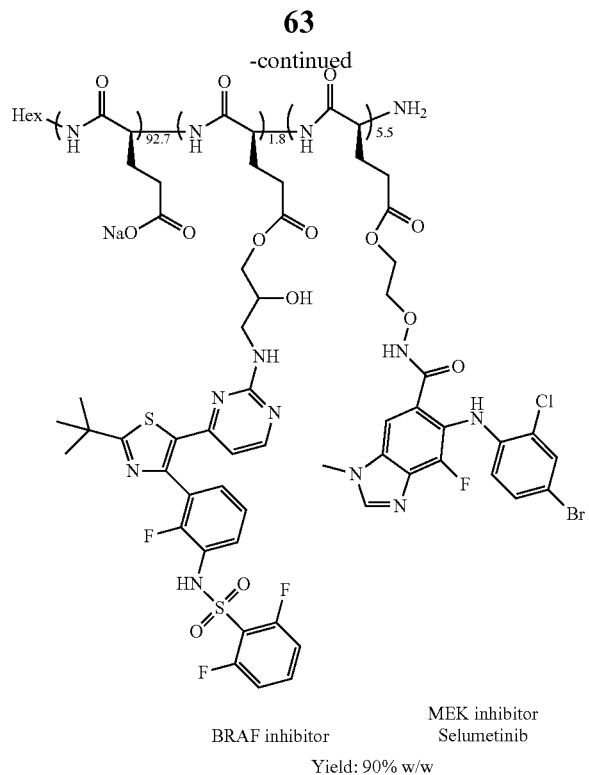

BRAF inhibitor / MEK inhibitor Selumetinib

Yield: 90% w/w

Table 3 below presents data obtained for physicochemical characterization of the prepared PGA-Selumetinib (PGA-SLM; (11.6 mol %)), PGA-Dabrafenib(diol) (PGA-DBF-diol; 10.6 mol %), PGA-SLM-DBFdiol 3:1 (5.5 mol % SLM), and PGA-SLM-DBFdiol 11:1 (8.8 mol % SLM).

TABLE 3

| Conjugate | Size [nm] | Std. Dev [nm] | Zeta [mV] | Std. Dev [mV] | $M_w$ [gr/mole] | PD |
|---|---|---|---|---|---|---|
| PGA-SLM | 6.42 | 0.38 | −60.2 | 6.45 | 6.737e+4 | 1.397 |
| PGA-DBFdiol | 11.7 | 0.62 | −56.6 | 5.32 | 2.156e+6 | 1.786 |
| PGA-SLM-DBFdiol (3:1) | 11.64 | 0.61 | −61.5 | 5.68 | 1.838e+5 | 1.261 |
| PGA-SLM-DBFdiol (11:1) | 11.24 | 0.66 | −51.3 | 5.33 | 1.092e+5 | 1.403 |

Polymeric Conjugates with Degradable Linkers:

Conjugates with various degradable linkers (e.g., enzymatically degradable, pH-sensitive, ROS-sensitive linkers) are synthesized.

An exemplary peptide linker is GFLG (SEQ ID NO:15), synthesized by solid phase peptide method and applied in the synthesis using coupling methods described previously. Conjugation of the drug by GFLG (SEQ ID NO:15) peptide linker increases sensitivity of the conjugate to cathepsin B enzyme that is overexpressed in tumors.

Exemplary conjugation methodologies are presented in FIGS. 2A-K.

Figure 2A:
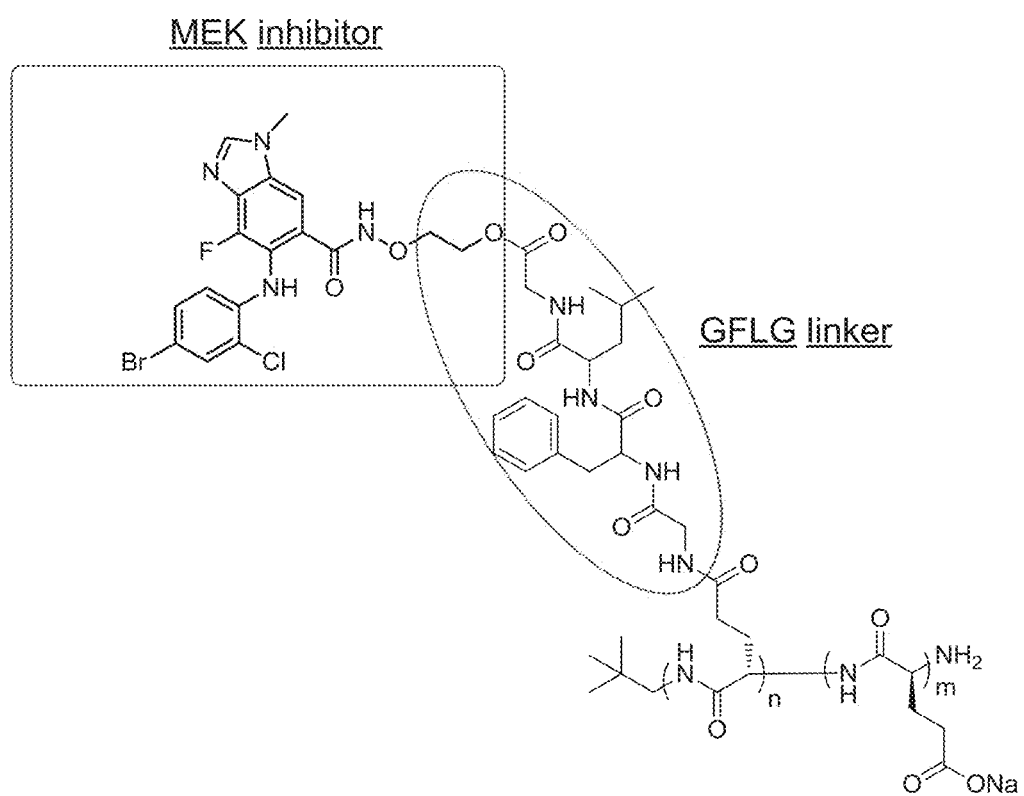

FIG. 2A presents Selumetinib-MEK inhibitor conjugated by Cathepsin B-sensitive GFLG (SEQ ID NO:15) linker to PGA.

Figures 2B, 2C:
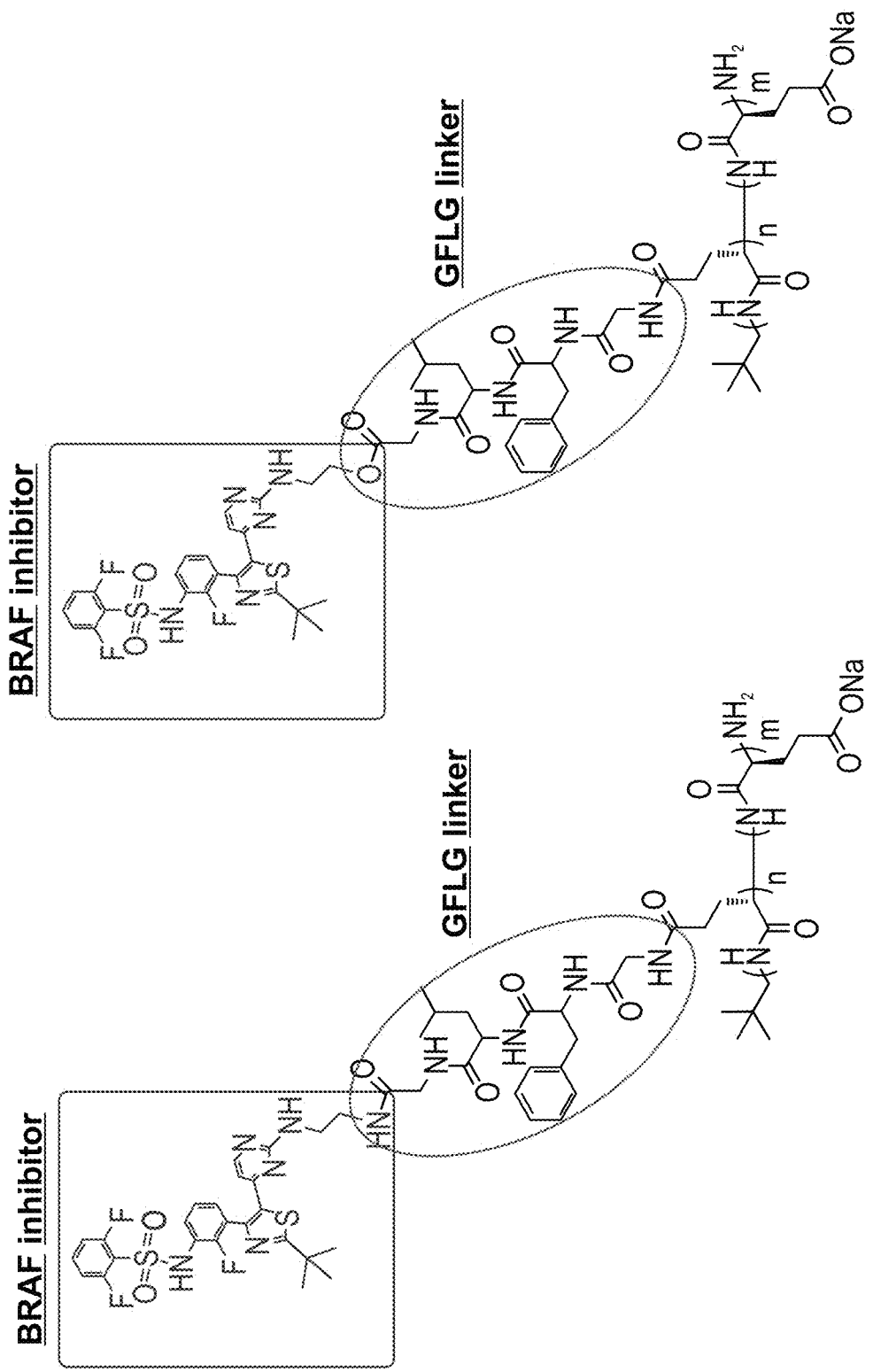

FIG. 2B presents a modified dabrafenib conjugated by Cathepsin B-sensitive GFLG (SEQ ID NO:15) linker to PGA by amide bond.

FIG. 2C presents a modified dabrafenib conjugated by Cathepsin B-sensitive GFLG (SEQ ID NO:15) linker to PGA by ester bond.

Figure 2D:
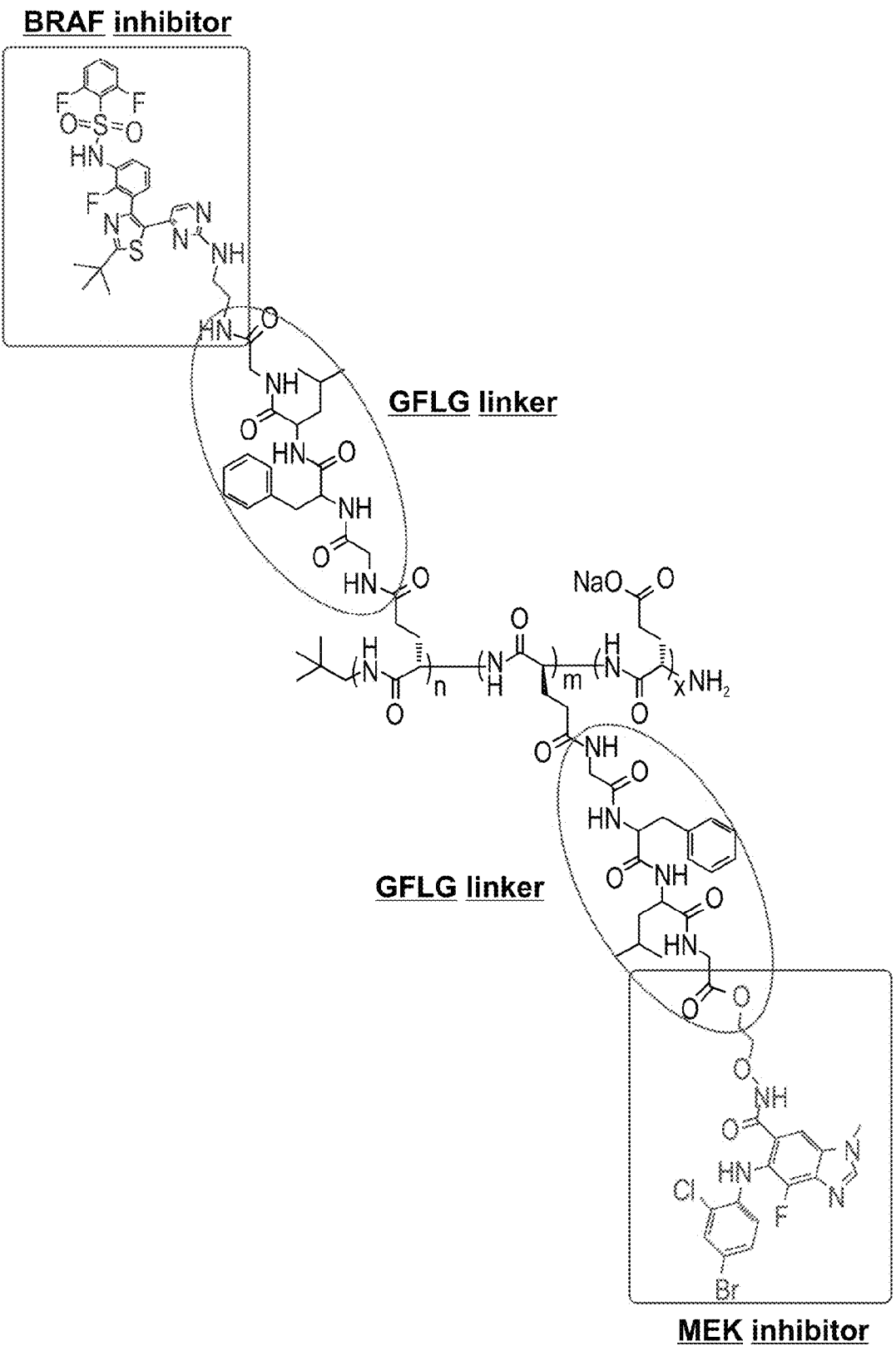

FIG. 2D presents an amine-modified dabrafenib and selumetinib bound via Cathepsin B-sensitive GFLG (SEQ ID NO:15) linker to PGA.

Figure 2E:
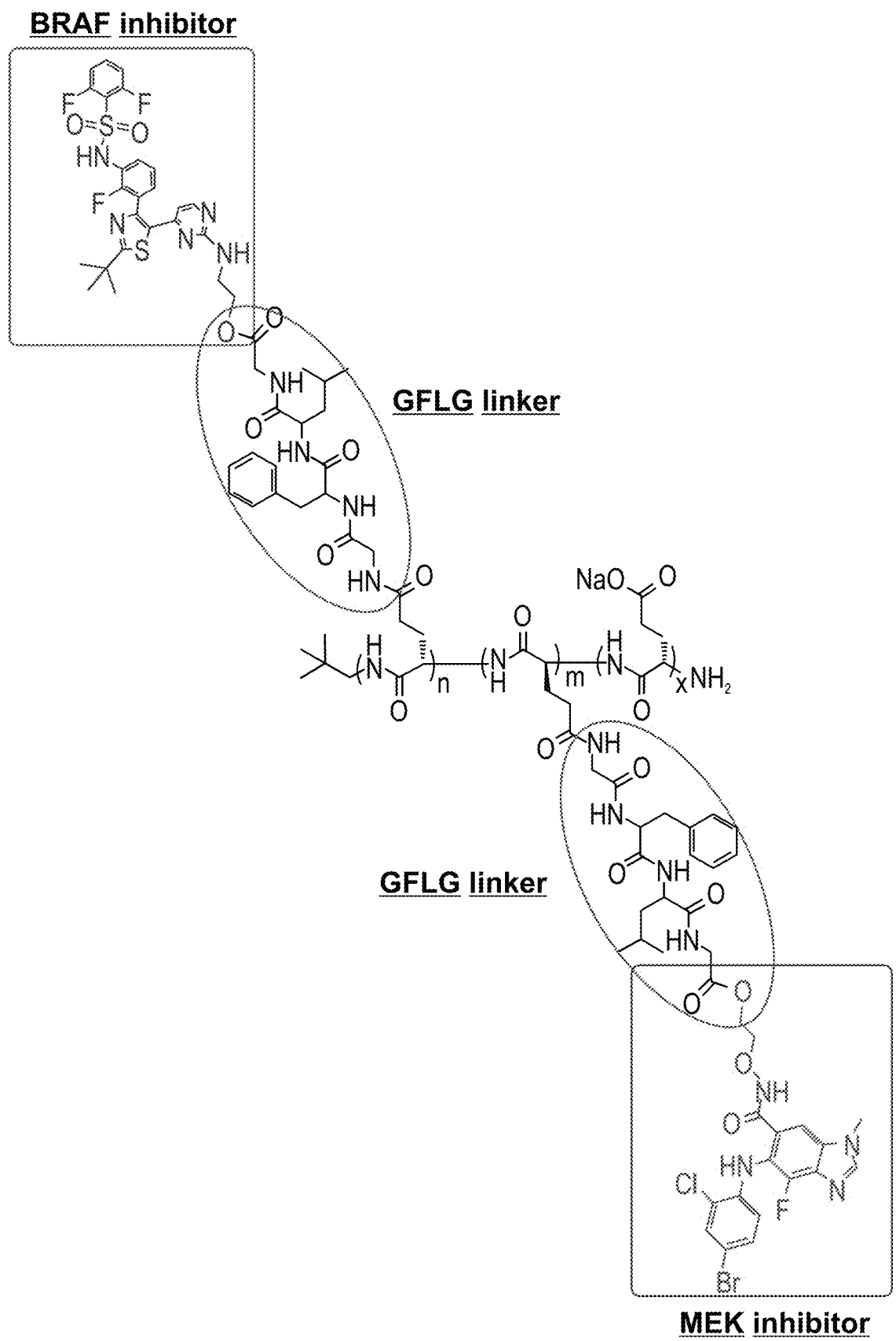

FIG. 2E presents a hydroxy-modified dabrafenib and selumetinib bound via Cathepsin B-sensitive GFLG (SEQ ID NO:15) linker to PGA.

Figure 2F:
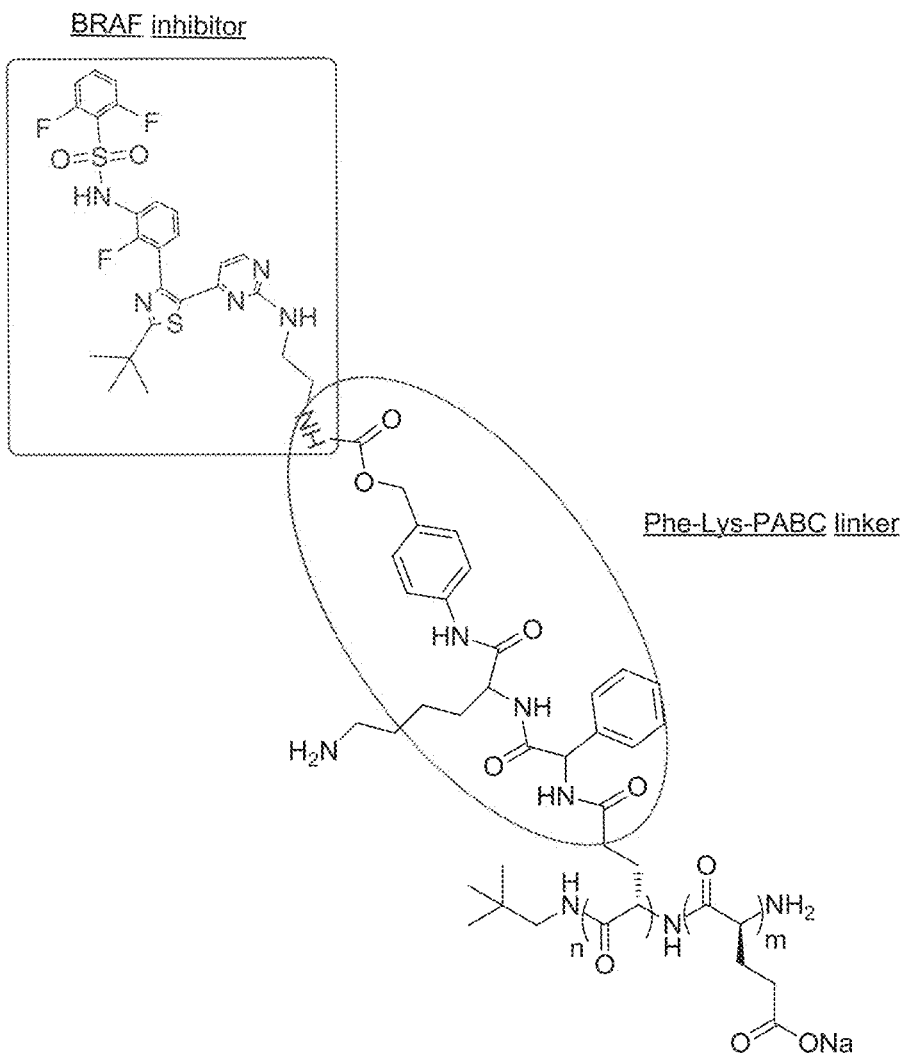

FIG. 2F presents an amine-modified dabrafenib conjugated by Cathepsin B-sensitive Phe-Lys-PABC linker to PGA that after cleavage spontaneously generate 1-6 elimination and release free drug.

Figure 2G:
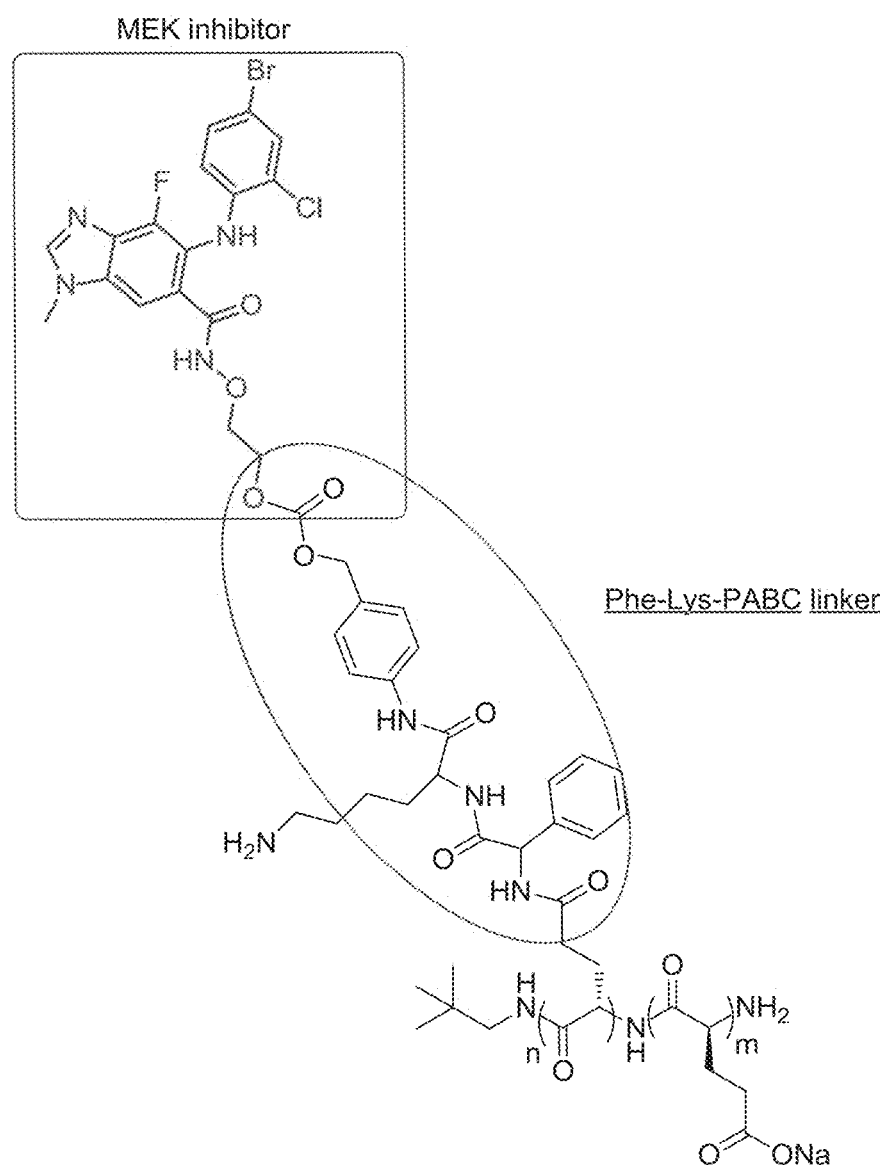

FIG. 2G presents Selumetinib bound via Cathepsin B-sensitive Phe-Lys-PABC linker to PGA that after cleavage spontaneously generate 1-6 elimination and release free drug.

Figure 2H:
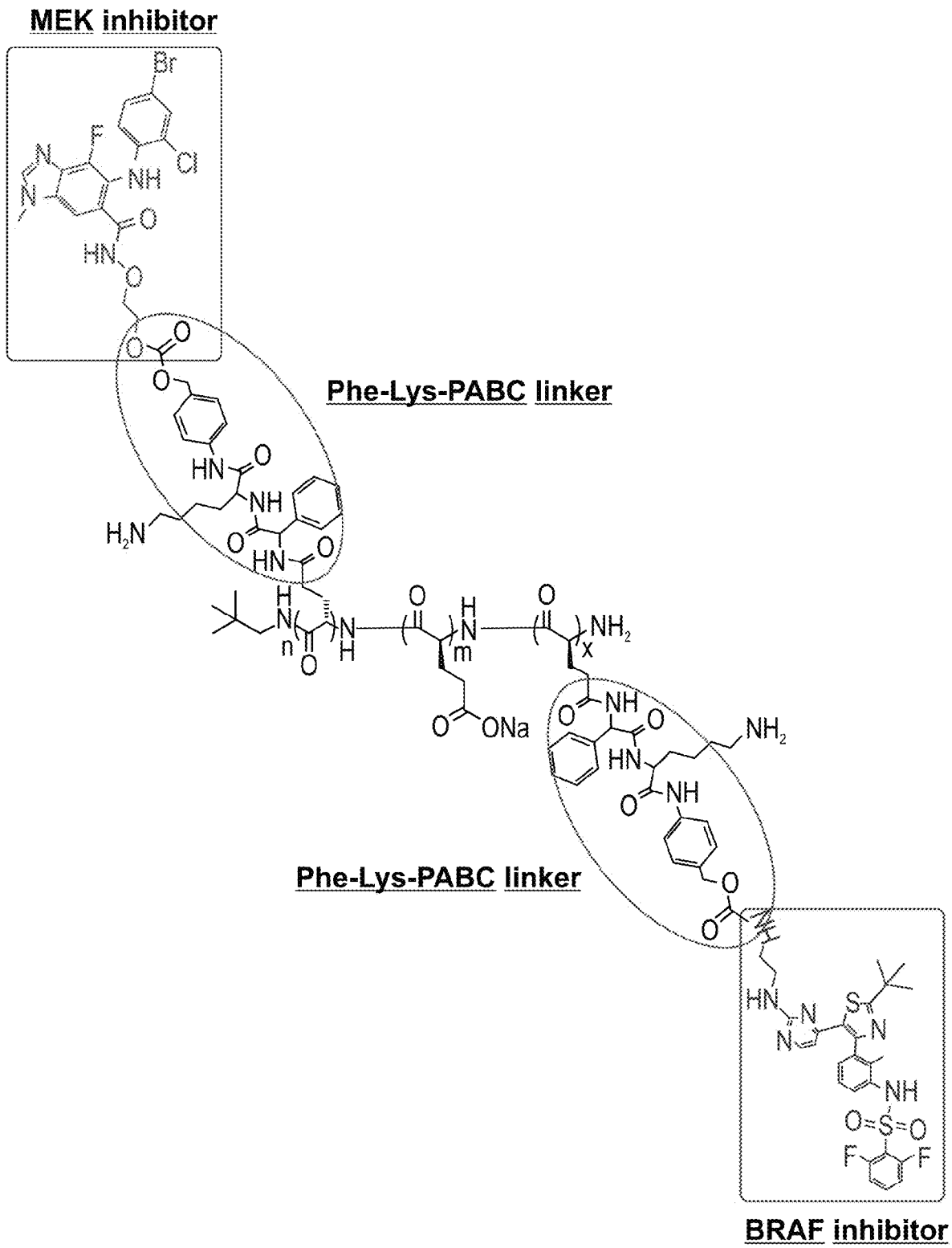

FIG. 2H presents amine-modified dabrafenib and selumetinib bound via Cathepsin B-sensitive Phe-Lys-PABC linker to PGA that after cleavage spontaneously generate 1-6 elimination and release free drugs.

FIG. 2I presents hydroxy-modified dabrafenib and selumetinib bound via Cathepsin B sensitive Phe-Lys-PABC linker to PGA that after cleavage spontaneously generate 1-6 elimination and release free drugs.

Figure 2J:
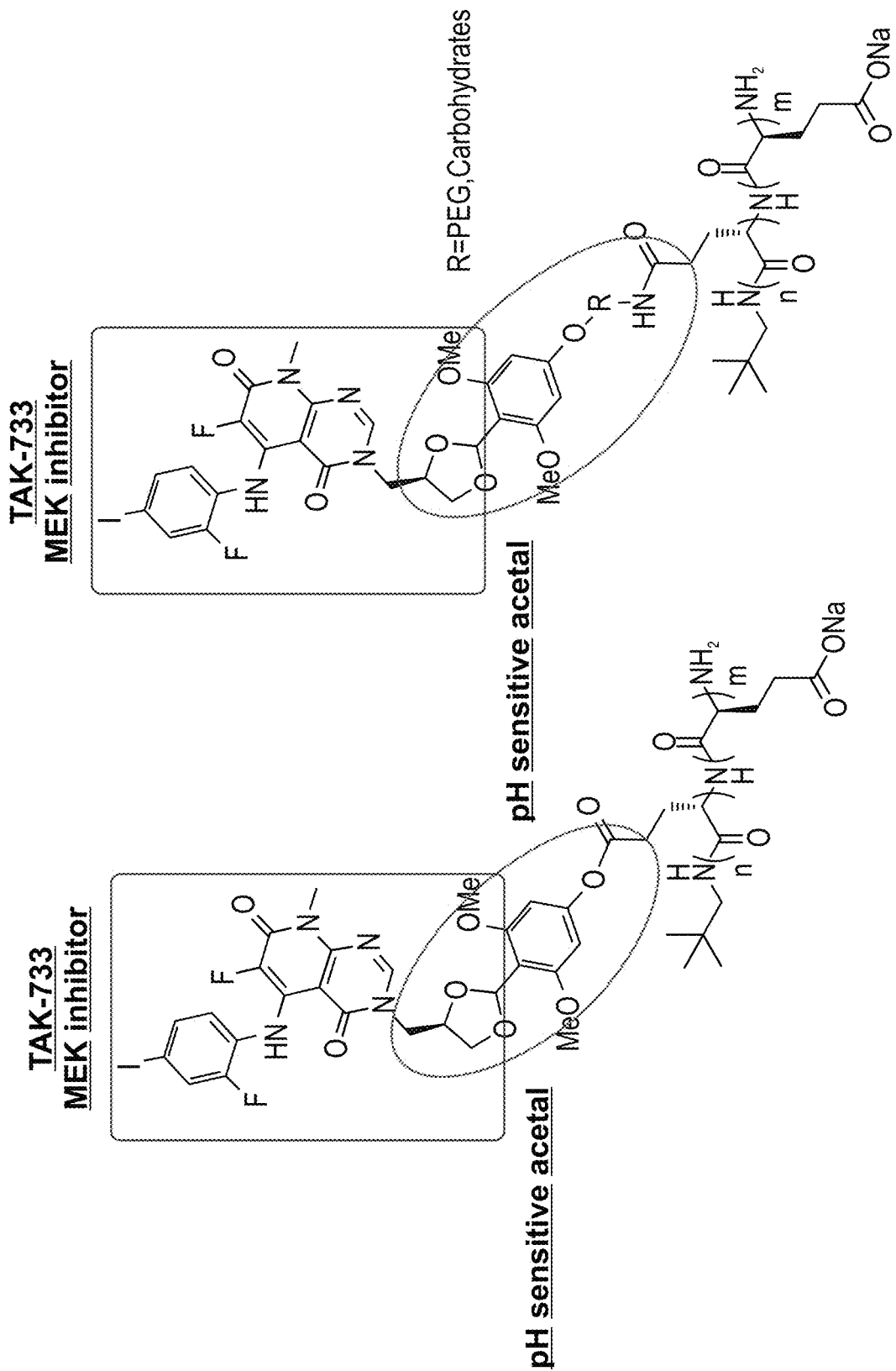

FIG. 2J presents conjugation of TAK-733 (MEK inhibitor) by acetal pH-sensitive bond for release at low pH.

Figure 2K:
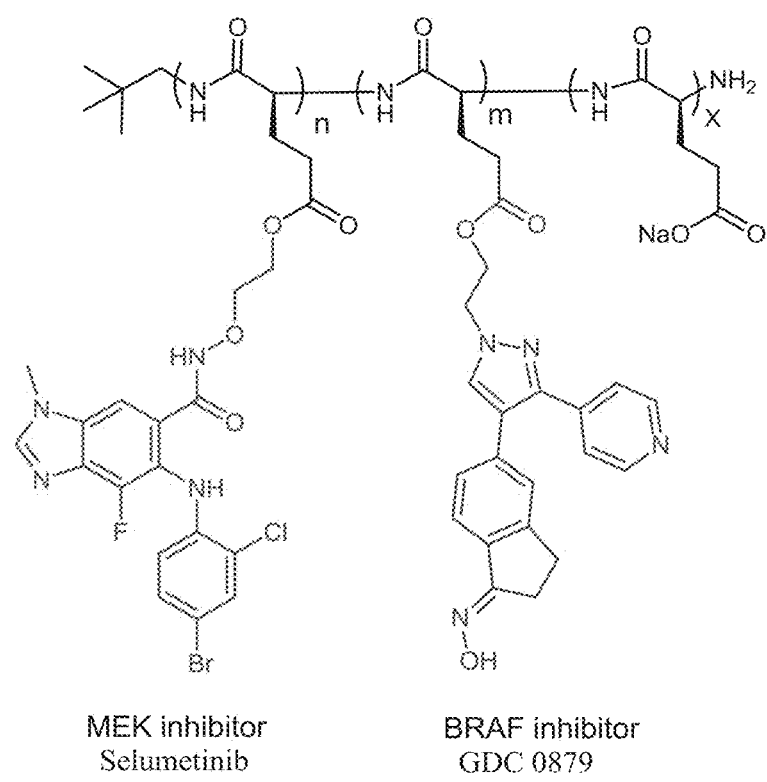

FIG. 2K presents Selumetinib (MEK inhibitor) and GDC 0879 (BRAF inhibitor) conjugated to PGA conjugate via ester bonds sensitive to hydrolysis and esterase cleavage.

Other MEK inhibitors such as PD318088 and Pimasertib shown below can be similarly conjugated to PGA.

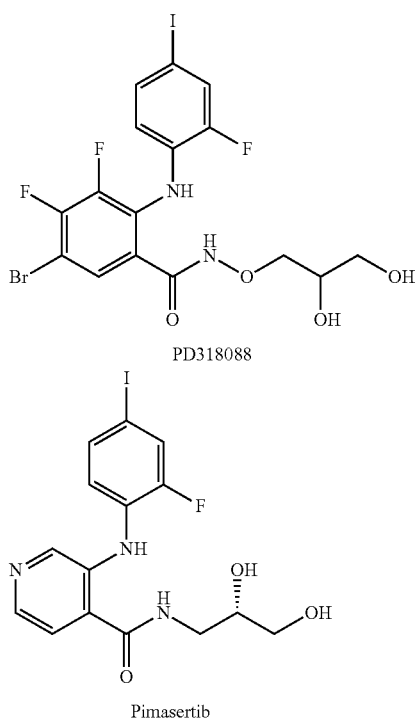

PD318088

Pimasertib

Example 4

Activity Assays

Proliferation of 13114-5B1 Melanoma Cells in the Presence of Free Drugs:

131/4-5B1 (human melanoma brain-metastasis cell line that was obtained from Dr. Kerbel' Lab) (15,000/well) were plated onto 24-well culture in RPMI medium supplemented with 10% FBS and incubated for 24 hours (37° C.; 5% $CO_2$). The medium was then replaced with RPMI supplemented with 10% FBS. Cells were exposed to free selumetinib, free amine-modified dabrafenib (Scheme 8) or both, at a SLM-DBF mol ratio of 10:1 at serial dilutions. Number of viable cells was counted by a Z1 Coulter Counter® Cell and Particle Counter (Beckman Coulter®) following 72 hours incubation.

The obtained data is presented in FIG. 3A, and show that the combination of the free drugs was synergistic. FIG. 3B presents an Isobologram showing the synergistic effect of dabrafenib and selumetinib on 131/4-5B1 melanoma cells proliferation.

Wound Healing:

Wound healing assay was performed on 131/4-5B1 human melanoma cells to evaluate the migration of the cells after treatment with free selumetinib and PGA-selumetinib (see, Scheme 19).

25,000 Melanoma cells were seeded in 96 well plate. Once the cells reached 100% confluence, a scratch was done using a Wound Maker (Essen Bioscience). The cells were washed twice with PBS and treated with the following treatments: 50 nM free selumetinib; PGA-selumetinib in equivalent dose; medium (as control). The treatments were prepared either in full medium (with serum) or starvation medium (serum free medium). The plates were incubated and monitored for 96 hours in the Incucyte® (Essen Bioscience).

FIG. 4A presents images of a monolayer of melanoma cells that have undergone a scratch obtained prior to treatment (T=0) and the end of the incubation period with the different treatments (T=95.5 hours).

FIG. 4B presents comparative showing the relative density of wound in cells grown with serum (left) and without serum (right) from time=0 to 95 hours after treatment. Blue plots show data obtained for cells only, Orange plots for cells treated with free selumetinib, and Grey plots for cells treated with PGA-selumetinib. Wound healing scale bar 0.3 cm=300 μm.

The obtained data clearly show that both selumetinib and PGA-selumetinib have the same inhibitory effect on cells migration, while a complete closure of the wound is seen in the non-treated cells.

Proliferation of 13114-5B1 Melanoma Cells in the Presence of Polymeric Conjugates:

Inhibition of 131/4-5B1, human melanoma brain-metastasis cells by free selumetinib (SLM), free diol-modified dabrafenib (DBFdiol; see, Scheme 11), a combination of the free drugs at 3:1 SLM:DBFdiol mol ratio, PGA-SLM (see, Scheme 19), PGA-DBFdiol (see, Scheme 11), a combination of PGA-SLM and PGA-DBFdiol, and PGA-SLM-DBFdiol conjugate (see, Scheme 23) was determined.

131/4-5B1 cells (15,000/well) were plated onto 24-well culture in RPMI medium supplemented with 10% FBS and incubated for 24 hours (37° C.; 5% $CO_2$). The medium was then replaced with RPMI supplemented with 10% FBS. Cells were exposed to PGA-SLM conjugate, PGA-DBFdiol conjugate, to the combination of both at a SLM-DBF mol ratio of 10:1 and to the combined PGA-SLM-DBFdiol conjugate, calculated according to the SLM loading and assuming 10:1 mol ratio between SLM and DBF, at serial dilutions. Number of viable cells was counted by a Z1 Coulter Counter® Cell and Particle Counter (Beckman Coulter®) following 72 hours incubation.

The obtained data is presented in FIGS. 5A and 5B and in Table 4 below.

As shown therein, the $IC_{50}$ value obtained for PGA-SLM-DBFdiol conjugate was better than that obtained for the mixture of PGA-SLM and PGA-DBFdiol. Moreover, substantially improved activity for the combined conjugate was observed compared to the PGA-SLM alone. Further, it is noted that while similar $IC_{50}$ values were obtained for PGA-DBFdiol and the combined PGA-SLM-DBFdiol conjugate, the relative mol % of DBFdiol in the combined conjugate is substantially lower than in the PGA-DBFdiol conjugate, as the mol % is 3:1 SLM:DBFdiol. These findings suggest that using the combined PGA-SLM-DBFdiol conjugate allows administering lower doses of the DBF without loss of its activity, and thus accounts for reduced adverse effects, including reduced toxicity and reduced chances for developing resistance to this drug (which is commonly seen in patients treating with this drug).

TABLE 4

|  | $IC_{50}$ (nM) |
| --- | --- |
| SLM | 70 |
| DBFdiol | 3 |
| SLM + DBFdiol (3:1) | 6 |
| PGA-SLM | 3500 |
| PGA-DBFdiol | 180 |
| PGA-SLM + PGA-DBFdiol (3:1) | 400 |
| PGA-SLM-DBFdiol (3:1) | 250 |
| PGA | N/A |

Red Blood Cell Lysis (RBS):

PGA-SLM-DBFdiol (see, Scheme 23) conjugates at 3:1 and 11:1 mol ratio were tested for their toxicity on red blood cells of rats.

The conjugates were prepared at 5 mg/mL concentration and serially diluted to 1, 0.5, 0.1, 0.05, and 0.001 mg/mL concentrations. SDS and 70 KDa dextran solutions were prepared at the same concentrations to use as positive and negative controls respectively. Samples were incubated for 1 hour at 37° C. in equal volume of 2% (w/w) rat red blood cells (RBC) solution that was taken from 2 different rats. Samples were centrifuged at 1000 RCF for 10 minutes. The supernatants were then transferred to a 96-wells plate and absorbance was red at 550 nm using a SpectraMax M5e plate reader (Molecular Devices, Sunnyvale, Calif., USA). Results were normalized to 100% lysis obtained by incubation in 1% (v/v) Triton X-100. The obtained data is presented in FIG. 6 and show that the conjugates do not show any toxicity on red blood cells.

Degradation by Cathepsin B:

Degradation of PGA-Selumetinib-Dabrafenib(diol) (3:1 mol ratio, see, Scheme 23) in the presence of Cathepsin B (Human) was tested as follows:

Conjugate incubation at 37° C. with Cathepsin B (10 U/ml) in freshly prepared activity phosphate buffer (0.1 M; pH=6.0), containing 0.05 M NaCl, 1 mM Ethylenediaminetetraacetic acid (EDTA) and 5 mM reduced glutathione (GSH). As a control, conjugates were incubated in the absence of Cathepsin B at the same conditions. Reaction was followed by HPLC. Degradation was monitored by reversed phase (RP) HPLC. UltiMate® 3000 Nano LC systems (Dionex) was used, equipped with 3000 pump, VWD-3000 UV-Vis detector and Chromeleon® 6.80 software. The column in use was Phenomenex Jupiter 5µ250×4.60 mm C-18 300A. Chromatographic conditions were: flow: 1.0 ml/min, gradient: 40-100% solution B in 15 min (sol. A—0.1% TFA in water; sol. B—0.1% TFA in acetonitrile (MeCN)).

The obtained data is shown in FIG. 7, for degradation of the conjugate in the presence (blue) and absence (red) of cathepsin B. As shown therein, in the presence of cathepsin B, the polymeric conjugate was degraded up to 40% within 48 hours.

Example 5

Drug-Loaded Nanoparticles

Another combination therapy approach was exploited by loading (e.g., entrapment; encapsulation) of the two drugs (BRAF and MEK1/2 inhibitors) in nanoparticles based on PLGA, as schematically illustrated in FIG. 8.

Poly(lactid-co-glycolic acid) (PLGA) polymers are biocompatible, biodegradable and FDA- and EMA-approved materials for human use, thus offering the potential for the rapid translation to the clinic.

Preparation of Nanoparticles (NP):

Double Emulsion-Solvent Evaporation (w/o/w) Method:

NP were formulated by the double emulsion-solvent evaporation (w/o/w) method, while modifying a previously reported procedure [[Garinot M, PEGylated PLGA-based nanoparticles targeting M cells for oral vaccination, 2007].

Two different types of nanoparticles were prepared: non-functionalized nanoparticles (herein referred to as NP) and mannose-functionalized nanoparticles (herein referred to as Man-NPs). NP were produced with a blend of PLA and PLGA at a ratio of 80:20, whereas Man-NP were formulated using a blend of PLA and Mannose-PLGA at a ratio of 80:20. Polymer blends were dissolved in 200 mL of dichloromethane (DCM). Empty particles were produced by adding 100 mL of a 15% PVA aqueous solution to the polymer blend.

For dabrafenib-loaded NP, the polymer blend was dissolved in 200 mL of 0.677 mg/mL dabrafenib solution in DCM and emulsified with 100 mL of a 15% PVA aqueous solution.

For selumetinib-loaded NP, 100 mL of a 15% PVA aqueous solution containing selumetinib at 11.3 mg/mL were added to the polymer blend in DCM.

For dabrafenib and selumetinib-loaded NP the polymer blend was dissolved in 200 mL of 0.677 mg/mL Dabrafenib solution in DCM, and emulsified with 100 mL of a 15% PVA aqueous solution containing selumetinib at 11.3 mg/mL.

Mixtures were emulsified with a microprobe ultrasonic processor for 30 seconds at 25% amplitude. A second emulsion was performed with the same conditions, after addition of 400 microliters of a 5% (m/V) PVA aqueous solution. The double emulsion was added dropwise into a 0.25% (m/V) PVA aqueous solution and stirred for 1 hour at room temperature. The particle suspension was then collected by centrifugation at 20,000 g for 45 minutes, 4° C. The particles were then washed with ultrapure water, collected by centrifugation and finally resuspended in PBS or ultrapure water.

PLGA-Selumetinib NP encapsulated 1.1 mg of selumetinib (98% encapsulation efficiency), PLGA-Dabrafenib NP encapsulated 0.07 mg of dabrafenib (50% encapsulation efficiency), PLGA-Selumetinib-Dabrafenib NP encapsulated 1.1 mg of selumetinib (98% encapsulation efficiency), and 0.08 mg of dabrafenib (60% encapsulation efficiency). The loading was evaluated by RP-HPLC in water/ANC 0.1% TFA, according to generated calibrations curves.

Preparation of NP Using Microfluidic Chip:

Both dabrafenib and selumetinib were dissolved in the organic phase. First, drugs were dissolved in 30 mL of DMSO (1.28 mg of selumetinib and 0.128 mg of dabrafenib), and added to a solution of PLGA:PLGA-PEG 70:30 (total amount 15 mg in 1.5 mL of acetonitrile). The aqueous phase was 2% PVA in DDW. Phases were mixed with flow rate of 8 mL/min, ratio 1:1, to a final volume of 3 mL.

Mannose-PLGA NP were formulated using a Mannose-PLGA:PLGA:PLGA-PEG 30:60:30.

Physicochemical Characterization and Morphology of NP:

Dynamic Light Scattering (DLS) was used to determine particle size, using a Malvern Nano ZS (Malvern Instruments, UK). Cumulative analysis was used to determine the Z-average size. Zeta potential of NPs was measured by Laser Doppler Velocimetry (LDV) in combination with Phase Analysis Light Scattering (PALS), using the same equipment. NPs were diluted in PBS and electrophoretic mobility was determined at 25° C. using the Helmholtz-von Smoluchowski model. Particle morphology was performed by Environmental scanning electron microscopy (SEM). Polymer solution at 0.1 mg/mL in water were dropped on a silicon wafer and blotted with cellulose paper. SEM images were taken using Quanta 200 FEG Environmental SEM (FEI, Oregon, USA) at high vacuum and 5.0 KV. Diameters were measured by measureIT software, Particle's distribution was fitted to single-pick Gaussian using OriginPro software.

Table 5 below presents the physicochemical characterization of NPs formulated by double emulsion method.

Table 6 below presents the physicochemical characterization of NPs formulated by microfluidic chip.

TABLE 5

| Particles | Size (nm) | PDI | Zeta Potential (mV) |
| --- | --- | --- | --- |
| NPs (empty) | 214 ± 3 | 0.14 ± 0.02 | −4.46 ± 1.56 |
| NPs (DBF) | 178 ± 2 | 0.12 ± 0.03 | −2.12 ± 0.58 |
| NPs (SLM) | 233 ± 7 | 0.21 ± 0.06 | −2.7 ± 0.6 |
| NPs (SLM + DBF) | 566 ± 40 | 0.7 ± 0.16 | −4.08 ± 0.4 |

TABLE 6

| Particles | Size (nm) | PdI | Zeta Potential (mV) |
| --- | --- | --- | --- |
| Nps-PLGA | 73.58 ± 0.26 | 0.29 ± 0.01 | −18.3 ± 3.57 |
| Nps-PLGA– DBF – SLM | 38.81 ± 0.36 | 0.426 ± 0.004 | Not measured |
| Man-PLGA | 55.08 ± 0.51 | 0..255 ± 0.005 | −10.5 ± 0.948 |
| Man-PLGA DBF + SLM | 53.15 ± 0.538 | 0.25 ± 0.011 | −13.3 ± 1.62 |

FIG. 9A presents environmental SEM images of PLGA-Nanoparticles and FIG. 9B presents environmental SEM images of Mannose-PLGA-Nanoparticles, prepared by Double emulsion-solvent evaporation (w/o/w) method.

Biocompatibility:

Biocompatibility was evaluated using the Red blood cell lysis (RBS) assay.

Mannose-NPs and NPs were prepared at 5 mg/mL concentration 1, 0.5, 0.1, 0.05, 0.001 and 0.0001 mg/mL concentrations. SDS and 70 KDa dextran solutions were prepared at the same concentrations to use as positive and negative controls respectively. Samples were incubated for 1 hour at 37° C. in equal volume of 2% (w/w) rat red blood cells (RBC) solution that was taken from 2 different rats. Samples were centrifuged at 1000 RCF for 10 minutes. The supernatants were then transferred to a 96-wells plate and absorbance was red at 550 nm using a SpectraMax M5e plate reader (Molecular Devices, Sunnyvale, Calif., USA). Results were normalized to 100% lysis obtained by incubation in 1% (v/v) Triton X-100.

The obtained data is presented in FIG. 10, and show that Mannose-PLGA NPS and PLGA NPs are biocompatible and do not display hemolysis.

In Vitro Anticancer Activity of PLGA Nanoparticles on Human Melanoma A375 Cells:

A375 ($1 \times 10^4$ cells/0.5 mL per well) were plated onto 24 well plates in RPMI supplemented with 10% FBS. After incubation for 24 hours, cells were exposed to serial concentrations of free dabrafenib, free selumetinib, PLGA-dabrafenib, PLGA-selumetinib or PLGA-dabrafenib-selumetinib NPs. Following 72 hours of incubation, A375 were trypsinized and counted by Z1 Coulter® Particle Counter (Beckman Coulter™).

The obtained data is presented in FIG. 10 and show that encapsulation in PLGA nanoparticles maintained the in vitro anticancer activity of selumetinib and dabrafenib, either alone or in combination.

NPs Internalization in P-Selectin Expressing Cell Lines:

In order to target drugs to P-sel-expressing tumors, NPs encapsulating chemotherapeutic drugs were formulated using the monosaccharide mannose, which exhibits nanomolar affinity for P-sel (see, FIG. 12A). As P-sel is overexpressed on activated endothelium NPs should penetrate endothelial barriers, and exhibit a therapeutic advantage over a combination of free drugs or passively-targeted NPs in P-sel-expressing tumors.

Rhodamine-labeled mannose-NPs were formulated and the internalization of the mannose-PLGA Nps was evaluated by incubating glioblastoma cells lines (U-87 MG, U251 and GL261; $1 \times 10^6$ cells per sample) with 1 mg/mL suspension of Rhodamine labelled mannose-PLGA NPs for 8 hours. The cells were then washed three times in PBS and the internalized fluorescence was evaluated by Gallios™ Flow Cytometer (Beckman Coulter™).

The obtained data is presented in FIG. 12B, and show the high specific binding of the Man-NPs to the three GB cell lines.

Example 6

The transnational and multidisciplinary approach aims to evaluate the therapeutic potential of multimodal precision nanomedicine, which targets brain metastasis. This can include the PD-L1 siRNA and both dabrafenib and trametinib or other BRAFi and MEKi combinations. The association of trametinib with dabrafenib and other combination of drugs mentioned previously (MEKi with temozolomide or paclitaxel or camptothecin, for example) both entrapped in a single NP, advantageously provides improved pharmacokinetics (PK) and potential synergism of two promising drugs for melanoma brain metastases.

Alternatively, for melanoma not bearing the BRAF mutation, other drug combinations are used, for example paclitaxel and a MEK inhibitor such as trametinib.

The effect of a combined administration of both MEKi (selumetinib) and BRAFi (dabrafenib) in human BRAF-mutated melanomas (A375, 5B1, WM115) was tested as the drugs were shown to exhibit a synergistic effect (combination index (CI)=0.6).

Similar assays were performed with MEKi and temozolomide or paclitaxel, for melanoma cells which do not bear the BRAF mutation (such as some of the Patient-derived melanoma collected or Ret-melanoma brain metastases which bear the V600G mutated BRAF that is not sensitive to conventional BRAFi). The melanoma cells were treated with free selumetinib, free Paclitaxel or both, for which data is presented in FIG. 13A, or with free selumetinib, temozolomide or both, for which data is presented in FIG. 13B. The combination of the free drugs was synergistic and demonstrated CI=0.3 for MEKi and paclitaxel and CI=0.2 for MEKi and temozolomide.

The effect of free selumetinib, PGA-Selumetinib (see, Scheme 19), free Paclitaxel, PGA-paclitaxel or both on proliferation of A375 melanoma cells was also tested.

PGA-Paclitaxel conjugate was prepared as described, for example, in WO 2013/132485.

The obtained data is presented in FIG. 14 and show that the combination of the free drugs was synergistic and demonstrated CI=0.08.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A polymeric conjugate comprising a polymeric matrix having associated therewith a first agent and an additional agent, wherein said first agent is selected from selumetinib and a structural analog thereof, and wherein said additional agent is selected from dabrafenib and a structural analog thereof and acts in synergy with said first agent in the treatment of melanoma, wherein a mol ratio of said first agent and said additional agent is at least 3:1.

2. The polymeric conjugate of claim 1, wherein said polymeric matrix comprises a polymeric backbone comprised of a plurality of backbone units, wherein a first portion of said backbone units has said first agent covalently attached thereto and a second portion of said backbone units has said additional agent covalently attached thereto.

3. The polymeric conjugate of claim 2, wherein at least one of said first agent and said additional agent is attached to said backbone units via a linker.

4. The polymeric conjugate of claim 3, wherein said linker is a biodegradable linker.

5. The polymeric conjugate of claim 2, being represented by Formula I:

$$-[A]_y-[A]_x-[A]_z-[A]_n-$$
$$\quad\quad\;\; |\quad\; |\quad\; |$$
$$\quad\quad\; T_1\; T_2\; L$$

Formula I wherein:

A is a backbone unit within said polymeric backbone;

A-T1 is a backbone unit within said polymeric backbone having attached thereto said first agent;

A-T2 is a backbone unit within said polymeric backbone having attached thereto said additional agent that acts in synergy with said first agent in the treatment of melanoma;

A-L is a backbone unit having attached thereto a targeting moiety;

y ranges from 50 to 99.9 mol percent;

x ranges from 0.1 to 50 mol percent; and z ranges from 0.1 to 50 mol percent; and n ranges from 0 to 10 mol percent.

6. The polymeric conjugate of claim 2, wherein said plurality of backbone units forms a polymeric backbone corresponding to a polymeric backbone of polyglutamic acid (PGA).

7. The polymeric conjugate of claim 1, wherein said polymeric matrix comprises a plurality of particles, and said first agent is associated with at least a first portion of said particles.

8. The polymeric conjugate of claim 7 wherein said polymeric matrix comprises a plurality of particles, and said additional agent is associated with at least a second portion of said particles.

9. The polymeric conjugate of claim 7, wherein said additional agent that acts in synergy with said first agent is associated with said at least first portion of said particles.

10. The polymeric conjugate of claim 7, wherein said particles comprise PLGA.

11. The polymeric conjugate of claim 1, wherein said additional agent is a structural analog of dabrafenib.

12. The polymeric conjugate of claim 11, wherein said structural analog of dabrafenib comprises a diol.

13. The polymeric conjugate of claim 1, wherein a mol ratio of said first and second agents is 3:1.

14. The polymeric conjugate of claim 1, further comprising a targeting moiety attached to said polymeric matrix, said targeting moiety being a ligand of a cell-surface receptor expressed in melanoma cells.

15. A pharmaceutical composition comprising the polymeric conjugate of claim 1, and a pharmaceutically acceptable carrier.

16. A method of treating a cancerous disease associated with a polypeptide that is associated with onset or progression of melanoma in a subject in need thereof, the method comprising administering to the subject a therapeutically effective amount of the polymeric conjugate of claim 1.

17. The method of claim 16, wherein said disease is melanoma.

18. The method of claim 17, wherein said melanoma is CNS-metastasizing melanoma.

19. A process of preparing the conjugate of claim 1, the process comprising coupling said first agent to a polymer corresponding to said polymeric backbone.

20. The process of claim 19, further comprising, prior to said coupling, modifying said first agent, to thereby generate a reactive group chemically compatible with a reactive group of said polymer.

21. A polymeric conjugate represented by the formula:

wherein:

T1 is selumetinib or a structural analog thereof;

T2 is dabrafenib or a structural analog thereof;

L is a targeting moiety which exhibits high affinity to polypeptides that are expressed on the surface of tumor cells or in the microenvironment of tumor cells;

y ranges from 50 to 99.9 mol percent;
x ranges from 0.1 to 50 mol percent;
z ranges from 0.1 to 20 mol percent; and
n ranges from 0 to 10 mol percent,
wherein a mol ratio of said selumetinib and said dabrafenib is at least 3:1.

22. The polymeric conjugate of claim 21, wherein said first agent is attached to said first portion of said backbone units via a biodegradable bond, a biodegradable spacer or a biodegradable linker.

23. The polymeric conjugate of claim 21, wherein said mol ratio is 3:1.

24. A pharmaceutical composition comprising the polymeric conjugate of claim 21, and a pharmaceutically acceptable carrier.

25. A method of treating melanoma in a subject in need thereof, the method comprising administering to the subject a therapeutically effective amount of the polymeric conjugate of claim 21.

26. The method of claim 25, wherein said melanoma is CNS-metastasizing melanoma.

* * * * *

```
                          SEQUENCE LISTING

<160> NUMBER OF SEQ ID NOS: 23

<210> SEQ ID NO 1
<211> LENGTH: 8
<212> TYPE: PRT
<213> ORGANISM: Artificial sequence
<220> FEATURE:
<223> OTHER INFORMATION: NCAM targeting amino acid sequence

<400> SEQUENCE: 1
```

```
Gly Asp Asp Ser Asp Glu Glu Asn
1               5
```

<210> SEQ ID NO 2

<400> SEQUENCE: 2

000

<210> SEQ ID NO 3
<211> LENGTH: 12
<212> TYPE: PRT
<213> ORGANISM: Artificial sequence
<220> FEATURE:
<223> OTHER INFORMATION: NCAM targeting amino acid sequence

<400> SEQUENCE: 3

```
Gly Ala Ser Lys Lys Pro Lys Arg Asn Ile Lys Ala
1               5                   10
```

<210> SEQ ID NO 4

<400> SEQUENCE: 4

000

<210> SEQ ID NO 5
<211> LENGTH: 7
<212> TYPE: PRT
<213> ORGANISM: Artificial sequence
<220> FEATURE:
<223> OTHER INFORMATION: NCAM targeting amino acid sequence

<400> SEQUENCE: 5

```
Asp Asp Ser Asp Glu Glu Asn
1               5
```

<210> SEQ ID NO 6
<211> LENGTH: 11
<212> TYPE: PRT
<213> ORGANISM: Artificial sequence
<220> FEATURE:
<223> OTHER INFORMATION: NCAM targeting amino acid sequence

<400> SEQUENCE: 6

```
Ala Ser Lys Lys Pro Lys Arg Asn Ile Lys Ala
1               5                   10
```

<210> SEQ ID NO 7
<211> LENGTH: 3
<212> TYPE: PRT
<213> ORGANISM: Artificial sequence
<220> FEATURE:
<223> OTHER INFORMATION: Angiogenesis targeting moieties amino acid
      sequence

<400> SEQUENCE: 7

```
Arg Gly Asp
1
```

<210> SEQ ID NO 8
<211> LENGTH: 5
<212> TYPE: PRT
<213> ORGANISM: Artificial sequence
<220> FEATURE:
<223> OTHER INFORMATION: Angiogenesis targeting moieties amino acid
      sequence <220> FEATURE:
<221> NAME/KEY: MISC_FEATURE
<222> LOCATION: (1)..(5)
<223> OTHER INFORMATION: cyclic peptide
<220> FEATURE:
<221> NAME/KEY: MISC_FEATURE
<222> LOCATION: (4)..(4)
<223> OTHER INFORMATION: D-Phe

<400> SEQUENCE: 8

Arg Gly Asp Phe Lys
1               5

<210> SEQ ID NO 9
<211> LENGTH: 11
<212> TYPE: PRT
<213> ORGANISM: Artificial sequence
<220> FEATURE:
<223> OTHER INFORMATION: Angiogenesis targeting moieties amino acid
      sequence
<220> FEATURE:
<221> NAME/KEY: DISULFID
<222> LOCATION: (1)..(11)
<223> OTHER INFORMATION: Disulfide bonds between the cysteins:
      Cys2-Cys10 and Cys4-Cys8

<400> SEQUENCE: 9

Ala Cys Asp Cys Arg Gly Asp Cys Phe Cys Gly
1               5                   10

<210> SEQ ID NO 10
<211> LENGTH: 5
<212> TYPE: PRT
<213> ORGANISM: Artificial sequence
<220> FEATURE:
<223> OTHER INFORMATION: Angiogenesis targeting moieties amino acid
      sequence
<220> FEATURE:
<221> NAME/KEY: MISC_FEATURE
<222> LOCATION: (1)..(5)
<223> OTHER INFORMATION: Two cyclic peptides linked via the lysine side
      chains and glutamic acid (linker, side chain)
<220> FEATURE:
<221> NAME/KEY: MISC_FEATURE
<222> LOCATION: (1)..(5)
<223> OTHER INFORMATION: cyclic peptide
<220> FEATURE:
<221> NAME/KEY: MISC_FEATURE
<222> LOCATION: (4)..(4)
<223> OTHER INFORMATION: D-Phe

<400> SEQUENCE: 10

Arg Gly Asp Phe Lys
1               5

<210> SEQ ID NO 11
<211> LENGTH: 2
<212> TYPE: PRT
<213> ORGANISM: Artificial sequence
<220> FEATURE:
<223> OTHER INFORMATION: Cathepsin B-cleavable linkers amino acid
      sequence
<220> FEATURE:
<221> NAME/KEY: MISC_FEATURE
<222> LOCATION: (1)..(1)
<223> OTHER INFORMATION: X= Citrulline

<400> SEQUENCE: 11

Xaa Val
1

```
<210> SEQ ID NO 12
<211> LENGTH: 2
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 12

Phe Lys
1

<210> SEQ ID NO 13
<211> LENGTH: 2
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 13

Val Arg
1

<210> SEQ ID NO 14
<211> LENGTH: 2
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 14

Phe Arg
1

<210> SEQ ID NO 15
<211> LENGTH: 4
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 15

Gly Phe Leu Gly
1

<210> SEQ ID NO 16
<211> LENGTH: 4
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 16

Gly Phe Ala Leu
1

<210> SEQ ID NO 17
<211> LENGTH: 4
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 17
```

Ala Leu Ala Leu
1

<210> SEQ ID NO 18
<211> LENGTH: 3
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 18

Gly Leu Gly
1

<210> SEQ ID NO 19
<211> LENGTH: 3
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 19

Gly Phe Gly
1

<210> SEQ ID NO 20
<211> LENGTH: 6
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 20

Gly Phe Leu Gly Phe Lys
1               5

<210> SEQ ID NO 21
<211> LENGTH: 1
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 21

Arg
1

<210> SEQ ID NO 22
<211> LENGTH: 2
<212> TYPE: PRT
<213> ORGANISM: Artificial sequence
<220> FEATURE:
<223> OTHER INFORMATION: Cathepsin B-cleavable linkers amino acid
      sequence

<400> SEQUENCE: 22

Arg Arg
1

<210> SEQ ID NO 23
<211> LENGTH: 14
<212> TYPE: PRT
<213> ORGANISM: Artificial sequence

```
<220> FEATURE:
<223> OTHER INFORMATION: Cathepsin B-cleavable linkers amino acid
      sequence

<400> SEQUENCE: 23

Glu Glu Glu Glu Glu Glu Asp Asp Asp Asp Asp Asp Asp
1               5                   10
```